US012558216B2

(12) United States Patent
Siegel et al.

(10) Patent No.: US 12,558,216 B2
(45) Date of Patent: Feb. 24, 2026

(54) DEVICE FOR SECURING HEART VALVE LEAFLETS

(71) Applicant: CEDARS-SINAI MEDICAL CENTER, Los Angeles, CA (US)

(72) Inventors: Robert James Siegel, Beverly Hills, CA (US); Lawrence Eric Ong, Beverly Hills, CA (US); Niclas Henning Zieger, Pasadena, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 761 days.

(21) Appl. No.: 17/822,903

(22) Filed: Aug. 29, 2022

(65) Prior Publication Data

US 2023/0050824 A1     Feb. 16, 2023

Related U.S. Application Data

(63) Continuation of application No. 16/479,584, filed as application No. PCT/US2018/015105 on Jan. 24, 2018, now Pat. No. 11,439,501.

(Continued)

(51) Int. Cl.
*A61F 2/24*          (2006.01)

(52) U.S. Cl.
CPC .......... *A61F 2/2403* (2013.01); *A61F 2/2418* (2013.01); *A61F 2/2427* (2013.01); *A61F 2220/0025* (2013.01); *A61F 2220/0075* (2013.01); *A61F 2220/0091* (2013.01); *A61F 2230/0013* (2013.01); *A61F 2230/0095* (2013.01); *A61F 2250/0071* (2013.01)

(58) Field of Classification Search
CPC .................. A61F 2/2403; A61F 2/2427; A61F 2220/0025; A61F 2220/0091; A61B 17/12013
See application file for complete search history.

(56) References Cited

U.S. PATENT DOCUMENTS 4,777,951 A     10/1988  Cribier
5,171,259 A     12/1992  Inoue
         (Continued)

FOREIGN PATENT DOCUMENTS

CN          106175986        12/2016
EP          1 674 040        6/2006
         (Continued)

OTHER PUBLICATIONS

Bhargava et al., "Biosense Left Ventricular Electromechanical Mapping", Asian Cardiovasc Thorac Ann 1999, 7:345-52.
(Continued)

*Primary Examiner* — Dinah Baria
(74) *Attorney, Agent, or Firm* — Knobbe, Martens, Olson & Bear, LLP

(57) ABSTRACT
A heart valve prosthesis is provided that includes a first member and a second member. The first member comprises a first central portion to be disposed adjacent to a line of coaptation on a first side of two adjacent heart leaflets and peripheral portions to be placed into direct contact with the two adjacent heart leaflets. The second member is separate from or can be separable from the first member, for example during delivery. The second member has a central portion and peripheral portions configured to be placed into direct contact with a second side of the two adjacent heart leaflets.

16 Claims, 80 Drawing Sheets

Related U.S. Application Data

(60) Provisional application No. 62/450,474, filed on Jan. 25, 2017.

(56) References Cited

U.S. PATENT DOCUMENTS

| | | | |
|---|---|---|---|
| 5,201,880 A | 4/1993 | Wright et al. | |
| 5,573,540 A | 11/1996 | Yoon | |
| 5,575,799 A | 11/1996 | Bolanos et al. | |
| 5,609,598 A | 3/1997 | Laufer et al. | |
| 5,626,588 A | 5/1997 | Sauer et al. | |
| 5,716,367 A | 2/1998 | Koike et al. | |
| 6,029,671 A | 2/2000 | Stevens et al. | |
| 6,051,014 A | 4/2000 | Jang | |
| 6,090,096 A | 7/2000 | St. Goar et al. | |
| 6,117,144 A | 9/2000 | Nobles et al. | |
| 6,117,145 A | 9/2000 | Wood et al. | |
| 6,136,010 A | 10/2000 | Modesitt et al. | |
| 6,165,183 A | 12/2000 | Kuehn et al. | |
| 6,197,043 B1 | 3/2001 | Davidson | |
| 6,206,893 B1 | 3/2001 | Klein et al. | |
| 6,269,819 B1 | 8/2001 | Oz et al. | |
| 6,287,321 B1 | 9/2001 | Jang | |
| 6,312,446 B1 | 11/2001 | Huebsch et al. | |
| 6,312,447 B1 | 11/2001 | Grimes | |
| 6,325,067 B1 | 12/2001 | Sterman et al. | |
| 6,328,757 B1 | 12/2001 | Matheny | |
| 6,461,366 B1 | 10/2002 | Seguin | |
| 6,508,828 B1 | 1/2003 | Akerfeldt et al. | |
| 6,575,971 B2 | 6/2003 | Hauck et al. | |
| 6,629,534 B1 | 10/2003 | St. Goar et al. | |
| 6,635,068 B1 | 10/2003 | Dubrul et al. | |
| 6,752,813 B2 | 6/2004 | Goldfarb et al. | |
| 6,770,083 B2 | 8/2004 | Seguin | |
| 6,926,715 B1 | 8/2005 | Hauck et al. | |
| 6,932,792 B1 | 8/2005 | St. Goar et al. | |
| 6,945,978 B1 | 9/2005 | Hyde | |
| 7,048,754 B2 | 5/2006 | Martin et al. | |
| 7,226,467 B2 | 6/2007 | Lucatero et al. | |
| 7,276,078 B2 | 10/2007 | Spenser et al. | |
| 7,404,824 B1 | 7/2008 | Webler et al. | |
| 7,563,267 B2 | 7/2009 | Goldfarb et al. | |
| 7,569,062 B1 | 8/2009 | Kuehn et al. | |
| 7,604,646 B2 | 10/2009 | Goldfarb et al. | |
| 7,632,308 B2 | 12/2009 | Loulmet | |
| 7,635,329 B2 | 12/2009 | Goldfarb et al. | |
| 7,666,204 B2 | 2/2010 | Thornton et al. | |
| 7,704,269 B2 | 4/2010 | St. Goar et al. | |
| 7,736,388 B2 | 6/2010 | Goldfarb et al. | |
| 7,811,296 B2 | 10/2010 | Goldfarb et al. | |
| 7,828,819 B2 | 11/2010 | Webler et al. | |
| 7,854,762 B2 | 12/2010 | Speziali et al. | |
| 7,938,827 B2 | 5/2011 | Hauck et al. | |
| 7,981,123 B2 | 7/2011 | Seguin | |
| 8,052,592 B2 | 11/2011 | Goldfarb et al. | |
| 8,123,703 B2 | 2/2012 | Martin et al. | |
| 8,172,856 B2 | 5/2012 | Eigler et al. | |
| 8,216,256 B2 | 7/2012 | Raschdorf, Jr. et al. | |
| 8,216,302 B2 | 7/2012 | Wilson et al. | |
| 8,303,608 B2 | 11/2012 | Goldfarb et al. | |
| 8,323,334 B2 | 12/2012 | Deem et al. | |
| 8,382,796 B2 | 2/2013 | Blaeser et al. | |
| 8,409,219 B2 | 4/2013 | Kelley et al. | |
| 8,409,273 B2 | 4/2013 | Thornton et al. | |
| 8,545,551 B2 | 10/2013 | Loulmet | |
| 8,568,472 B2 | 10/2013 | Marchand et al. | |
| 8,920,463 B2 | 12/2014 | McGukin, Jr. et al. | |
| 8,932,325 B2 | 1/2015 | Stanley et al. | |
| 8,992,605 B2 | 3/2015 | Zakai et al. | |
| 9,023,099 B2 | 5/2015 | Duffy et al. | |
| 9,060,858 B2 | 6/2015 | Thornton et al. | |
| 9,474,605 B2 | 10/2016 | Rowe et al. | |
| 9,498,330 B2 | 11/2016 | Solem | |
| 9,763,658 B2 | 9/2017 | Eigler et al. | |
| 10,080,657 B2 | 9/2018 | Siegel | |
| 10,105,221 B2 | 10/2018 | Siegel | |
| 10,478,304 B2 | 11/2019 | McNiven et al. | |
| 10,499,905 B2 | 12/2019 | Eigler et al. | |
| 10,758,241 B1 | 9/2020 | Lashinski et al. | |
| 10,758,265 B2 | 9/2020 | Siegel | |
| 10,799,359 B2 | 10/2020 | Siegel et al. | |
| 10,898,323 B2 | 1/2021 | Siegel | |
| 11,241,308 B2 | 2/2022 | Siegel et al. | |
| 11,291,544 B2 | 4/2022 | Siegel et al. | |
| 11,439,501 B2 | 9/2022 | Siedel et al. | |
| 11,653,948 B2 | 5/2023 | Siegel | |
| 11,730,591 B2 | 8/2023 | Siegel et al. | |
| 12,279,956 B2 | 4/2025 | Siegel et al. | |
| 12,370,043 B2 | 7/2025 | Siegel et al. | |
| 2001/0005787 A1 | 6/2001 | Oz et al. | |
| 2002/0013571 A1 | 1/2002 | Goldfarb et al. | |
| 2002/0183787 A1 | 12/2002 | Wahr et al. | |
| 2003/0120340 A1 | 6/2003 | Liska et al. | |
| 2004/0044350 A1 | 3/2004 | Martin et al. | |
| 2004/0260322 A1 | 12/2004 | Rudko et al. | |
| 2005/0033446 A1 | 2/2005 | Deem et al. | |
| 2005/0107871 A1 | 5/2005 | Realyvasquez et al. | |
| 2005/0143811 A1 | 6/2005 | Realyvasquez | |
| 2005/0222489 A1 | 10/2005 | Rahdert et al. | |
| 2005/0273135 A1 | 12/2005 | Chanduszko et al. | |
| 2006/0004442 A1 | 1/2006 | Spenser et al. | |
| 2006/0020275 A1 | 1/2006 | Goldfarb et al. | |
| 2006/0074484 A1 | 4/2006 | Huber | |
| 2006/0089671 A1 | 4/2006 | Goldfarb et al. | |
| 2006/0229708 A1 | 10/2006 | Powell et al. | |
| 2006/0241745 A1 | 10/2006 | Solem | |
| 2006/0293739 A1 | 12/2006 | Vijay | |
| 2007/0032850 A1 | 2/2007 | Ruiz et al. | |
| 2007/0038293 A1 | 2/2007 | St.Goar et al. | |
| 2007/0055303 A1 | 3/2007 | Vidlund et al. | |
| 2007/0093890 A1 | 4/2007 | Eliasen et al. | |
| 2007/0198082 A1 | 8/2007 | Kapadia et al. | |
| 2007/0255273 A1 | 11/2007 | Fernandez et al. | |
| 2007/0270943 A1 | 11/2007 | Solem et al. | |
| 2007/0293943 A1 | 12/2007 | Quinn | |
| 2009/0048668 A1 | 2/2009 | Wilson et al. | |
| 2009/0062836 A1 | 3/2009 | Kurrus | |
| 2009/0076600 A1 | 3/2009 | Quinn | |
| 2009/0177266 A1 | 7/2009 | Powell et al. | |
| 2010/0022823 A1 | 1/2010 | Goldfarb et al. | |
| 2010/0217283 A1 | 8/2010 | St.Goar et al. | |
| 2010/0298929 A1 | 11/2010 | Thornton et al. | |
| 2011/0029071 A1 | 2/2011 | Zlotnick et al. | |
| 2011/0066233 A1 | 3/2011 | Thornton et al. | |
| 2011/0082495 A1 | 4/2011 | Ruiz | |
| 2011/0106245 A1 | 5/2011 | Miller et al. | |
| 2011/0137397 A1 | 6/2011 | Chau et al. | |
| 2011/0218620 A1 | 9/2011 | Meiri et al. | |
| 2011/0224655 A1 | 9/2011 | Asirvatham et al. | |
| 2011/0264208 A1 | 10/2011 | Duffy et al. | |
| 2011/0313437 A1 | 12/2011 | Yeh | |
| 2011/0319989 A1 | 12/2011 | Lane et al. | |
| 2012/0010700 A1 | 1/2012 | Spenser | |
| 2012/0065464 A1 | 3/2012 | Ellis et al. | |
| 2012/0078360 A1 | 3/2012 | Rafiee | |
| 2012/0095547 A1 | 4/2012 | Chuter | |
| 2012/0116418 A1 | 5/2012 | Belson et al. | |
| 2012/0179184 A1 | 7/2012 | Orlov | |
| 2012/0191181 A1 | 7/2012 | Kassab et al. | |
| 2012/0245678 A1 | 9/2012 | Solem | |
| 2012/0310331 A1 | 12/2012 | Eigler et al. | |
| 2012/0310334 A1 | 12/2012 | Dolan | |
| 2013/0018414 A1 | 1/2013 | Widimski et al. | |
| 2013/0030522 A1 | 1/2013 | Rowe et al. | |
| 2013/0066341 A1 | 3/2013 | Ketai et al. | |
| 2013/0066342 A1 | 3/2013 | Dell et al. | |
| 2013/0110227 A1 | 5/2013 | Quadri et al. | |
| 2013/0197559 A1 | 8/2013 | Hariton et al. | |
| 2013/0226288 A1 | 8/2013 | Goldwasser et al. | |
| 2013/0253547 A1 | 9/2013 | Goldfarb et al. | |
| 2013/0261739 A1 | 10/2013 | Kuehn | |
| 2013/0297010 A1 | 11/2013 | Bishop et al. | |
| 2013/0338764 A1 | 12/2013 | Thornton et al. | |
| 2014/0039607 A1 | 2/2014 | Kovach | |
| 2014/0039608 A1 | 2/2014 | Eidenschink | |

(56) References Cited

U.S. PATENT DOCUMENTS

| | | |
|---|---|---|
| 2014/0058502 A1 | 2/2014 | Marchand et al. |
| 2014/0222136 A1 | 8/2014 | Geist et al. |
| 2014/0236198 A1 | 8/2014 | Goldfarb et al. |
| 2014/0277426 A1 | 9/2014 | Dakin et al. |
| 2014/0371789 A1 | 12/2014 | Hariton et al. |
| 2015/0038988 A1 | 2/2015 | Tegels et al. |
| 2015/0134057 A1 | 5/2015 | Rourke et al. |
| 2015/0173765 A1 | 6/2015 | Miller et al. |
| 2016/0008129 A1 | 1/2016 | Siegel |
| 2016/0324635 A1 | 11/2016 | Vidlund et al. |
| 2017/0100250 A1 | 4/2017 | Marsot et al. |
| 2017/0143478 A1 | 5/2017 | Schwartz et al. |
| 2017/0174979 A1 | 6/2017 | Sanders |
| 2017/0216028 A1 | 8/2017 | Khalil |
| 2017/0245988 A1 | 8/2017 | Siegel et al. |
| 2017/0325842 A1 | 11/2017 | Siegel et al. |
| 2018/0021133 A1 | 1/2018 | Barbarino |
| 2018/0193016 A1 | 7/2018 | Eigler et al. |
| 2018/0289478 A1 | 10/2018 | Quill |
| 2019/0008638 A1 | 1/2019 | Siegel et al. |
| 2019/0076246 A1 | 3/2019 | Siegel |
| 2019/0117388 A1 | 4/2019 | Jarral et al. |
| 2019/0298516 A1 | 10/2019 | Siegel et al. |
| 2019/0343630 A1 | 11/2019 | Kizuka |
| 2019/0365529 A1 | 12/2019 | Siegel et al. |
| 2020/0030092 A1 | 1/2020 | Tuval et al. |
| 2020/0121454 A1 | 4/2020 | Spence |
| 2020/0367926 A1 | 11/2020 | Siegel |
| 2020/0375730 A1 | 12/2020 | Siegel et al. |
| 2021/0030534 A1 | 2/2021 | Siegel et al. |
| 2022/0226113 A1 | 7/2022 | Siegel et al. |
| 2024/0277468 A1 | 8/2024 | Siegel et al. |

FOREIGN PATENT DOCUMENTS

| | | |
|---|---|---|
| EP | 1 539 015 | 4/2011 |
| EP | 2 849 681 | 8/2017 |
| EP | 3 269 330 | 1/2018 |
| JP | H05-220174 | 8/1993 |
| JP | 2004-008805 | 1/2004 |
| JP | 2004-530451 | 10/2004 |
| JP | 2004-531337 | 10/2004 |
| JP | 2008-142563 | 6/2008 |
| JP | 2008-514307 | 8/2008 |
| WO | WO 00/60995 | 10/2000 |
| WO | WO 01/26557 | 4/2001 |
| WO | WO 01 /070116 | 9/2001 |
| WO | WO 02/034167 | 5/2002 |
| WO | WO 03/049619 | 6/2003 |
| WO | WO 2004/012583 | 2/2004 |
| WO | WO 2005/058239 | 6/2005 |
| WO | WO 2007/011994 | 1/2007 |
| WO | WO 2011/116379 | 9/2011 |
| WO | WO 2014/138284 | 9/2014 |
| WO | WO 2014/138482 | 9/2014 |
| WO | WO 2016/040526 | 3/2016 |
| WO | WO 2016/077783 | 5/2016 |
| WO | WO 2017/015632 | 1/2017 |
| WO | WO 2018/140535 | 8/2018 |
| WO | WO 2019/152598 | 8/2019 |
| WO | WO 2020/197854 | 10/2020 |
| WO | WO 2022/266022 | 12/2022 |

OTHER PUBLICATIONS

Black MD, M., Division of Pediatric Cardiac Surgery, Standford University School of Medicine, California, USA, Minimally Invasive Pediatric Cardiac Surgery, Online Article in 4 pages.

Ethicon Wound Closure Manual—Chapter 6, Research and Development at Ethicon, Inc.—An Ongoing Process of Change and Improvement, Online at www.ethiconinc.com in 4 pages.

Gersak MD, Ph.D., B., "Mitral Valve Repair or Replacement on the Beating Heart", The Heart Surgery Forum #2000-1989, Jun. 8, 2000, pp. 232-237, 2000 Forum Multimedia Publishing, LLC.

Perclose A-T, 6F Suture-Mediated Closure (SMC) System, Instructions for Use distributed in the U.S. by Abbott laboratories, Inc. 2002, 2006 Abbott Laboratories in 11 pages.

Quealy et al., "Use of Combined Intravascular Ultrasound and PTCA Catheter: Clinical Utility", Chapter 12, pp. 245-250.

Extended European Search Report issued in European Application No. 16828665.6, dated Mar. 28, 2019, in 7 pages.

Extended European Search Report issued in European Application No. 18744791.7, dated Aug. 5, 2020, in 9 pages.

International Search Report and Written Opinion issued in PCT Application No. PCT/US2016/043750, dated Oct. 19, 2016, in 19 pages.

International Search Report and Written Opinion issued in PCT Application No. PCT/US2018/015105, dated May 21, 2018, in 15 pages.

DEVICE FOR SECURING HEART VALVE LEAFLETS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

The present disclosure relates to devices and methods for treating regurgitation in a heart valve.

Description of the Related Art

The tricuspid valve separates the right lower heart chamber (the right ventricle) from the right upper heart chamber (right atrium). Tricuspid regurgitation is a disorder in which this valve does not close tight enough. This problem causes blood to flow backward into the right upper heart chamber (atrium) when the right lower heart chamber (ventricle) contracts. Tricuspid regurgitation is leakage of blood backwards through the tricuspid valve each time the right ventricle contracts. Tricuspid regurgitation usually results from an enlarged lower heart chamber (called the ventricle) or from any other condition that constrains the blood flow from the right ventricle to the lungs. Sometimes long-standing disorders, such as emphysema or pulmonary stenosis can cause problems that affect the tricuspid valve which is "upstream" from the lungs. To compensate, the right ventricle enlarges so that it can pump harder, which sometimes causes the tricuspid opening to become stretched out and floppy. When valve disease is severe, it may be necessary to repair or replace the diseased valve. Valve repair is the most common surgical treatment for tricuspid valve disease. Tricuspid valve repair can be done alone or in combination with treatments for other heart problems.

Tricuspid valve repair using an annuloplasty ring is a common surgical approach for tricuspid regurgitation and may be performed for primary tricuspid disease or for combined cases with other valve surgery (mitral, aortic). Traditional tricuspid valve repair is an open-heart procedure performed through a 6-8 inch incision through the breastbone (sternum).

SUMMARY OF THE INVENTION

For these reasons, there exists a need for minimally invasive methods of tricuspid valve repair. The present disclosure is directed to valve fixation devices that can be delivered endovascularly.

In one embodiment a heart valve prosthesis is provided that includes a first member and a second member. The first member comprises a first central portion to be disposed adjacent to a line of coaptation on a first side of two adjacent heart leaflets and peripheral portions to be placed into direct contact with the two adjacent heart leaflets. The second member is separate from or can be separable from the first member. The second member has a central portion and peripheral portions configured to be placed into direct contact with a second side of the two adjacent heart leaflets.

By making the first member and the second member separable from each other, the first and second members can be initially coupled together in a first configuration. The first configuration can be suitable for delivery in a catheter assembly, e.g., with the longitudinal axes of the first and second members aligned with a longitudinal axis of a distal portion of the catheter assembly. The longitudinal axes of the first and second members aligned with a delivery direction or trajectory in the first configuration. The first and second member can be assembled in a second configuration different from the first configuration in which the longitudinal axes of the first and second members are disposed transverse to the longitudinal axis of the distal portion of the catheter assembly. The second configuration can align the longitudinal axes of the first and second members transverse to the delivery direction or trajectory. A third configuration can be provided in which the first member is disassembled from the second member and allowed to move away from the second member. The first member can remain coupled to the second member by a tension member or other connector that can be slacked or released to allow a proximal-distal spacing tissues engaging surfaces of the first and second member to be increased and/or subsequently decreased.

In some variants, motion of the first and second members is controlled. For example, the first member can have a first hinge portion. One of the peripheral portions of the second member can have a second hinge portion. Motion of the first member can include pivoting the first member at the first and second hinge portions.

Upon pivoting the first member, a wire or other tension member or connector disposed between the first member and the second member can be slackened to allow the first member to shift distally relative to the second member. For example, the tension member or connector can be slackened to allow the first member to separate from the second member. Once the first member is separated the tension member provides for guided shifting or relative motion between the first member and the second member. The first member can be allowed to move distally relative to the second member in one technique. Prior to providing a slackened state, the tension member or wire holds a hinge portion of the first member against a hinge portion of the second member. After providing the slackened state, the first member can be released and brought into contact with the ventricular side of a valve and the second member can be shifted proximally from the first member.

In some variants, a tension member is provided through the first member and the second member at least in a delivery configuration. The tension member can be a guide member used to deliver one or both of the first member and the second member. In some examples, the tension member is a suture. The suture can be a continuous member that has both ends disposed at a proximal end of a delivery system and a middle U-shaped portion disposed around the first member during delivery. An advantage of a two-wire or suture approach is these approaches can align the first and second members. The two wires can bring the peripheral ends of the two plates into alignment. The tension member can be configured as a wire that can be loop shaped with one enclosed end. An additional benefit of a wire tension member is that more rotational control of the distal plate can be provided, e.g., for positioning the distal plate. Additionally, a rigid wire can reduce, minimize or prevent possible "helicoptering" of the distal plate in the blood flow that may happen with a flexible suture. "Helicoptering" can arise when the first member is released in the heart and swirling blood flow causes rotational motion of the first member.

In some variants, the first member is pivoted by disposing a tension member off-set from a hinge axis such that tension on the tension member creates a torque capable of rotating the first member about the hinge axis.

The first and second members are intended to be fastened against each other to entrap adjacent valve leaflets therebetween, securing two adjacent valve leaflets together along their coaptation line. The members may be deployed on each (i.e., distal and proximal) side of the valve independently prior to fastening against each other. Alternatively, the members may be integrated as a single deployable device to entrap adjacent valve leaflets. Alternatively, the members may incorporate features that constrain their relative motion to assist with deployment. This includes one or more of: features that allow the members to be sheathed for deployment such as mated male and female features that prevent the members from moving or separating within the sheath; features that may act as a hinge to facilitate movement of the members out of the sheath; and features such as serrations, barbs, or male and female features that assist with alignment and fixation in the deployed configuration. Once deployed, the members may be firmly fastened together to secure two adjacent leaflets along their coaptation line. This can be performed by applying compliant material around both members such as a tied suture, encasing all or a portion of the members with compliant material such as an elastomer sheath, and/or affixing a fastener such as a clip either around or through the members. The first and second member can be firmly fastened together by increasing tension in a tension member to cause pressure to be applied to leaflet portions trapped between the first and the second members. The tension member can include a wire and tension can be increased in a wire by twisting adjacent strands together.

In another embodiment, a heart valve prosthesis is provided that includes a first member configured to be advanced into a first heart chamber. The first member has a first central portion to be disposed adjacent to the line of coaptation of two adjacent heart leaflets. The two adjacent heart leaflets are disposed between the first heart chamber and a second heart chamber. The first member has peripheral portions to be placed into direct contact with the two adjacent heart leaflets. At least one of the peripheral portions of the first member has a concave recess formed in a mating face of the first member. The heart valve prosthesis includes a second member configured to be advanced into the second heart chamber. The second member has a central portion to be disposed adjacent to the line of coaptation of the two adjacent heart leaflets and peripheral portions configured to be placed into direct contact with the two adjacent heart leaflets. The second member is separate from the first member. The second member comprises convex protrusions extending from a second mating face. The first and second mating faces are brought into adjacency to trap heart valve leaflets therebetween when the first and second members are coupled. The convex protrusions and concave recesses are engaged when the first member and the second member are coupled to prevent lateral movement of the first and second members relative to each other.

In one variant of the foregoing, the first member includes a convex protrusion and the second member comprises a concave recess that receives the convex protrusion when the first and second members are coupled. In further variations, the first member includes a first convex portion, and a first concave recess and the second member comprises a second concave recess and a second convex protrusion. The first concave recess receives the second concave protrusion and the second concave recess receives the first convex protrusion when the first member and the second member are coupled together. These and other combinations of protrusions and recesses can be provided to enhance the stability of the first and second members when the first and second members are coupled to each other.

In another embodiment, a heart valve prosthesis is provided that includes a first member and a second member. The first member is configured to be advanced into a first heart chamber. The first heart chamber is separated from a second heart chamber by two adjacent heart leaflets. The first member has a first central portion to be disposed adjacent to a line of coaptation of two adjacent heart leaflets and peripheral portions separated from one another by the first central portion. The peripheral portions are adapted to be placed into direct contact with the two adjacent heart leaflets. The second member is configured to be advanced into the second heart chamber. The second member has a central portion configured to be disposed adjacent to the line of coaptation of the two adjacent heart leaflets and peripheral portions. The peripheral portions are configured to be placed into direct contact with the two adjacent heart leaflets. The second member is separate from the first member such that relative movement can be provided between the first member and the second member, e.g., for delivery and for placing a heart valve leaflet therebetween. Relative movement between the first and second members can include moving the central portions thereof. Relative movement between the first and second members can include moving the entire first member away from the second member during assembly of the heart valve prosthesis in the heart. A tissue-engaging side of the second member forms a concave arch that joins together the peripheral portions of the second member. At least one of the first member and the second member is deformable to allow at least a portion of the first member to be interposed between a base of the arch and an apex of the arch.

In another embodiment, a system for treating heart valve insufficiency is provided. The system includes a heart valve prosthesis and a catheter assembly. The heart valve prosthesis includes a distal body comprising a first hinge portion, a proximal body comprising a second hinge portion, and a connector configured to secure the distal body to the proximal body. The catheter assembly has an elongate outer tubular member comprising a lumen having an inner diameter a first elongate inner member. The first elongate inner member can include a distal face mating with a knot portion in some embodiment. The first elongate inner member can include a distal portion mating with a wire, which is a form of connector for components of the heart valve prosthesis. The catheter assembly can include a second elongate inner member. The second elongate inner member is disposed along, e.g., circumferentially surrounding, the first elongate inner member and comprising a distal face coupled with an end face of the proximal body.

In another embodiment, a method is provided in which a distal body and at least a portion of a proximal body is advanced into a first heart chamber of a heart by passing the distal body and at least a portion of the proximal body through a heart valve. The distal body is pivoted about the proximal body while maintaining contact between the proximal body and the distal body. The distal body is separated from the proximal body. The proximal body is disposed in, e.g., withdrawn to within, a second heart chamber. The proximal body can be withdrawn by passing at least a portion of the proximal body through the heart valve. A portion of a leaflet is captured between the proximal body and the distal body. The proximal body is secured to the distal body to keep the captured leaflets between the proximal body and the distal body. In one variation of the method, the distal body is coupled to the proximal body only by a tension member, such as a wire or suture, when the distal body is separated from the proximal body. In some variations, the proximal body and distal body are thereafter assembled within the heart. The proximal body and distal body can be initially assembled in a first configuration for delivery and then re-assembled in the heart following separation of the distal body from the proximal body.

Once applied the proximal and distal bodies can be affixed with a suture tied around or with a wire cinched around all or a portion of both bodies. Suture(s) or wire(s) can be guided through features such as grooves along or through the outside of the assembled bodies to prevent migration of the suture, or can be threaded through features such as through holes within the bodies. Once placed, the sutures can be affixed by a knot techniques assisted with one or more of: a knot pusher; held firmly together with crimp type fasteners; held together with the assistance of a clip that secures the suture against the proximal, distal, or both bodies; or some combination thereof. The proximal and distal bodies can be secured with a clip that passes either around or through both bodies. This clip may incorporate features that allow secure fastening, such as barbs, a deformable expanding tip as in a rivet, or threaded features. A wire can be cinched by twisting adjacent strands of the wire about each other. The adjacent strands can be proximal of the proximal body. The wire can be loop-shaped such that a portion of the wire between the adjacent strands is disposed around the distal body.

In one embodiment, a loading capsule is provided. The loading capsule includes a capsule body. The capsule body has a distal zone and a prosthesis loading zone. The distal zone is optionally configured to be inserted through a hemostatic valve. The prosthesis loading zone can be configured to receive components of a heart valve prosthesis in a delivery configuration, the capsule body, further comprising a proximal end, a distal end, and a lumen extending from the proximal end of the capsule body to the distal end of the capsule body.

In another embodiment, a method is provided wherein a peripheral edge and a peripheral portion of a first member is advanced into an opening in a loading capsule. A second member is placed into temporary engagement with the first member. The first member, a portion of the second member, and a portion of a connector are advanced into the loading capsule. A distal end of a control body is engaged with a peripheral edge of the second member.

BRIEF DESCRIPTION OF THE DRAWINGS

A more complete appreciation of the subject matter of this application and the various advantages thereof can be realized by reference to the following detailed description, in which reference is made to the accompanying drawings in which.

More detailed descriptions of various embodiments of catheter based delivery systems, components and methods useful to treat patients are set forth below.

DETAILED DESCRIPTION OF THE PREFERRED EMBODIMENT

This application is directed to heart valve repair systems and methods as well as heart valve prostheses that can be delivered thereby. Section I below discusses valvular insufficiency and blood regurgitation that result from poor coaptation of valve leaflets. Section II discusses a heart valve repair system that includes a delivery system adapted for endovascular delivery of heart valve prostheses discussed herein. Section III describes embodiments of heart valve prostheses, which can include a plurality of plate-like bodies that can be disposed on distal and proximal sides of a heart valve, such as a tricuspid valve, to reduce regurgitation. Section IV describes further delivery system details configured facilitating endovascular delivery of the heart valve prostheses from peripheral vasculature. Section V describes further embodiments of heart valve prostheses with plate-like bodies with varying connection structures and techniques. Section VI describes heart valve prosthesis embodiments with members adapted to flex to be secured together and to trap valve leaflet components therebetween. Section VII illustrates further heart valve prostheses and delivery systems for treating valve conditions. Section VIII illustrates embodiments of heart valve prosthesis having a ribbon connector.

I. Heart Valve Regurgitation and its Endovascular Treatment

Figure 1B:
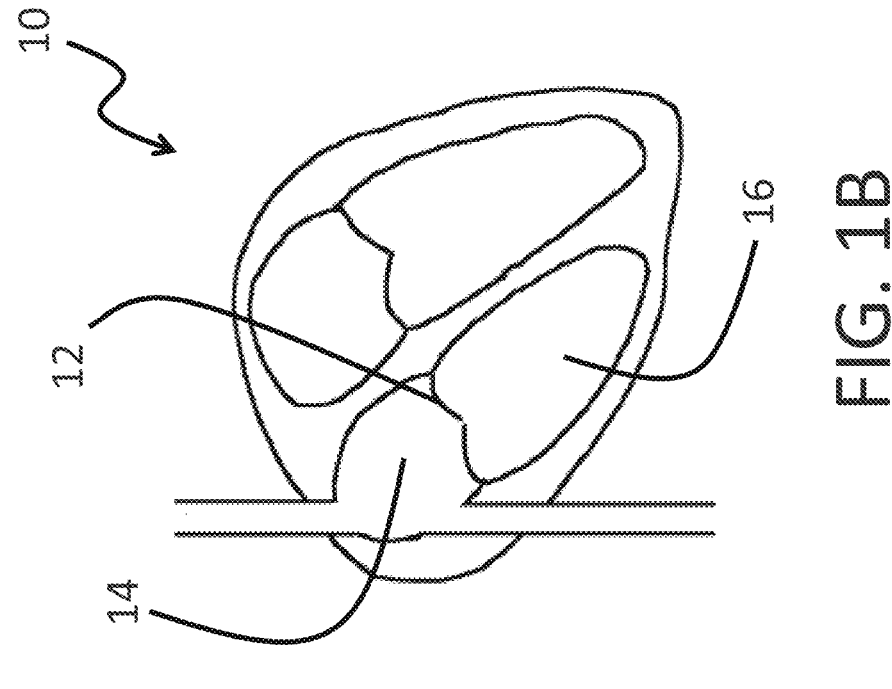
FIG. 1B depicts a cross-sectional view of a heart in normal systole.
Figure 1A:
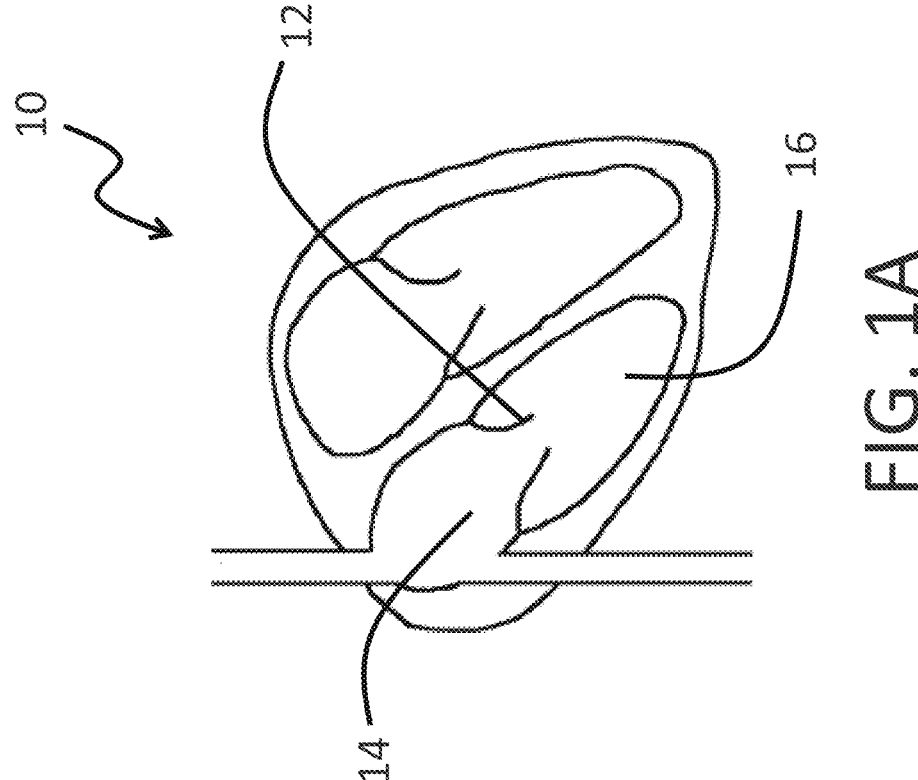
FIG. 1A depicts a cross-sectional view of a heart in normal diastole.
Figure 2A:
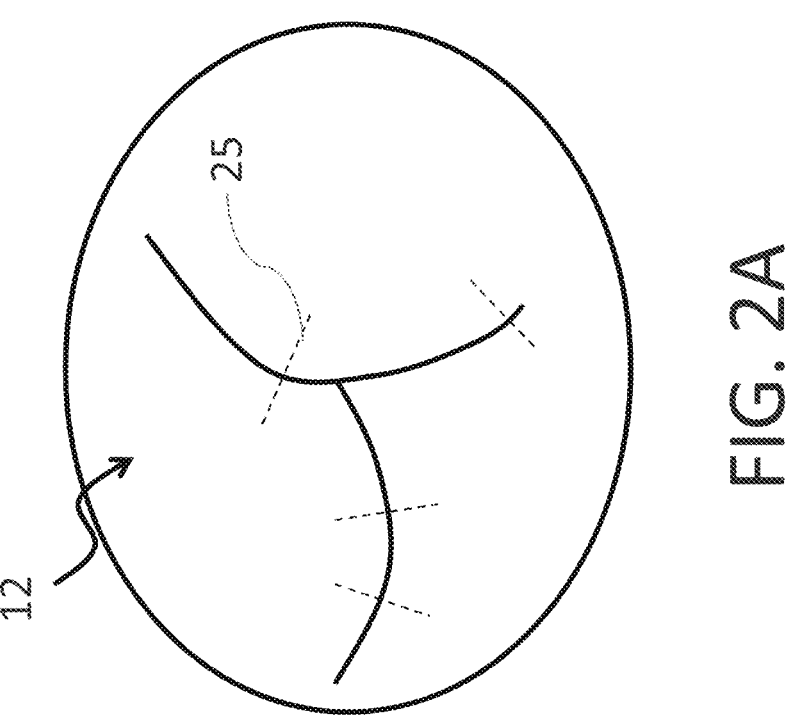
FIG. 2A is a top view of the tricuspid valve of FIG. 2 illustrating a non-limiting selection of locations for placement of devices across the valve leaflets to improve the diseased condition of the valve.
Figure 2:
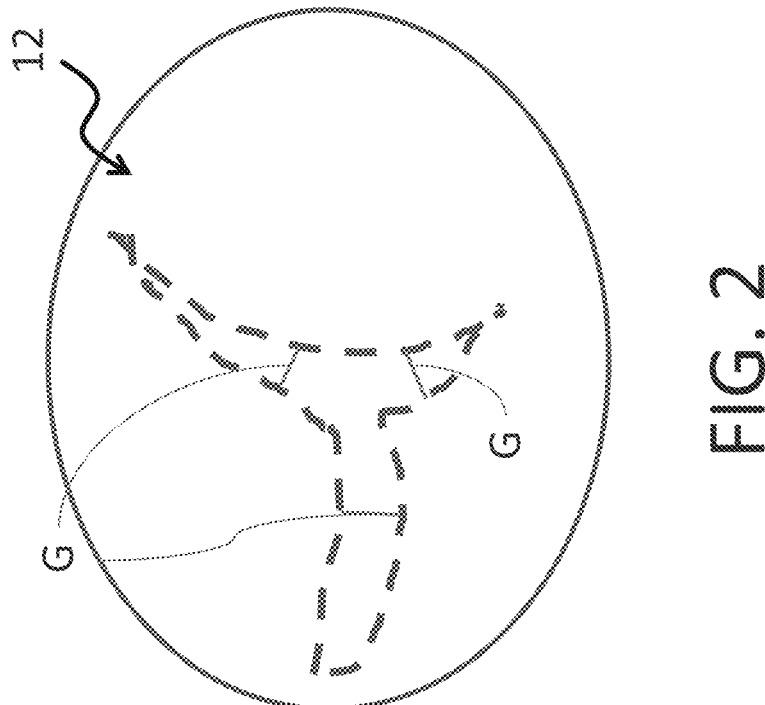
FIG. 2 is a top view of a tricuspid valve of a heart in systole, the valve in need of repair due to poor to no coaptation along the edges of the leaflets.

As discussed above, poor coaptation of valve leaflets is a major problem. FIGS. 1-2A illustrate this problem and a technique for correcting it. FIG. 1A is a schematic representation of a heart 10 in normal diastole. The heart 10 consists of four chambers with the tricuspid valve 12 located between the right atrium 14 and the right ventricle 16. FIG. 1B illustrates the heart 10 in normal systole, showing that the leaflets of the tricuspid valve 12 are contacting where they meet. This leaflet contact seals the right atrium 14 from the right ventricle 16 along the length of the leaflets, sometimes called a line of coaptation.

FIG. 2 schematically illustrates a malfunctioning tricuspid valve 12. This view shows the tricuspid valve from above, e.g., the view from the right atrium. FIG. 2 illustrates that during systole there are large gaps G between the leaflet edges, with a complete lack of coaptation along these leaflets. FIG. 2A illustrates how heart valve prostheses described herein improve the valve function in systole. In this view, four prostheses 25 are coupled with the leaflets of the tricuspid valve. Specifically two prostheses 25 are disposed between two leaflet edges at one of the three lines of coaptation. The other two lines of coaptation are each secured by one prosthesis 25. The prostheses 25 bring together the leaflet edges along at least a portion of the length thereof. The result is that in systole the leaflet edges are substantially closed. Back flow (regurgitation) is reduced or prevented in systole. The leaflets can still separate in diastole sufficiently to allow blood to flow from the right atrium to the left atrium.

The present disclosure may represent a single point fixation between two leaflet edges of either two or three leaflets, or complete edge to edge fixation of the coaptation edges of one or two leaflets, or some combination of these methods. The resulting valve is much more capable of providing healthy blood flow through the heart 10.

II. Heart Valve Repair System

Figure 3:
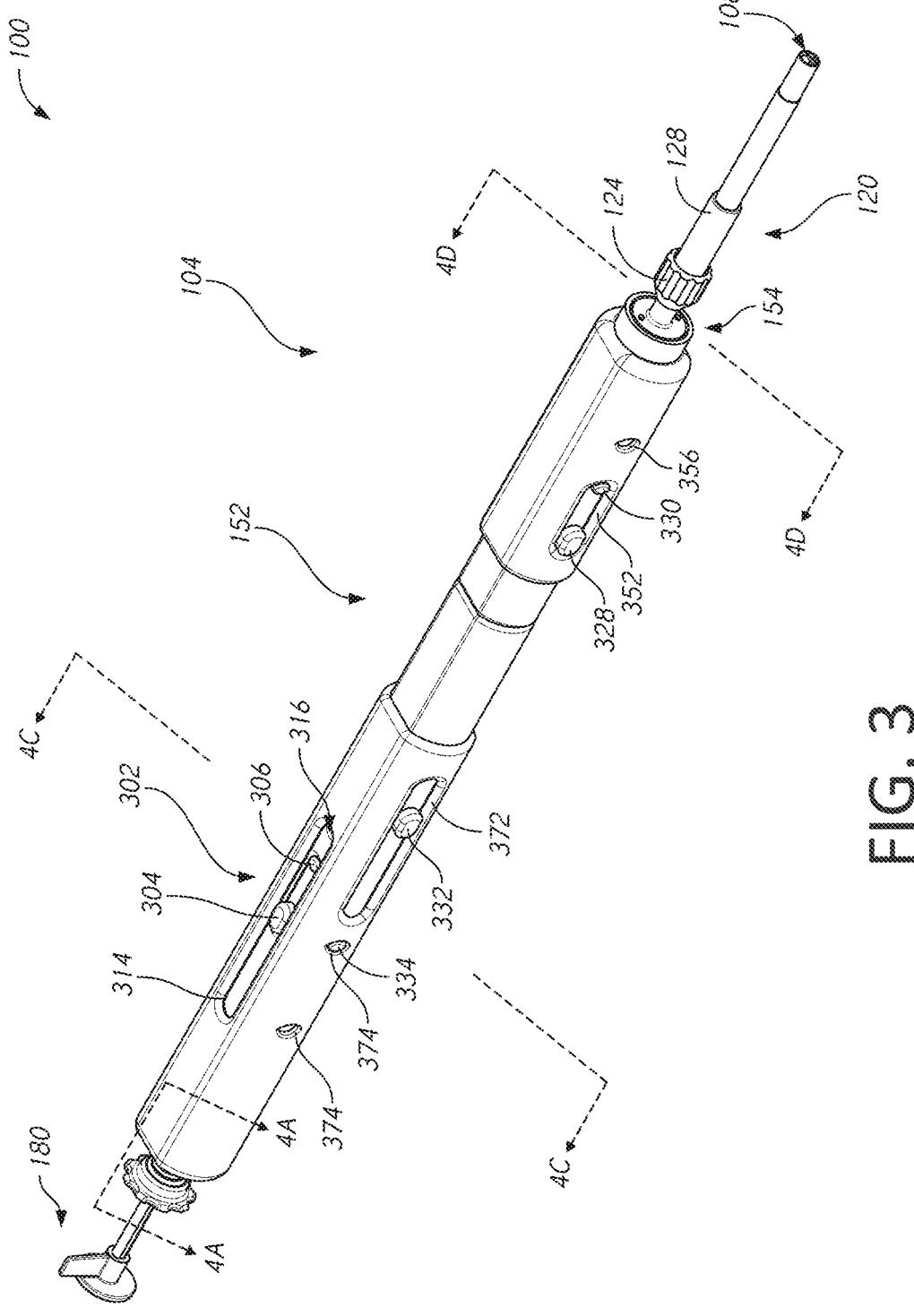
FIG. 3 is a perspective view of one embodiment of a system for heart valve repair.
Figure 4:
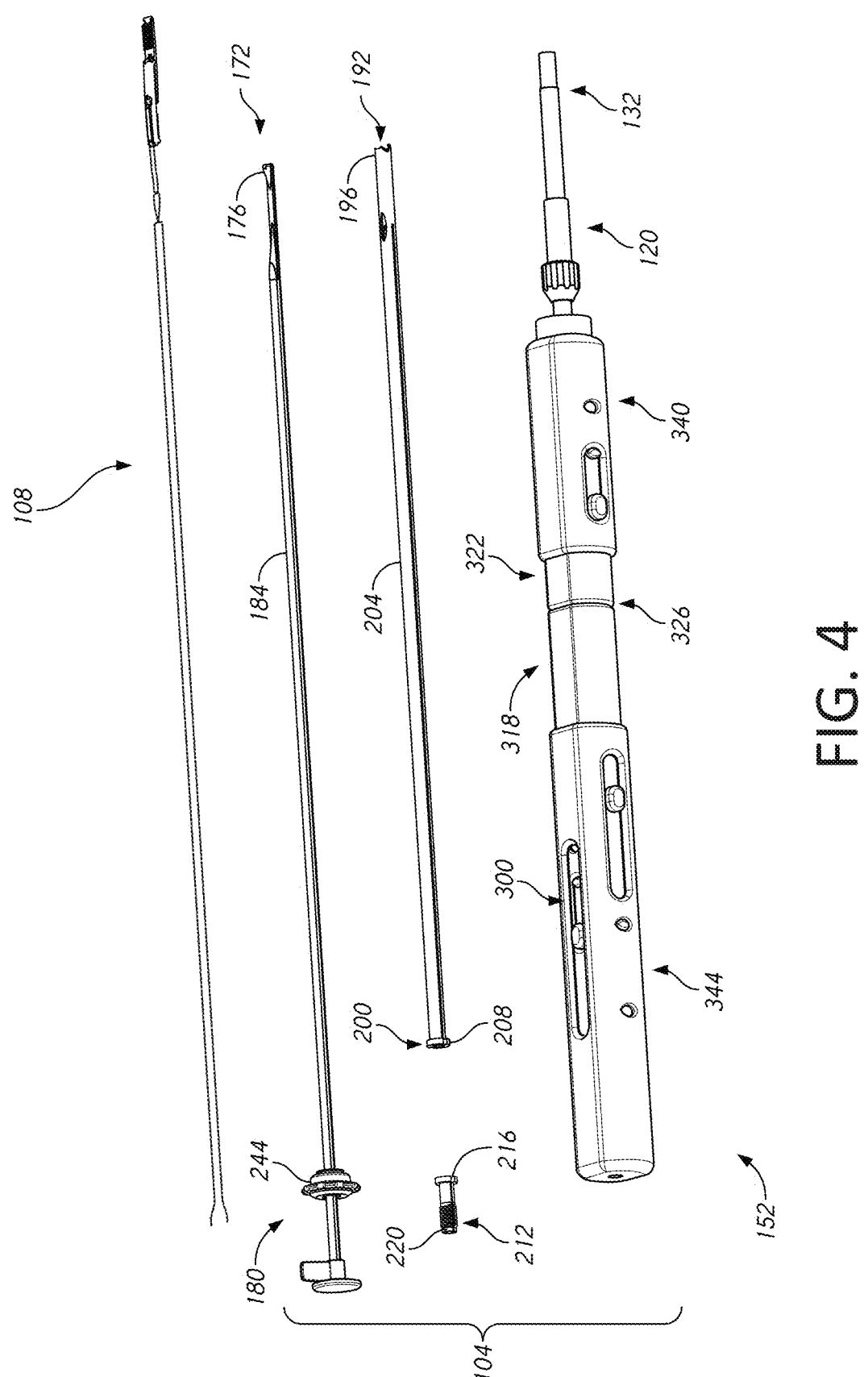
FIG. 4 is an exploded view of the heart valve repair system of FIG. 3.
Figure 4A:
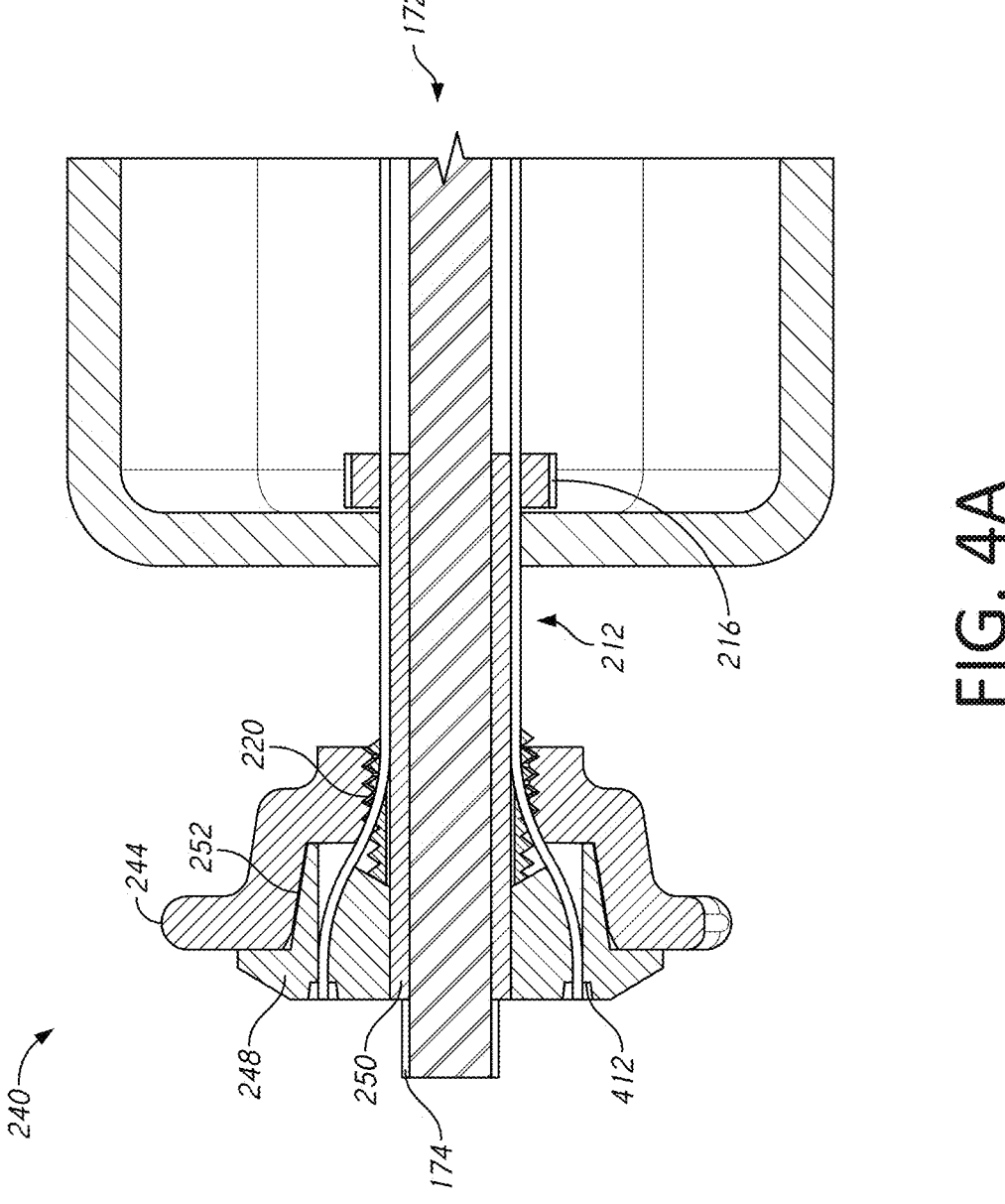
FIG. 4A is a detail view of a suture control assembly.
Figure 4B:
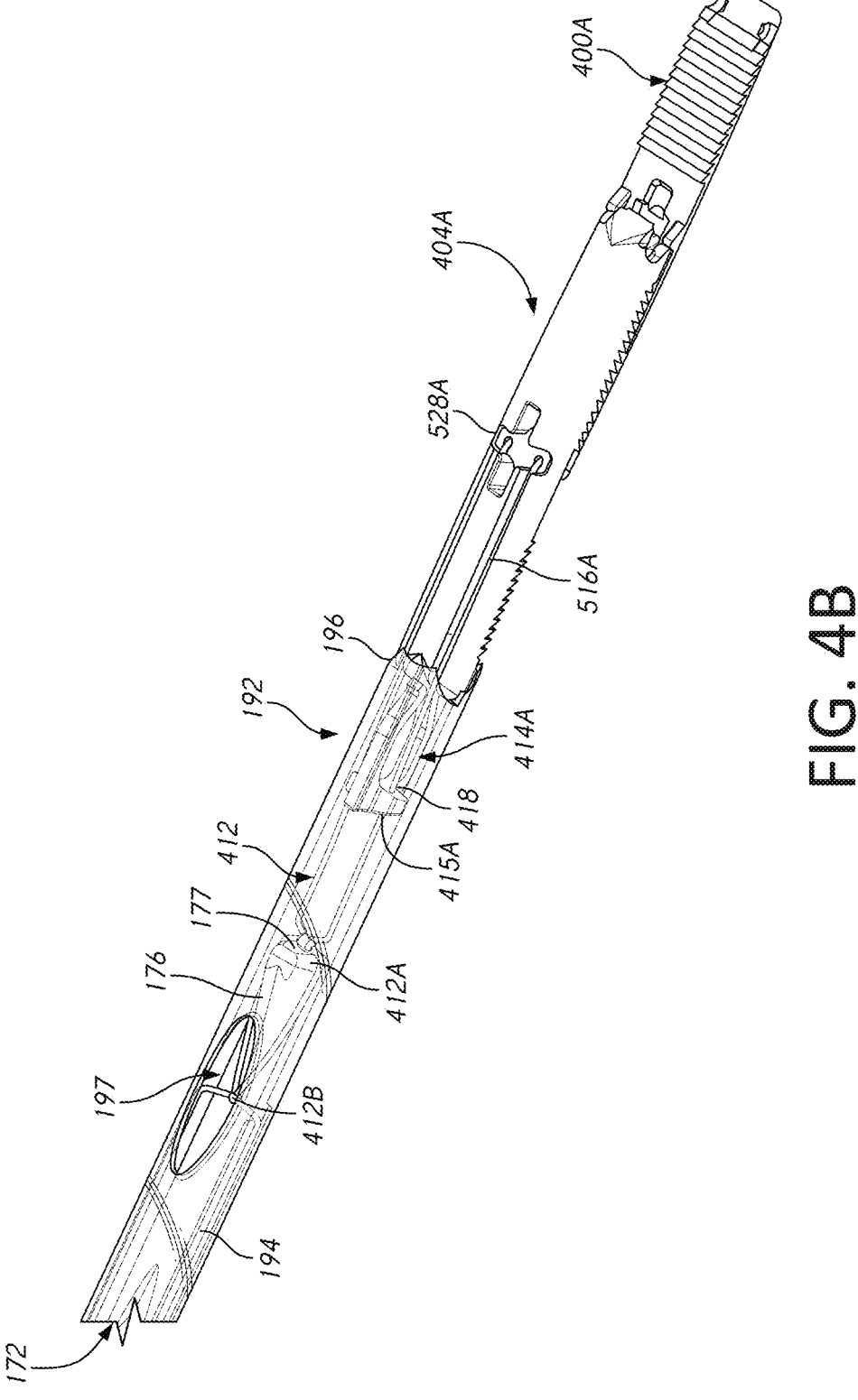
FIG. 4B is a detail view of a suture knot control member.
Figure 4C:
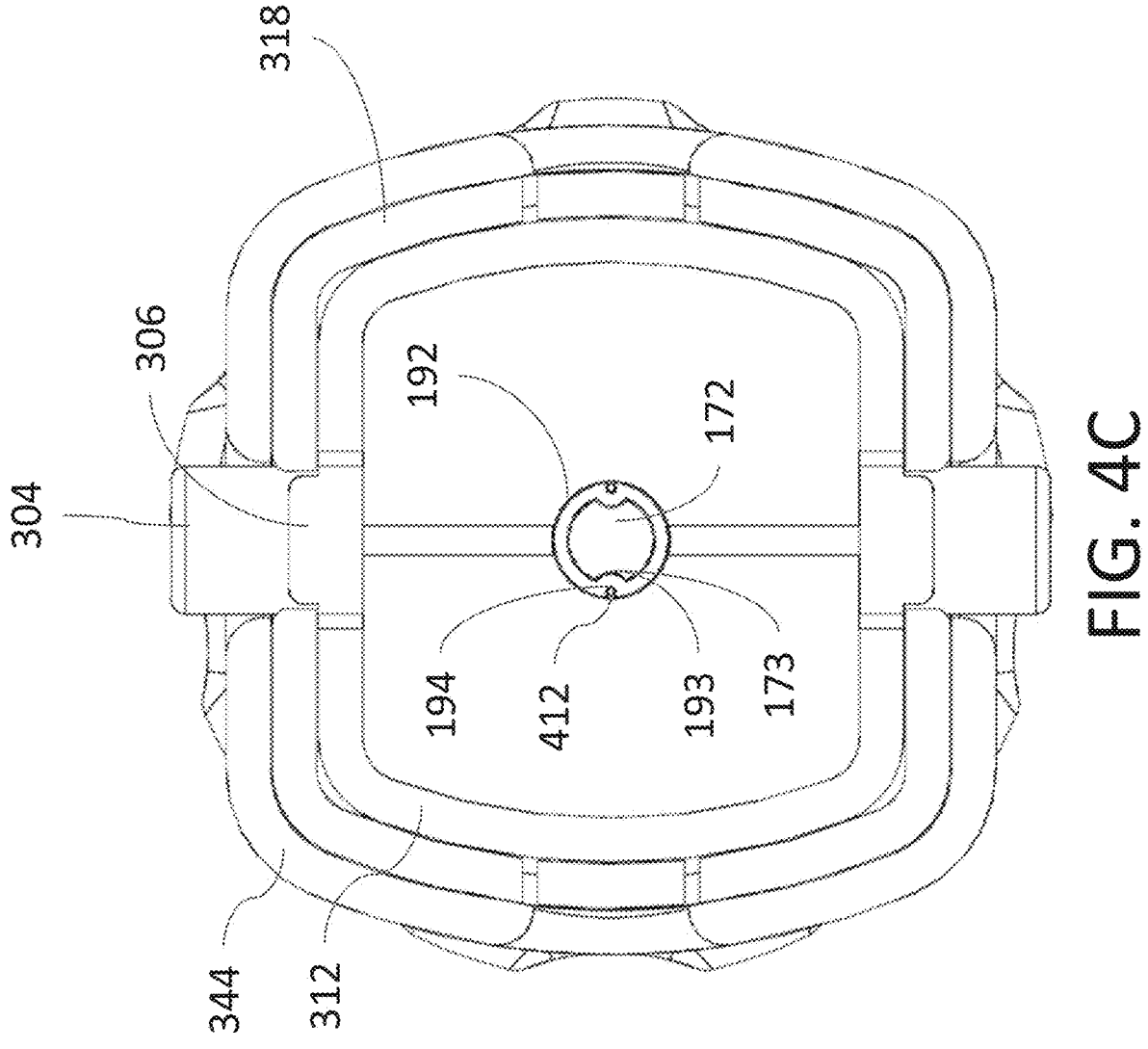
FIG. 4C shows a cross-section taken at section plane 4C-4C in FIG. 3, showing a relationship among control bodies and lengths of a suture according to one embodiment.
Figure 4D:
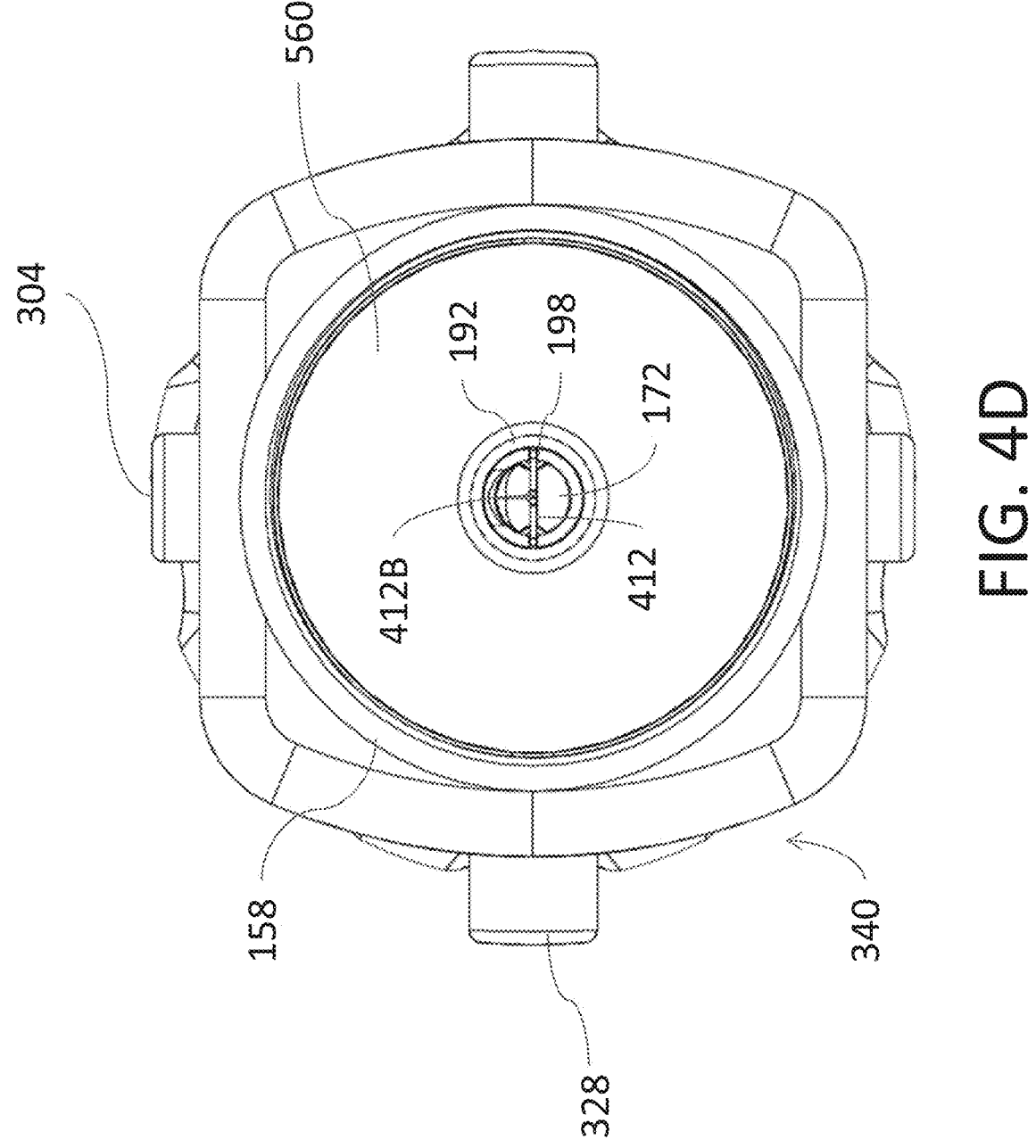
FIG. 4D shows a cross-section taken at section plane 4D-4D in FIG. 3, showing a relationship among control bodies and lengths of a suture according to one embodiment.

FIGS. 3-4D show a heart valve repair system 100 includes a delivery system 104 configured to deliver a heart valve prosthesis 108 to address heart valve regurgitation. The delivery system 104 can deliver and deploy components of the prosthesis 108 separated from each other or unassembled and then assemble these components adjacent to a valve, e.g., inside the heart. When so assembled, components of the prosthesis 108 are disposed on both sides of the valve. In some embodiments, at least one component of the prosthesis spans across the valve. The prosthesis 108 is described in detail below.

The delivery system 104 is adapted for endovascular delivery and deployment of the separate components of the prosthesis. The delivery system 104 can include an introducer 120 and a delivery catheter 132. The introducer 120 can be any conventional introducer for providing a pathway from outside the patient to within the vasculature, e.g., a superficial peripheral blood vessel. The introducer 120 can include a locking hub 124 and a tubular body 128. The delivery catheter 132 can be slideably disposed within the introducer 120. The delivery catheter 132 can be advanced through the proximal end of the introducer 120, and out of the distal end of the tubular body 128. The delivery catheter 132 can be advanced along the peripheral vasculature to the heart. The delivery catheter 132 can have any suitable configuration, and can be a conventional delivery catheter. For example, the delivery catheter 132 can include some or all of the components of the catheter.

Figure 21:
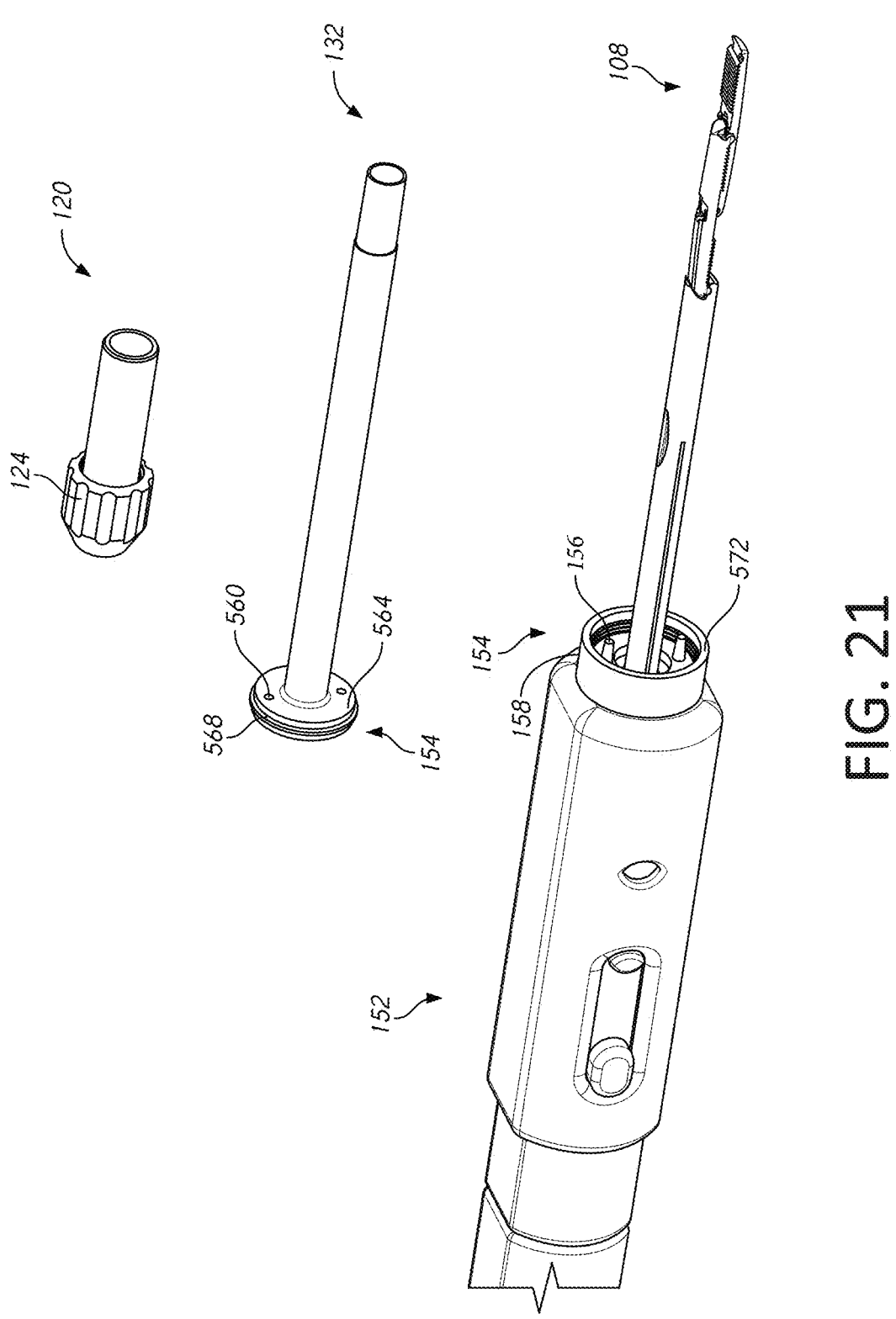
FIG. 21 is an exploded view of a distal portion of the heart valve repair system of FIG. 3.

The delivery system 104 includes an outer housing 152 that can be coupled with the delivery catheter 132. In one embodiment, a coupling assembly 154 is provided on a distal portion of the outer housing 152. The coupling assembly 154 can include a releaseable coupling for connecting with the delivery catheter 132. The coupling assembly is shown in more detail below in FIG. 21.

A plurality of control bodies is disposed in the housing 152 to control components of the heart valve prosthesis 108. The control bodies can include a first elongate member 172 and a second elongate member 192. The first elongate member 172 has a distal end 176 for engaging one or more components of the prosthesis 108 and a second end 180 configured to be manipulated by a user to remotely manipulate the prosthesis components. A middle portion 184 of the first elongate member 172 is disposed within the housing 152. The middle portion 184 can include a solid rod that has contours exposed on the outer surfaces thereof to align the proximal member 212 to the second elongate member 192 in fixed rotation. The first elongate member 172 is moveable relative to the outer housing 152. For example, the first elongate member 172 can be shifted distally relative to the delivery catheter 132 to advance one or more components of the prosthesis 108 out of the housing 152.

The second elongate member 192 also is disposed in the housing 152. The second elongate member 192 has a distal portion 196, a proximal portion 200 and a middle portion 204 disposed about the first elongate member 172. The proximal portion 200 is coupled with the housing 152 such that movement of the portion of the housing to which the proximal portion 200 is coupled directly moves the proximal portion 200. The second elongate member 192 can be a rigid body such that movement of the proximal portion 200 simultaneously moves the middle portion 204 and also the distal portion 196. The distal portion 196 is configured to mate with a portion of the prosthesis 108. As discussed further below in connection with FIG. 19, the distal portion 196 has a first contour that can mate with an end portion of one of the separable components of the prosthesis 108. The first contour of the distal portion 196 can mate to a lateral end of a plate body of the prosthesis 108. As discussed further below in connection with FIG. 30, the distal portion 196 has a second contour that can mate with a central portion of one of the separable components of the prosthesis 108. The second contour can mate with a proximal side of the plate body.

In one embodiment, the proximal portion 200 of the second elongate member 192 comprises a hub 208 configured to be secured to the housing 152. The second elongate member 192 can be a tubular body having a lumen disposed therethrough. The lumen can be configured to receive and slideably support the first elongate member 172. The second elongate member 192 comprises a carriage or chassis for slideably supporting the first elongate member 172 over a range of positions relative to the housings 152. The carriage or chassis of the second elongate member 192 is also adapted to provide rotational control to components of the prosthesis 108 during initial deployment of these components to align these component with or transverse to the line of coaptation. FIG. 4C shows one embodiment in which the second elongate member 192 provides support to the first elongate member 172. The second elongate member 192 can be disposed around the first elongate member 172 and can include a tubular structure with one or a plurality of, e.g., two, three, or four inwardly projecting sections or projections 193. The projection 193 can have a convex profile as shown in the cross-section of FIG. 4C. The first elongate member 172 can be a generally solid member having a substantially circular outer periphery in cross-section as shown in FIG. 4C. The outer profile of the first elongate member 172 can have one or a plurality of, e.g., two, or four radially inward sections or recess 173. The recesses 173 can have a concave profile as shown in the cross-section of FIG. 4C. The projections 193 and the recesses 173 can extend over at least the length of the members 172, 192 that are mated. The recesses 173 can extend over a length that is greater than the length of the projections 193 to facilitate the sliding of the first elongate member 172 over a range of positions relative to second elongate member 192 and within and through the housings 152. The recesses 173 and projections 193 help maintain fixed rotation to keep the first elongate member 172 aligned with the suture knots that are pushed distally by the first elongate member 172, as described in more detail below. The recesses 173 and the projections are one example of a keyed engagement between the first elongate member 172 and the second elongate member 192. In other examples the member 172 could have one or more radial projections and the member 192 could have one or more recesses configured to receive the one or more radial projections.

In one embodiment, the second elongate member 192 comprises an elongate body between the distal portion 196 and the proximal portion 200 and also comprises a proximal member 212 that is separate from and is disposed proximally of the proximal portion 200. The proximal member 212 is configured to mate with the housing 152, e.g., by a hub 216. The proximal member 212 is configured to mate with the first elongate member 172. For example, the proximal member 212 can include a lumen disposed between the ends of the member 212 configured to slideably receive the second end 180 of the first elongate member 172.

FIG. 4A shows that in one embodiment, a threaded interface 220 on the proximal member 212 can be configured to mate with a suture control assembly 240. The suture control assembly 240 includes a knob 244 with a threaded interface configured to mate with the threaded interface 220. The suture control assembly 240 also includes a compressible locking component 248 disposed in the knob 244. The compressible locking component 248 can include a lumen configured to receive the proximal member 212. The locking component can be disposed between the hub 216 and the threaded interface 220. Advancement of the knob 244 away from the hub 216 causes compression of the locking component 248. The locking component 248 has one or a plurality, e.g., two, suture threads disposed through lumens formed therein. A result of the compression of the locking components 248 is the impingement of the walls of these lumens on the suture threads holding them in place and/or retaining tension of the suture threads between the suture control assembly 240 and the components of the prosthesis 108 at the distal portion of the system 100. The locking component can and the proximal member can be mated with an outside surface of the elongate member 172. In one embodiment, one or two or a plurality of channels 174 can be formed in an outer surface of the elongate member 172. The channels can be deep enough to receive a control portion, projection or flange of a component disposed about the elongate member 172 which is desired to be rotationally linked to the elongate member 172. For example, the locking component 248 has a control flange 250 disposed in each of two opposed channels 174 on the elongate member 172. The control flange 250 prevents the locking component from rotating as the knob 244 is rotated around the elongate member 172. This results in advancement of the knob 244 over the locking component 248. As a result, a wedge interface 252 is subject to increased compression which clamps a suture 412 (discussed further below).

The outer housing 152 has a number of configurations in which the components thereof are disposed at different relative positions. The housing 152 comprises a first internal shell 300 having a proximal end and a distal end. The proximal end comprise a face disposed transverse to a longitudinal axis of the housing 152. The face at the proximal end of the first internal shell 300 comprises an aperture therethrough. The second elongate member 192 is disposed through the aperture. The hub 208 of the proximal portion 200 is mated with the face at the proximal end of the first internal shell 300. As a result, movement of the first internal shell 300 proximally and distally moves the second elongate member 192.

The outer housing 152 includes a second inner shell 312 that is disposed around the first inner shell 300. The second inner shell 312 has proximal end and a distal end. The proximal end of the second shell 312 has a proximal face with an aperture through which the first elongate member 172 is slideably disposed. The first elongate member 172 can be moved independently of the second inner shell 312. The first inner shell 300 can be selectively secured to the second inner shell 312 by a suitable mechanism. For example, a latch mechanism 302 can be provided to engage the shells in 300, 312 one of a plurality of positions. The second inner shell 312 can include an elongate slot 314 disposed therein. An actuator 304 of the latch 302 can travel in the slot 314 between a fully forward position in which a distal face of the actuator 304 touches the distal end of the slot 314 and a fully retracted position in which the actuator 304 touches a proximal end of the slot 314. In one embodiment, the latch 302 provides a locked position, which can be provided between the proximal and distal ends of the slot 314. In one embodiment, the actuator 304 is disposed on an elongate flexing member. The elongate flexing member has a free end adjacent to the actuator 304 and a fixed end. The fixed end is fixed to a remaining portion of the first inner shell 300. A locking feature 306 is disposed on the flexing member between the fixed and free ends. The locking feature 306 can slide in the slot 314 when the locking feature is at or proximal of the distal end of the slot 314. The locking feature 306 can be moved distal of the distal end of the slot 314 until reaching an aperture 316 in the second inner shell 312. Once the locking feature 306 reaches the aperture 316 the elongate flexing member resiliently deflects toward the second inner shell 312 moving the locking feature 306 into the aperture. When locked, the first inner shell 300 is secured to the second inner shell 312. Movement of the second inner shell 312 moves the first inner shell 300. Because the second elongate member 192 is secured to the first inner shell 300 movement of the second inner shell 312 results in movement of the second elongate member 192 and in corresponding movement of components of the prostheses 108.

The locking feature 306 can be removed from the aperture 316 in the second inner shell 312 by pressing the actuator 304. When so removed, the first inner shell 300 can be shifted to a further distal position in which the actuator 304 is at the distal end of the slot 314. This results in positioning the distal end 176 distal of the second elongate member 172 to be of the distal end of the delivery catheter 132 as discussed below.

In one embodiment, the second inner shell 312 has a proximal portion 318 and a distal portion 322 that are coupled at a joint 326. FIGS. 3 and 4 show that the distal portion 322 of the shell 312 is at least partially disposed inside a first outer shell 340 and the proximal portion 318 is at least partially disposed in a second outer shell 344. The second inner shell 312 is capable of simultaneous and of relative movement to one or both of the first and second outer shells 340, 344.

In one embodiment, the first outer shell 340 has an elongate slot 352 and an aperture 356. The second inner shell 312 has an actuator 328 and a locking feature 330. The actuator 328 and the locking feature 330 are disposed on an elongate flexing member. By pressing the actuator 328 the locking feature can move inward of the first outer shell 340 such that the first outer shell 340 can be moved proximally from the position shown in FIG. 3 until the locking feature 330 is aligned with the aperture 356. Releasing the actuator 328 allows the locking feature 330 to move away from the center of the housing 152 such that the locking feature 330 is secured in the aperture 356. The motion of the inner shell 312 forward relative to the first outer shell causes the delivery catheter 132 to be withdrawn relative to the components of the prosthesis 108, e.g., causing a distal member of the prosthesis 108 to be fully exposed outside of the delivery catheter. When so exposed, the distal member can be allowed to rotate from a lower profile delivery orientation to a deployed orientation in which leaflets can be engaged as discussed further in connection with FIG. 23.

Relative motion can be selectively provided between the second inner shell 344 and the second outer shell 340. FIG. 3 shows that the second outer shell 344 includes an elongate slot 372 and a plurality of apertures 374, e.g., a proximal aperture and a distal aperture. The second inner shell 312 includes an actuator 332 and a locking feature 334. A first relative position can be provided between the second inner shell 312 and the second outer shell 344 is shown in FIG. 3. In this relative position the locking feature 334 is disposed in the distal-most aperture of the plurality of apertures 374. The actuator 332 is spaced from both ends of the slot 372. An extended position of the second inner shell 312 relative to the second outer shell 344 is provided if the actuator 332 is depressed such that the locking feature 334 can be moved inward of the second outer shell 344 out of the aperture 374. Relative motion can shift the second inner shell 312 distally relative to the second outer shell 344. This movement can continue until the actuator 332 is disposed adjacent to the distal end of the slot 372. In this position the locking feature 334 is also in the slot 372 adjacent to the proximal end thereof. A third position of the second inner shell 312 relative to the second outer shell 344 can be provided by depressing the actuator 332 such that the locking feature 334 can be moved inward of the second outer shell 344 out of the aperture 374, as illustrated in FIG. 3.

Relative motion can shift the second inner shell 312 proximally relative to the second outer shell 344. This movement can continue until the actuator 332 is disposed adjacent to the proximal end of the slot 372. In this position the locking feature 334 is disposed at the proximal aperture 374. Releasing the actuator 332 allows the resilient member upon which the actuator 332 and the locking feature 334 are disposed to move outward such that the locking feature 334 is within the aperture of the second outer shell 344.

Further details of the delivery system 104 will be understood in connection with FIGS. 19-30 which show aspects of methods of deploying the prostheses 108.

III. Heart Valve Prosthesis

Figure 5:
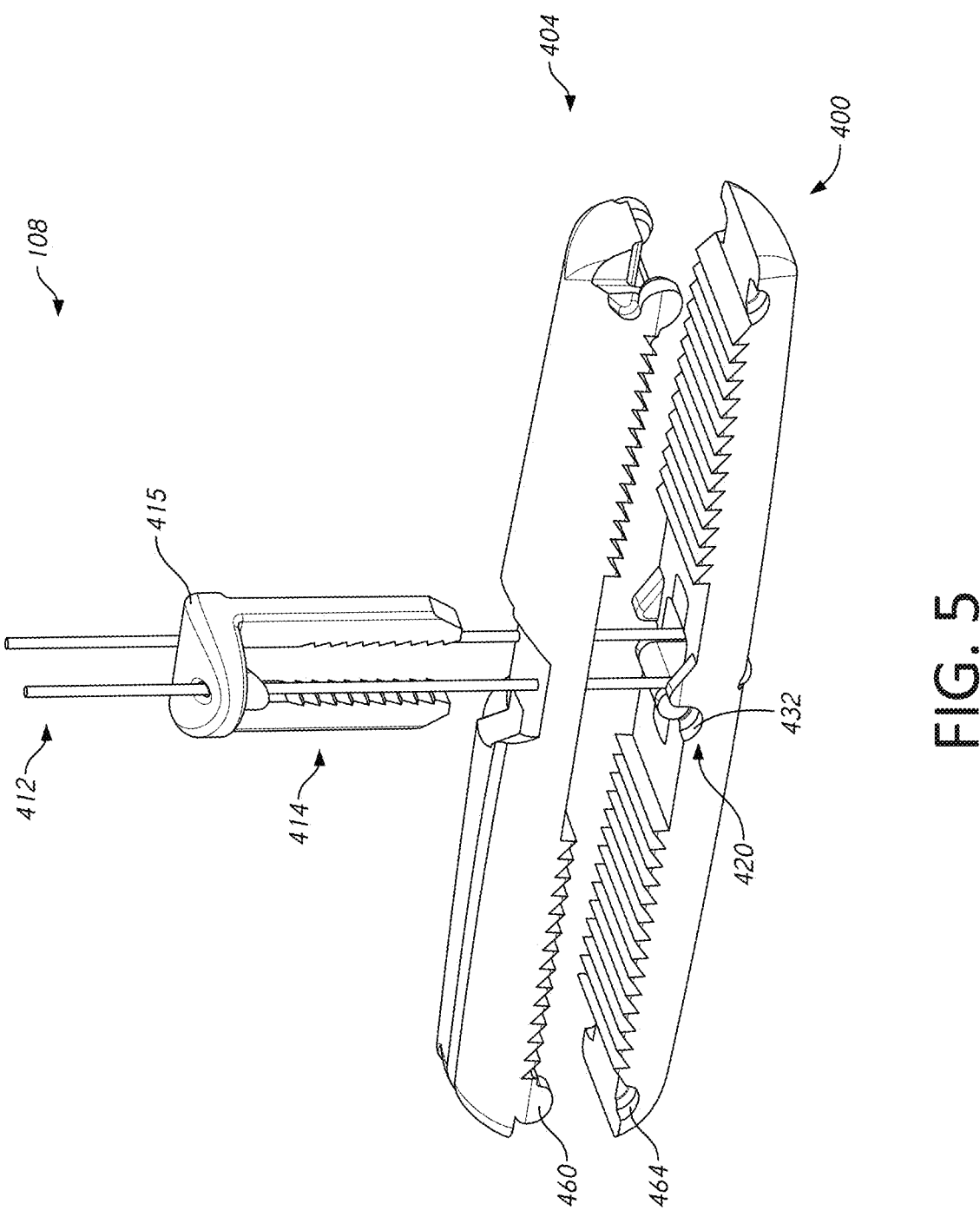
FIG. 5 is a perspective exploded view of one embodiment of a heart valve prosthesis.
Figure 7:
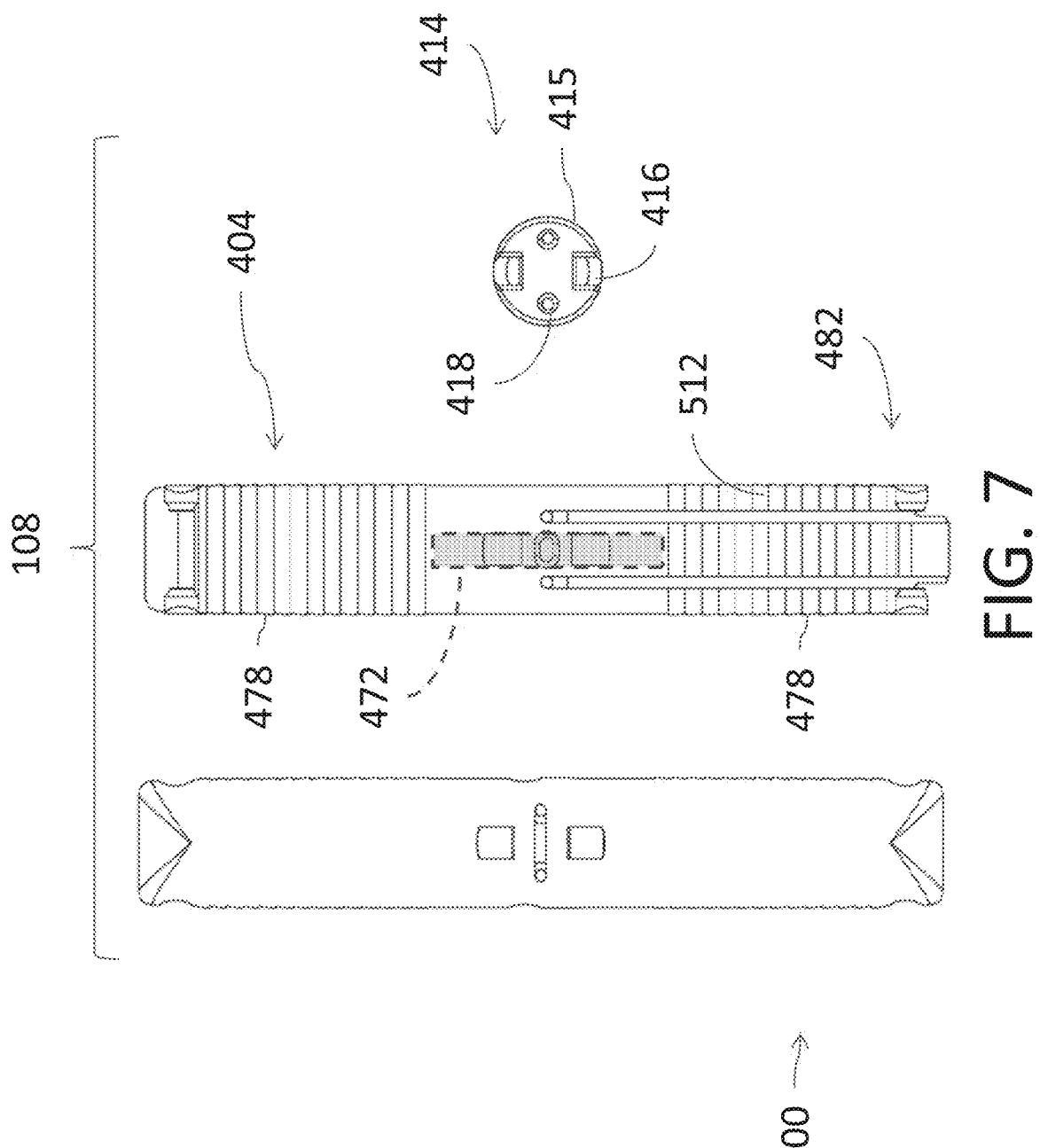
FIG. 7 is an exploded distal side view of a distal member, a proximal member, and a clip of the embodiment of FIG. 5.
Figure 8:
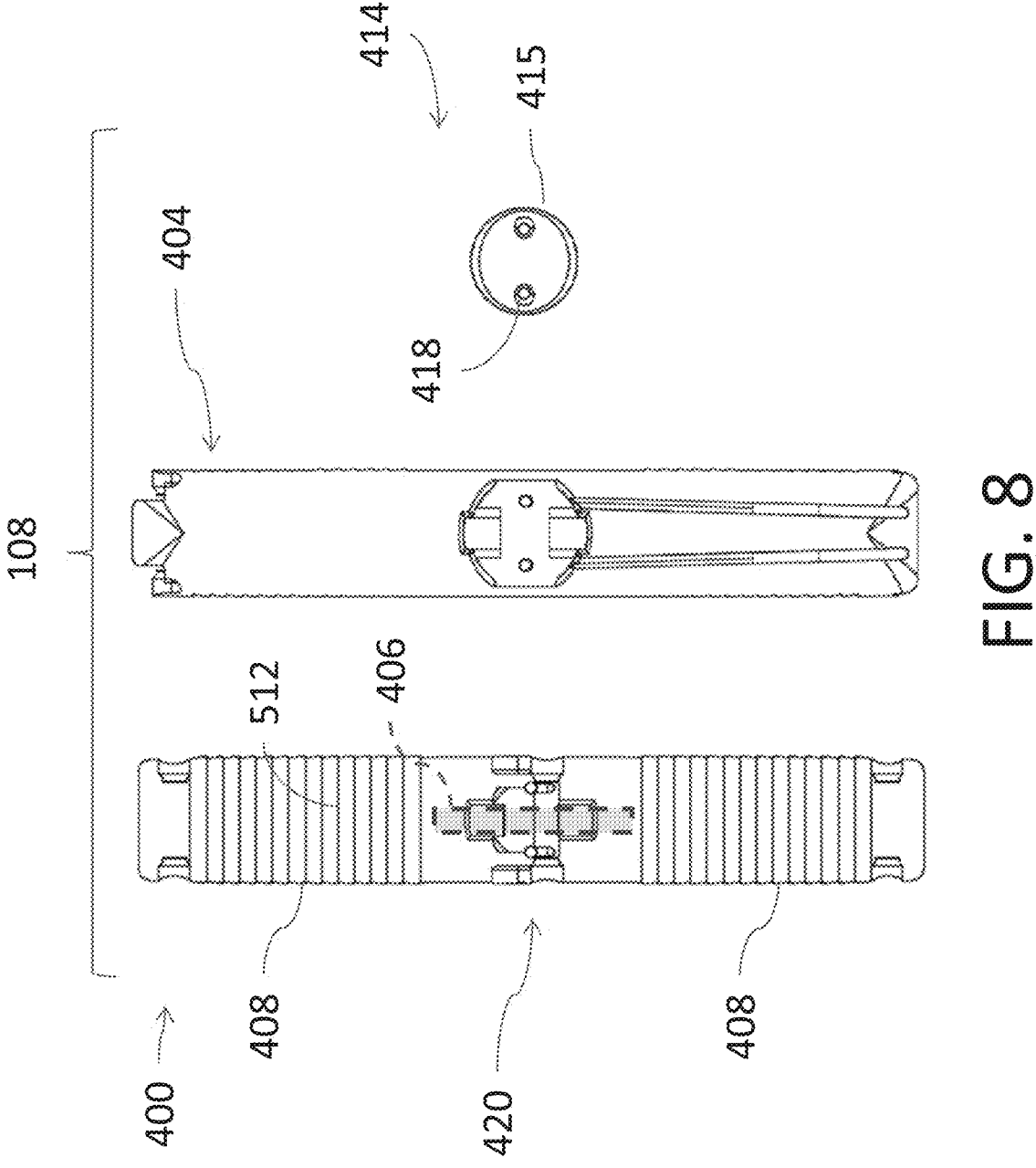
FIG. 8 is an exploded proximal side view similar to FIG. 7.
Figure 25:
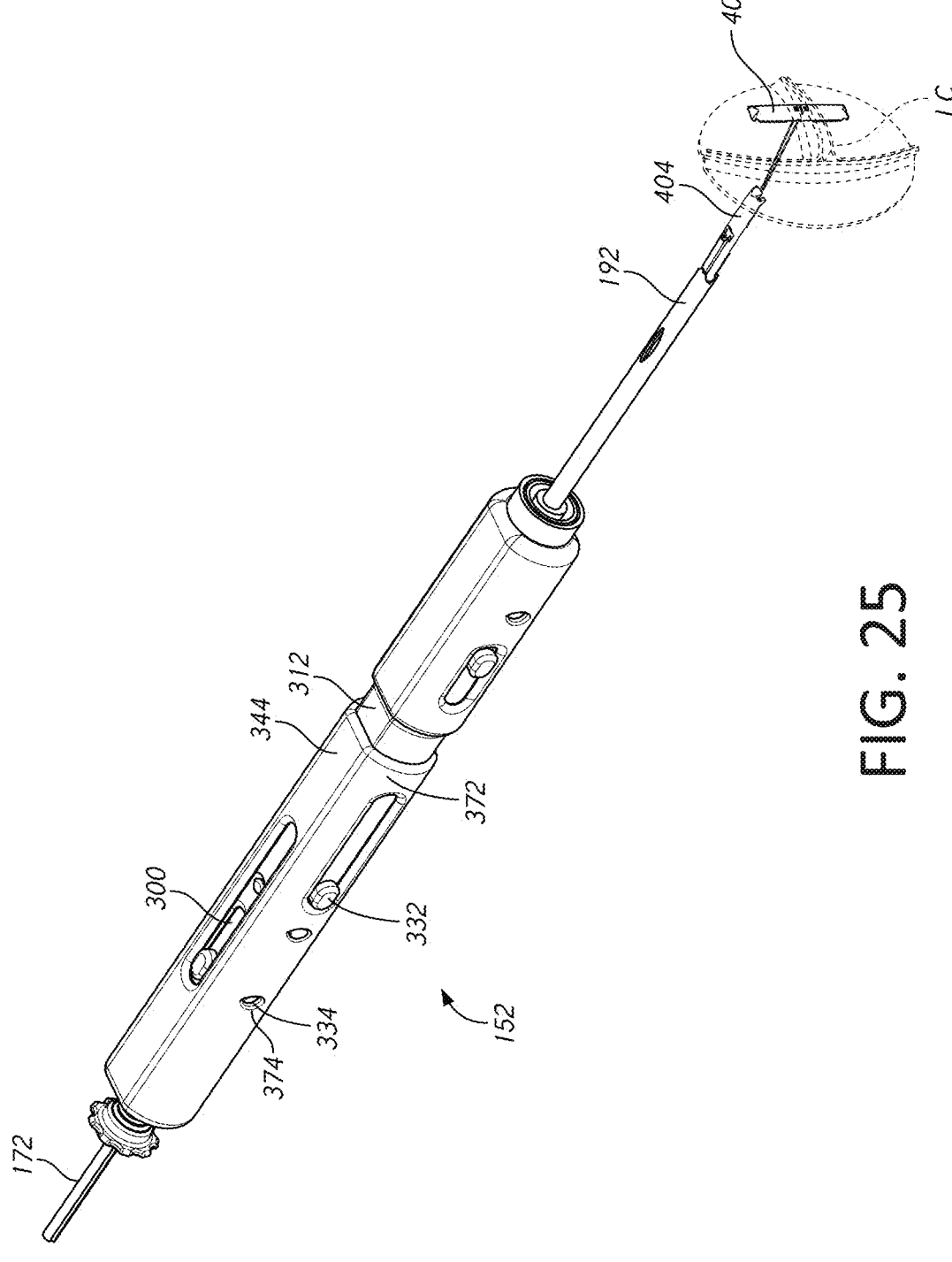
FIG. 25 shows a stage of a method following the stage of FIG. 23 in which the delivery system shown in FIG. 3 is withdrawn from the tricuspid valve providing clearance between a distal end of the delivery system and the distal member.

FIGS. 5-20 show various feature of one embodiment of the heart valve prosthesis 108 described and claimed herein. FIG. 5 shows that the prosthesis 108 can include a first member 400 and a second member 404 to be placed on distal and proximal sides of the valve leaflets respectively. FIG. 8 shows that the first member 400 comprises a first central portion 406. FIG. 25 shows that the central portion 406 can be disposed adjacent to a line of coaptation Lc on a first (distal) side of two adjacent heart leaflets. Peripheral portions 408 of the first member 400 are adapted to be placed into direct contact with the two adjacent heart leaflets.

Figure 6:
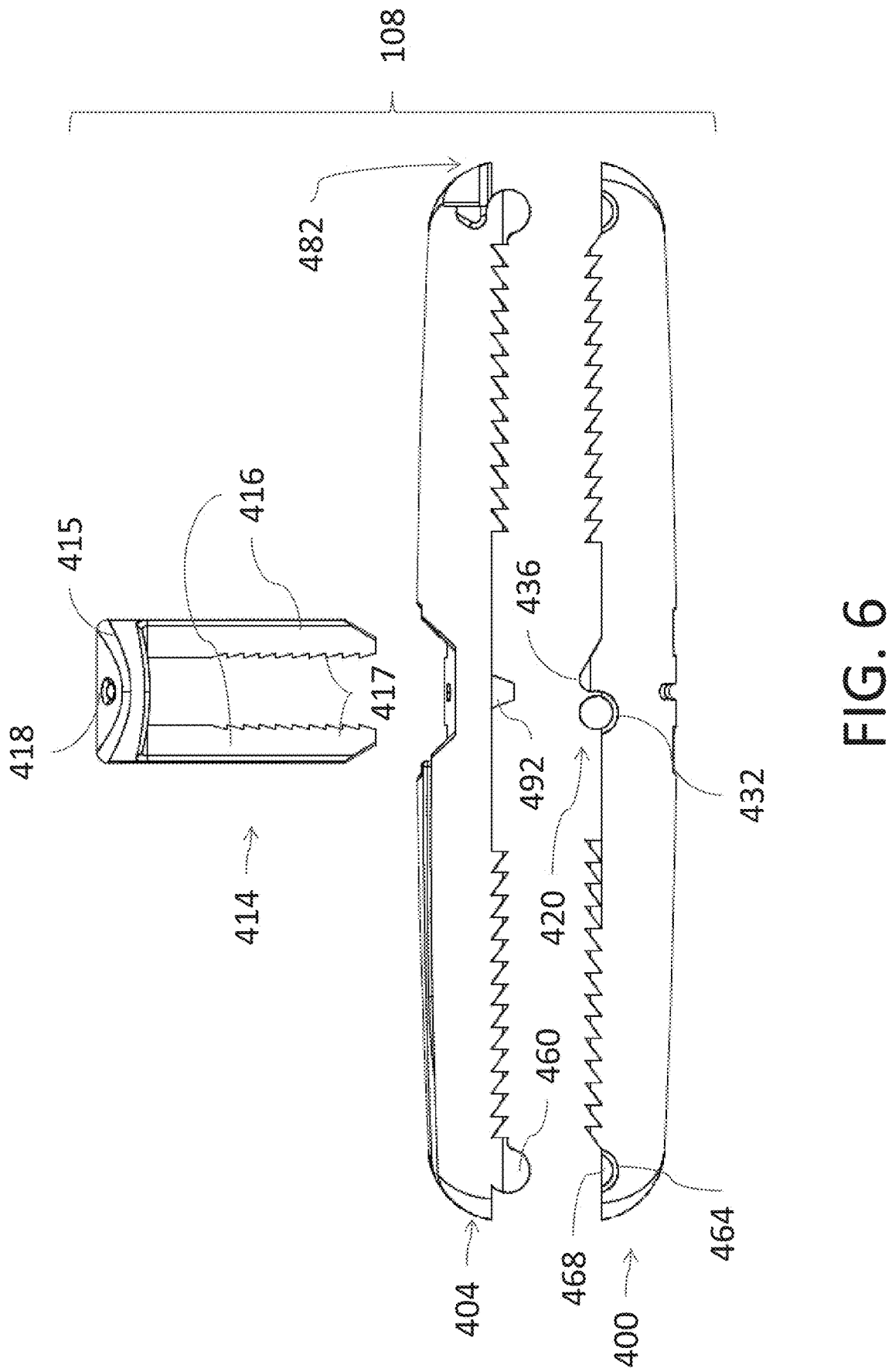
FIG. 6 is an exploded view similar to FIG. 5 with a suture removed for clarity.

The first and second members 400, 404 can be coupled in a suitable manner. In various embodiments the prosthesis 108 includes one or both of a suture 412 and a connector 414. The connector 414 has a locking portion at a first end and a connector body 415 at a second end. The connector body 415 can be at the proximal end of the connector 414. The connector 414 is a generally solid body that can function like a clip. In variations discussed further below a connector in the form of a tension member, e.g., a wire, can be used to connect the first and second members 400, 404 together in the heart in a leaflet securing assembly. The description of the first and second members 400, 404 can be combined with the description of a heart valve prosthesis 790 and with the description of systems and methods of delivering and assembling the prosthesis 790 in the heart, as set forth in connection with FIGS. 44-60. FIG. 6 shows that the locking portion can comprise one or a plurality of, e.g., two, members 416 projecting from the connector body 415. The members 416 can be adapted for insertion in or across one or both of the first and second members 400, 404. In one embodiment, the members 416 are resilient and can expand away from each other upon insertion, storing strain energy. Upon full insertion the strain energy can cause a normal or compressive force to be applied to the one or both of the first and second members 400, 404 as discussed further below. In some embodiments, the members 416 include barbs 417 to engaged mating barbs on one or both of the first and second members 400, 404. In other embodiments illustrated by FIG. 4B and by FIGS. 42, and 43 discussed below the members connector 414 can be modified such that the members 416 are elastically deformable to engage one or both of the first and second members 400A, 404A.

Figure 17:
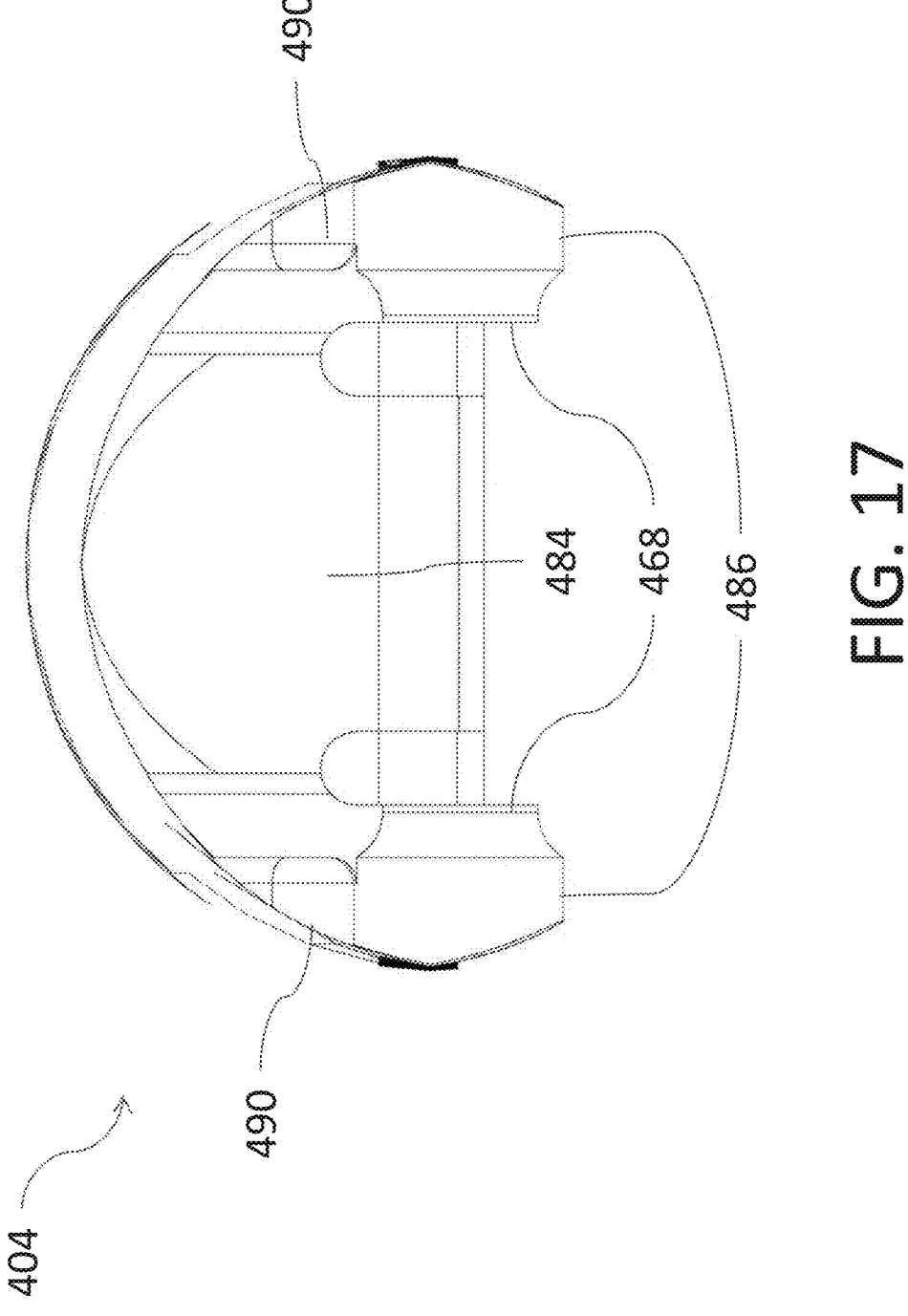
FIG. 17 is a first end view of the proximal member of FIG. 13.
Figure 18:
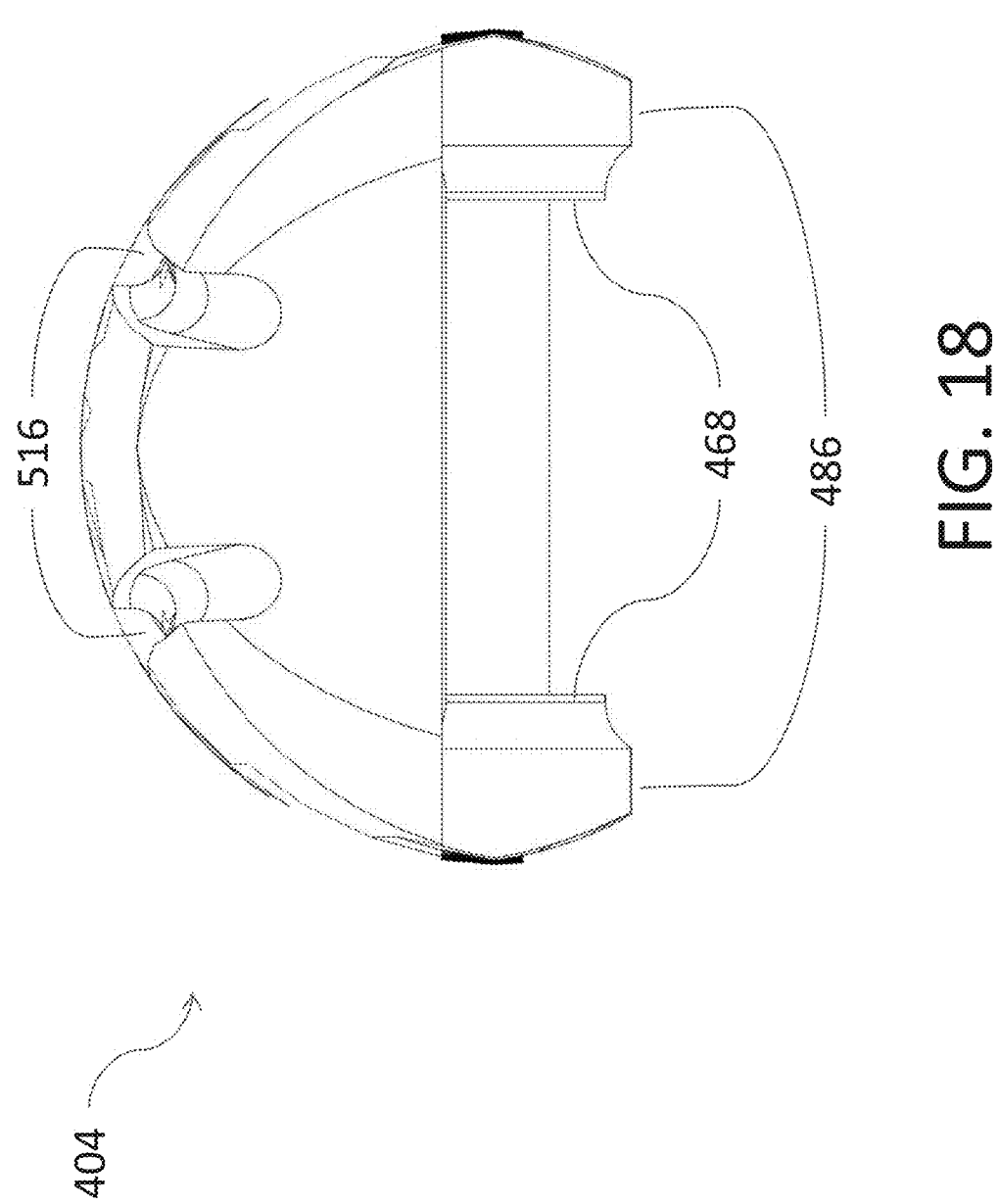
FIG. 18 is a second end view of the proximal member of FIG. 13.

The connector body 415 can have any suitable configuration. In one embodiment, the connector body 415 is contoured to match the shape of a surface of the first or second member 400, 404 adjacent to which the connector body 415 is disposed when the prosthesis 108 is fully assembled. For example, if the second member 404 is a proximal member and the connector body 415 is inserted from the proximal side of the proximal member 404 the connector body 415 will come to rest adjacent to the proximal side of the proximal member 404. If the proximal side of the proximal member 404 has curvature, as illustrated in FIGS. 17 and 18 the surface of the connector body 415 disposed away from the members 416 can have the same or a similar curvature. By providing the same or a similar curvature, discontinuity of shape along the proximal side of the prosthesis 108 can be reduced or eliminated such that discontinuities and crevices to which the blood flowing around the deployed prosthesis 108 would be exposed will be reduced or eliminated.

Figure 9:
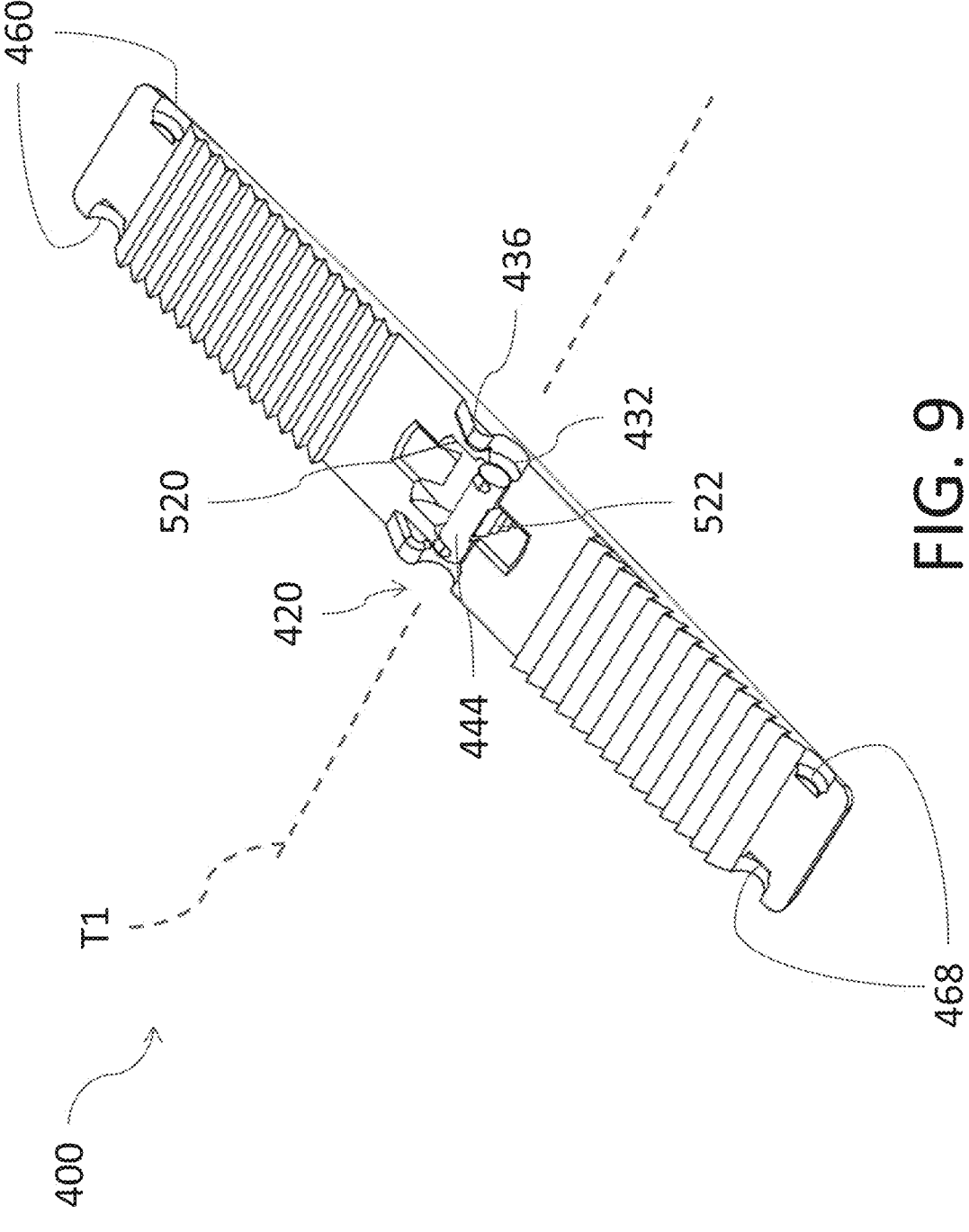
FIG. 9 is a perspective view of a proximal side of one embodiment of a distal member of the heart valve prosthesis of FIG. 4.

FIGS. 5 and 6 shows that the first member 400 also has a first hinge portion 420. The first hinge portion 420 can comprise features that allow for the first member 400 to pivot relative to or on the second member 404 from the low profile state within the delivery system 104 to an orientation to span the facing edges of adjacent valve leaflets or line of coaptation. FIG. 9 shows that the first hinge portion 420 at least partially surrounds, e.g., is intersected by, a first transverse axis T1. The first hinge portion 420 can include a concave surface 432. The concave surface 432 can be partly extended to a protrusion 436 that extends from the tissue facing side of the first member 400. The protrusion 436 helps with the functioning of the first hinge portion 420 by providing a counteracting force to the tension that is applied to the suture 412 when the prosthesis 108 is in the low-profile arrangement. This counteracting force keeps the first and second members 400, 404 from separating from one another when the first and second members 400, 404 are in the low-profile arrangement. The first hinge portion 420 can include a pocket 438 (see FIG. 12) that is recessed in the first member 400. The pocket 438 can be recessed from the tissue facing surface to a greater extent than the depth of the curved surface 432. The pocket 438 can provide clearance during deployment for a portion of the second member 404, as discussed further below. The protrusion 436 and the pocket 438 provide a role in stabilizing the second member 404 on the first member 400 during the process of deploying the prosthesis 108 as discussed below.

Figure 10:
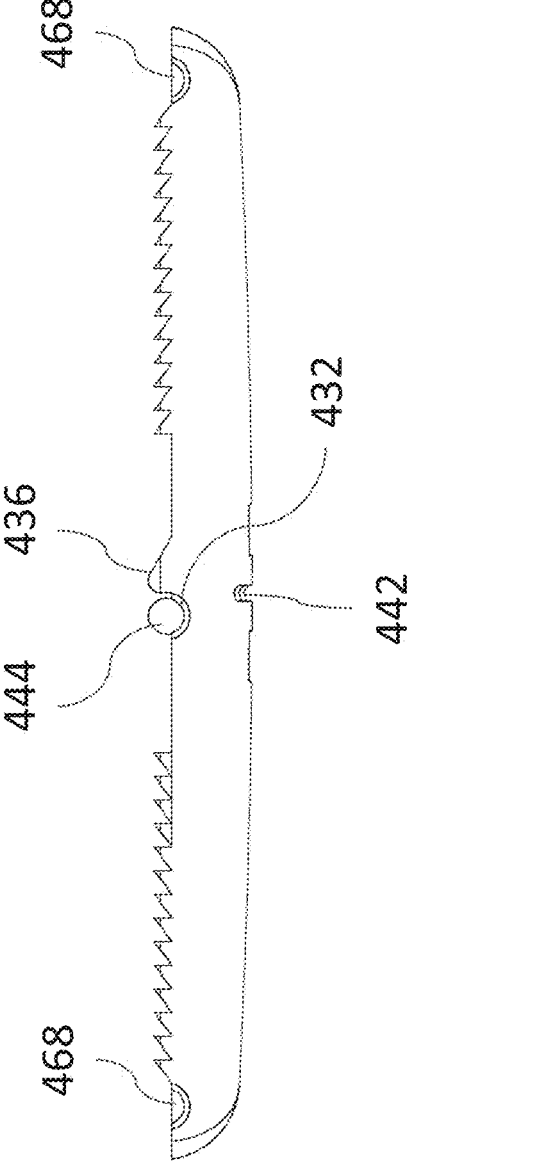
FIG. 10 is a side view of the distal member of FIG. 9.
Figure 11:
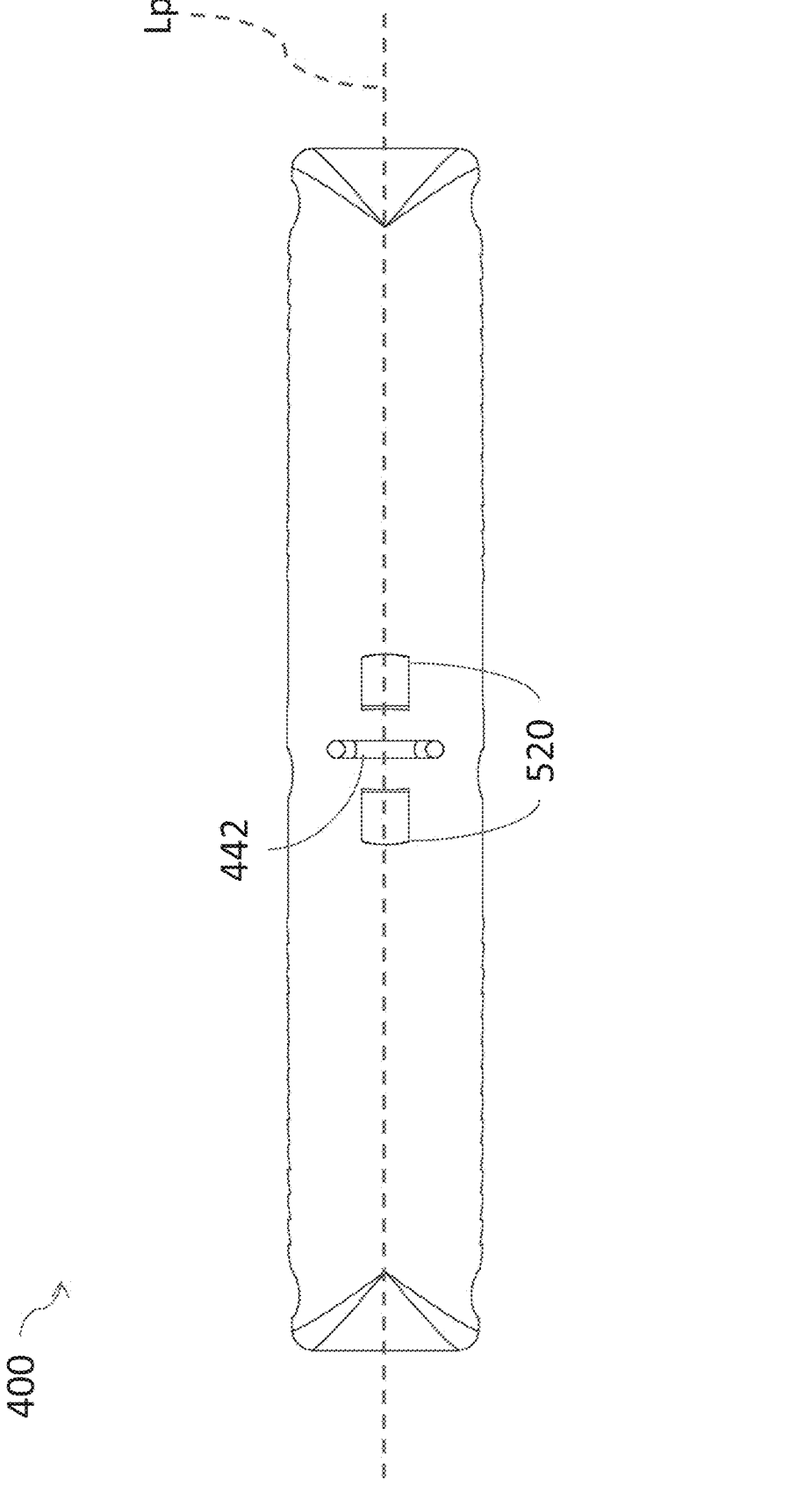
FIG. 11 is a distal side of the distal member of FIG. 9.
Figure 12:
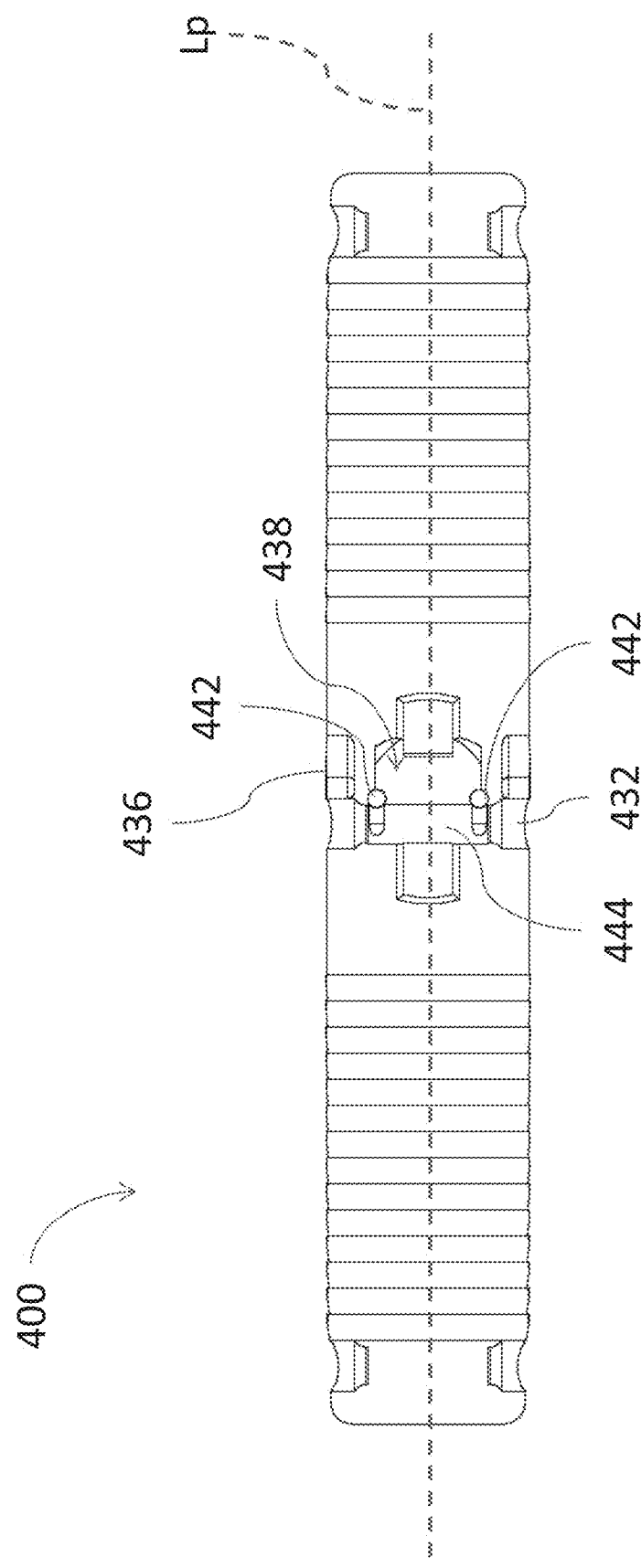
FIG. 12 is a proximal side of the distal member of FIG. 9.

A suture channel 442 can be provided through the first member 400. The suture channel 442 can allow the suture 412 to pass through and/or be secured to the first member 400. FIG. 12 shows that a portion of the suture channel 442 passes through the first member 400 from the tissue facing side thereof to the side opposite the tissue facing side. The suture channel 442 can include a plurality of segments that pass through the first member 400. FIG. 12 shows that the suture channel 442 can extend through the first member in two locations spaced away from a central longitudinal plane Lp. FIG. 11 shows that the suture channel 442 can extend across the longitudinal plane Lp on the side of the first member 400 opposite the tissue engaging side. FIG. 10 shows that the portion of the suture channel 442 on the opposite side of the first member 400 is recessed into the opposite side such that the suture 412 is at least partially protected for the span traversing the plane Lp. The suture channel 442 can comprise one or more through-holes formed in the first member 400. In one embodiment, a cylindrical hub surface 444 forming part of the first hinge portion 420 is provided in the central portion 406 and is centered the transverse axis T1. The cylindrical hub surface 444 rotates about the axis T1. The suture channel 442 can comprise a suture channel segment recessed into the cylindrical hub surface 444. When the first member 400 is in a low profile state in the delivery system 108 the suture 412 is received in the recessed portion of the cylindrical hub surface 444 such that the suture will not be pinched or compressed excessively resulting in damage.

Figure 13:
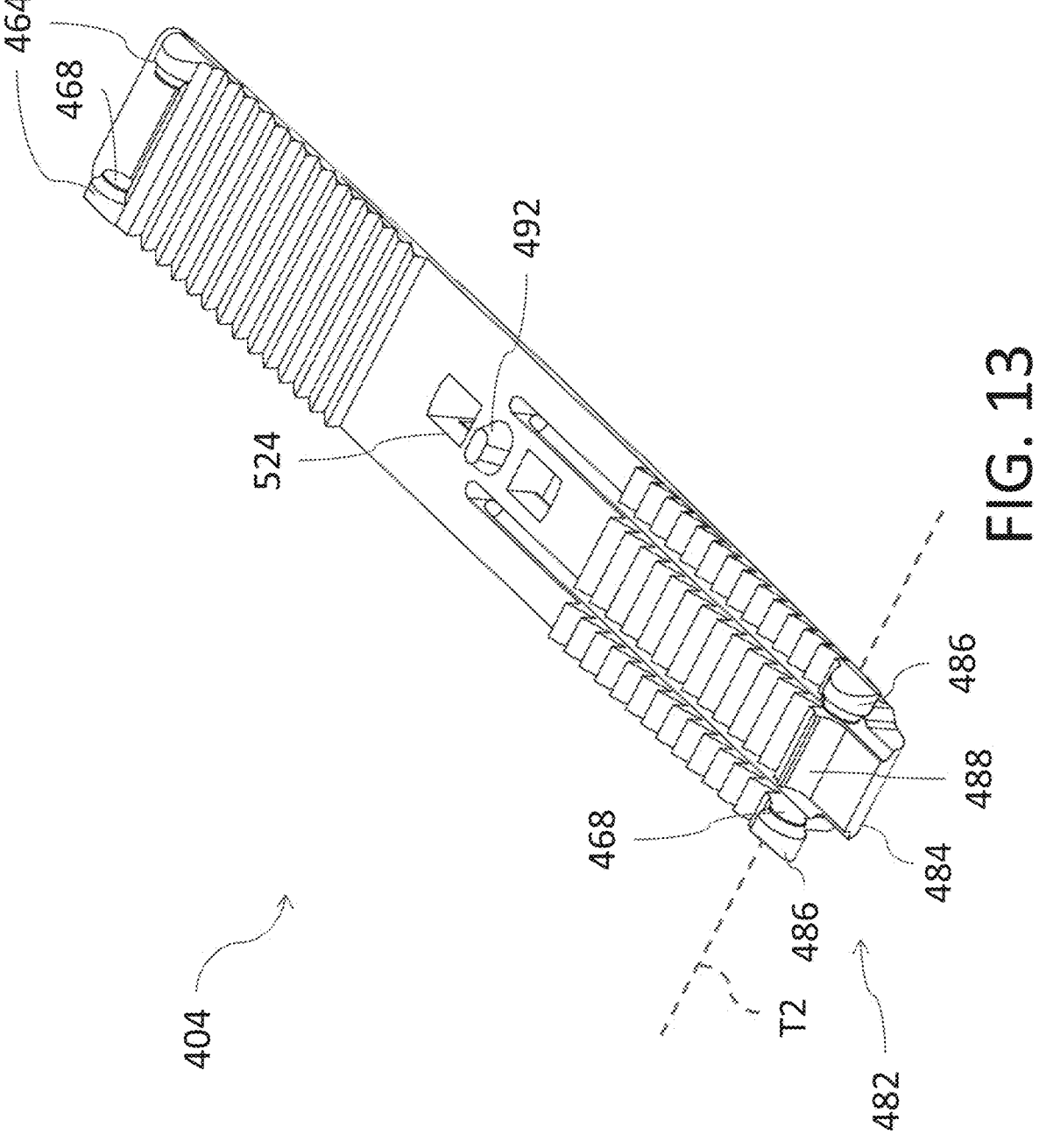
FIG. 13 is a perspective view of a distal side of one embodiment of a proximal member of the heart valve prosthesis of FIG. 5.

The first member 400 also includes a structure to provide lateral stabilization of the first member 400 relative to the second member 404. In one embodiment, a projection on one of the first and second members 400, 404 is received in a recess formed on the other of the first and second members 400, 404. FIGS. 5, 9, and 13 show that, in one embodiment, convex projections 460 on the second member 404 are received in concave recesses 464 formed on the first member 400. When the projections 460 are received in the recesses 464 abutting faces 468 on these structures prevent or minimize lateral motion between the first member 400 and the second member 404. The abutting faces 468 are sometimes referred to herein as abutment faces. The first and second member 400, 404 can have one, two, or four, or more convex projections 460 and mating concave recesses 464. In the illustrated embodiment, a projection 460 and a recess 464 is disposed adjacent to four spaced apart corners of the assembled prosthesis 108. In one embodiment, each of the projections 460 has a face 468 oriented toward the plane Lp and a face 468 disposed adjacent to each of the recesses 464 is oriented away from the plane Lp. When the first and second members 400, 404 are coupled together the faces 468 on the projections 460 are disposed across the faces 468 adjacent to the recesses 464 such there is overlap between these faces surfaces in the lateral direction. These abutting faces 468 provide a high degree of lateral stability at the periphery of the prosthesis 108.

Figure 14:
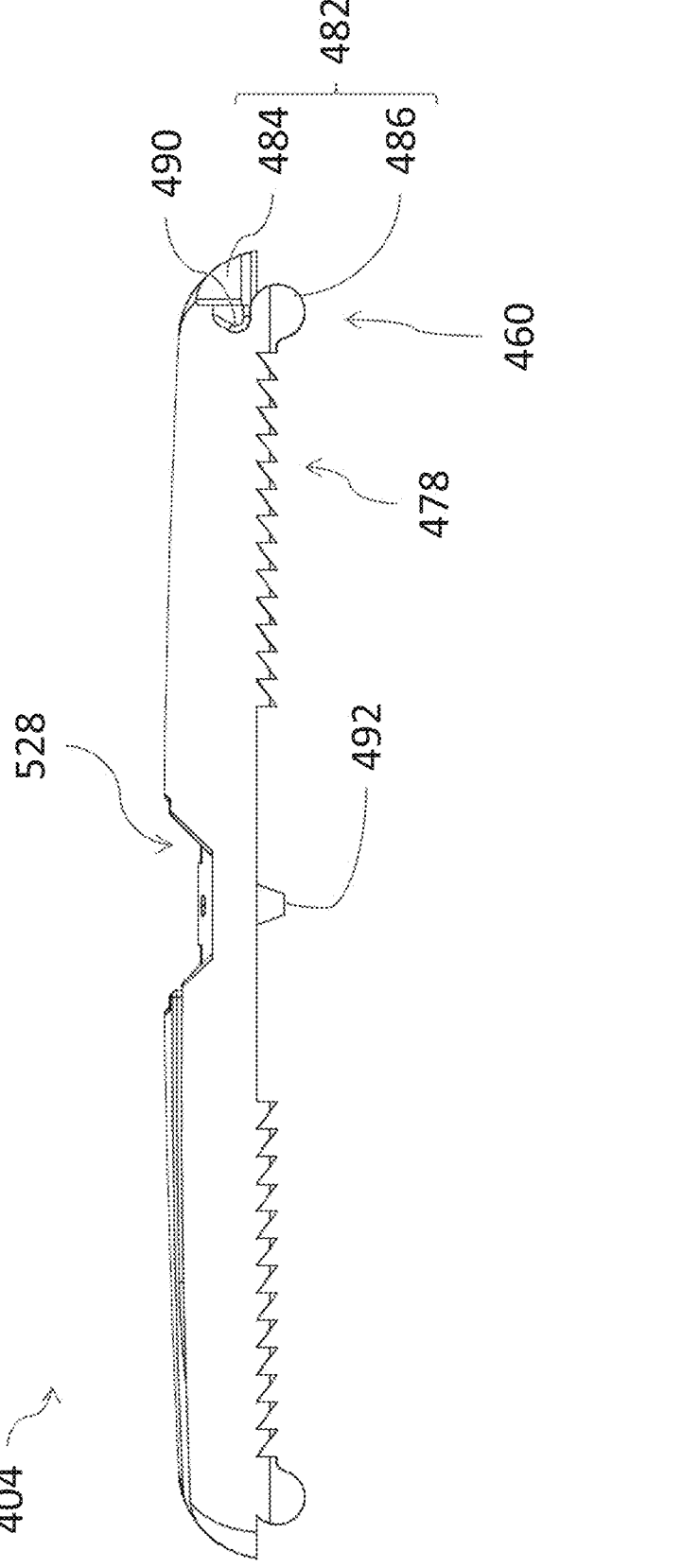
FIG. 14 is a side view of the proximal member of FIG. 13.
Figure 20:
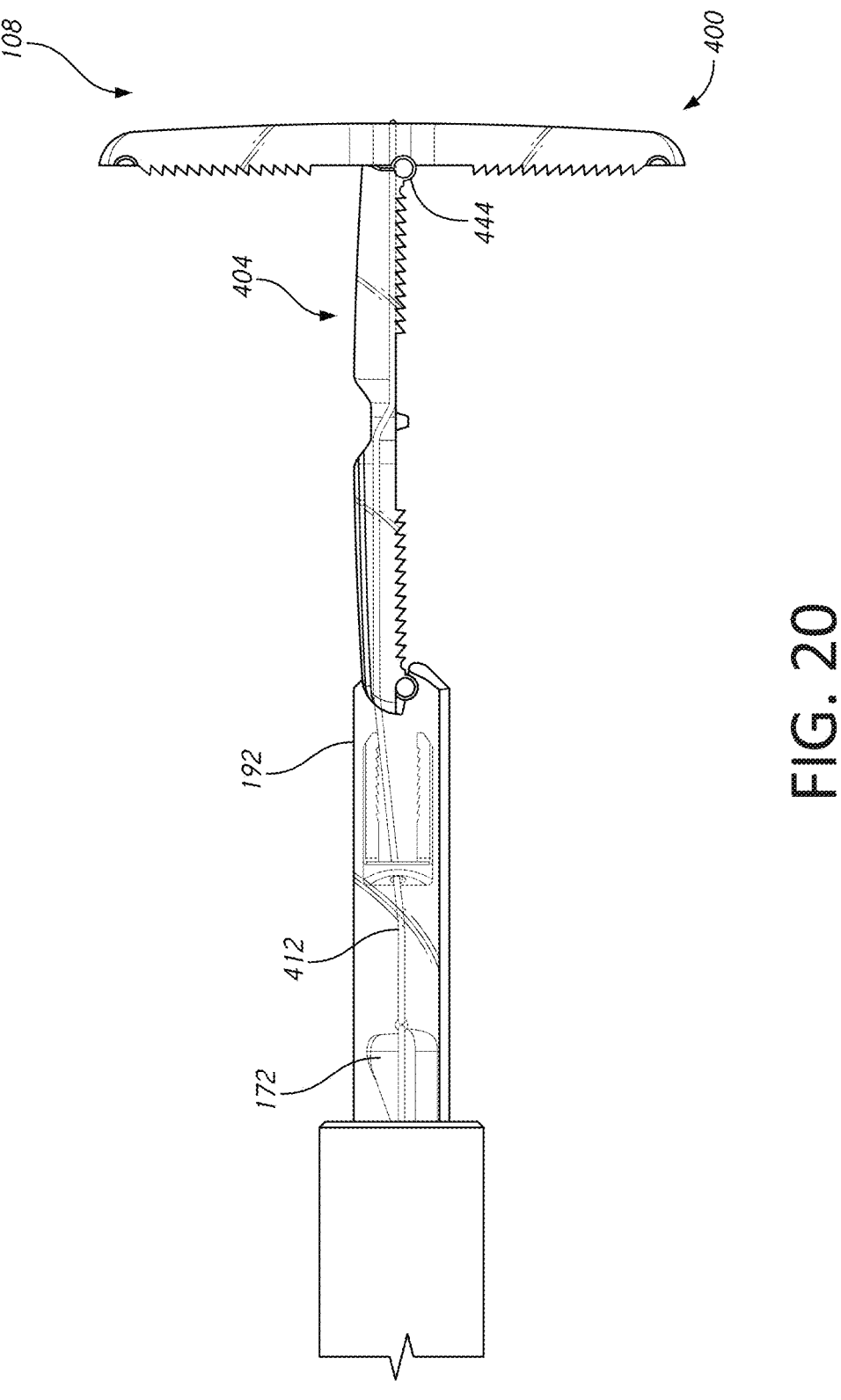
FIG. 20 is a side view of the suture, proximal member and distal member, the distal member deployed to traverse a line of coaptation, the proximal member shown in phantom illustrating the routing of the suture in a partially deployed configuration.
Figure 24:
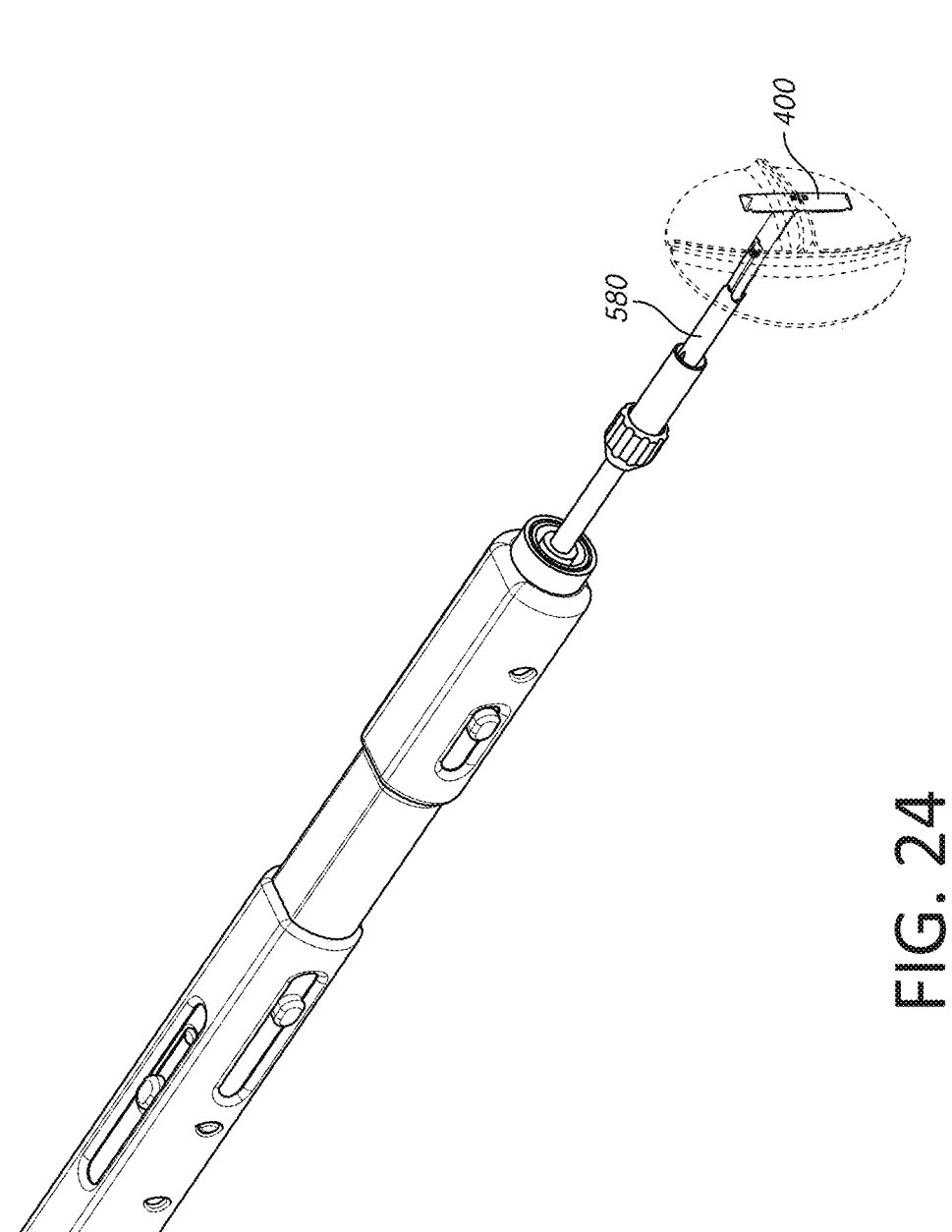
FIG. 24 shows a stage of a method following the stage of FIG. 23 in which the distal member of the heart valve prosthesis is disposed in the right ventricle and oriented transverse to a line of coaptation of the tricuspid valve.

As discussed above, the second member 404 is separate from or can be separable from the first member 400. FIG. 7 shows that the second member 404 has a central portion 472 and peripheral portions 478. The peripheral portions are disposed between the central portion and lateral ends of the second member 404. The peripheral portions 478 are configured to be placed into direct contact with two adjacent heart leaflets, e.g., on a side of the valve opposite where the first member 400 is placed. One of the peripheral portions 478 has a second hinge portion 482. FIG. 13 shows that the second hinge portion 482 at least partially surrounds, e.g., is intersected by, a second transverse axis T2. The second hinge portion 482 can include features that enable the first member 400 to pivot above the second member 404. These features permit the first member 400 to be in a deployed configuration while keeping the second member 404 within the delivery system 104 for a portion of the delivery procedure. FIG. 14 shows that in one embodiment the second hinge portion 482 includes a tab projection 484 and a convex surface 486. The convex surface 486 is adapted to allow the concave surface 432 to move thereover in a controlled fashion as the first member 400 is being pivoted relative to the second member 404. The tab projection 484 includes a curved wall 488 that has a concave shape facing the axis T2. The curved wall 488 can have a radius centered on the axis T2. The curved wall 488 provides a surface over which the cylindrical hub surface 444 pivots. At least a free end of the tab projection 484 is received in the pocket 438 when the first member 400 is fully pivoted, as shown in FIGS. 20 and 24. The second member 404 also includes a recess 490 formed in the lateral end that is configured to receive the protrusion 436 of the first member 400 when the first member 400 is fully pivoted. The structure of the second hinge portion 482 and/or the recess 490 can be found on both sides of the plane Lp as mirror images of each other.

Figure 19:
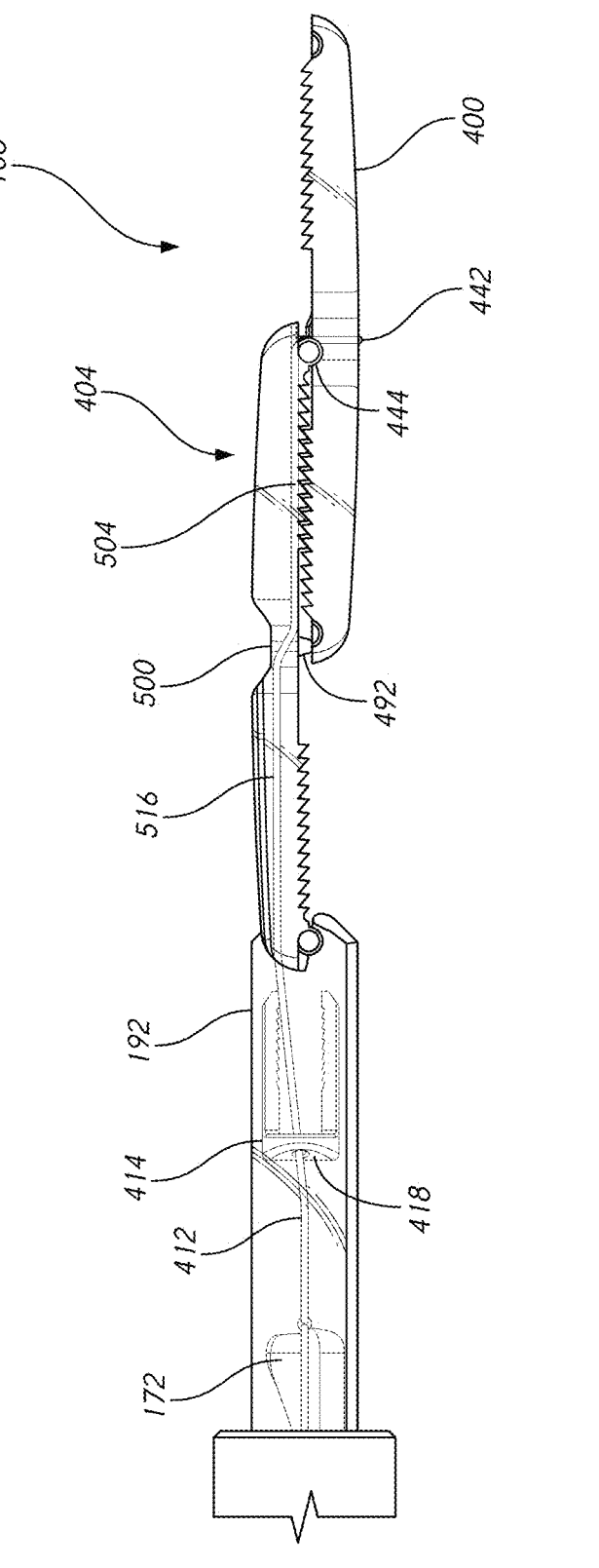
FIG. 19 is a phantom view of the distal member, the proximal member, and a suture disposed through the members when the proximal member and distal member are disposed in a low profile configuration and coupled with a portion of a delivery system.

The second member 404 also includes a central protrusion 492 disposed in the central portion 472 thereof. The central protrusion 492 can limit the longitudinal movement of the first member 400 to prevent the hinge from disconnecting when the prosthesis 108 is in the low-profile arrangement. FIG. 19 shows that in a delivery configuration of the system 100, the central protrusion 492 is disposed adjacent to one lateral end of the first member 400. When the first and second members 400, 404 are engaged with each other across a heart valve the central protrusion 492 projects into the pocket 438. In this position the central protrusion 492 can abut or face the central protrusion 492 and/or walls forming the pocket 438 to provide lateral and/or longitudinal stability between the members 400, 404.

The suture 412 disposed through the members 400, 404 and the connector 414, where present, can provide a manner of securing the first member 400 to the second member 404. In some embodiments, the suture 412 provides a control wire for aiding in positioning one or more of the first member 400, second member 404, and the connector 416 where present. FIG. 5 shows an exploded view of the prosthesis 108, which corresponds to a delivery state after the first member 400 and the second member 404 have been released from the delivery system 104 and deployed to a position for trapping heart valve leaflets. The suture 412 passes through the suture channel 442 discussed above. The second member 404 has a set of openings 500 through which the suture 412 extends from a tissue facing side to a side opposite the tissue facing side of the second member 404. The connector 416 also includes the openings 418 discussed above.

Figure 16:
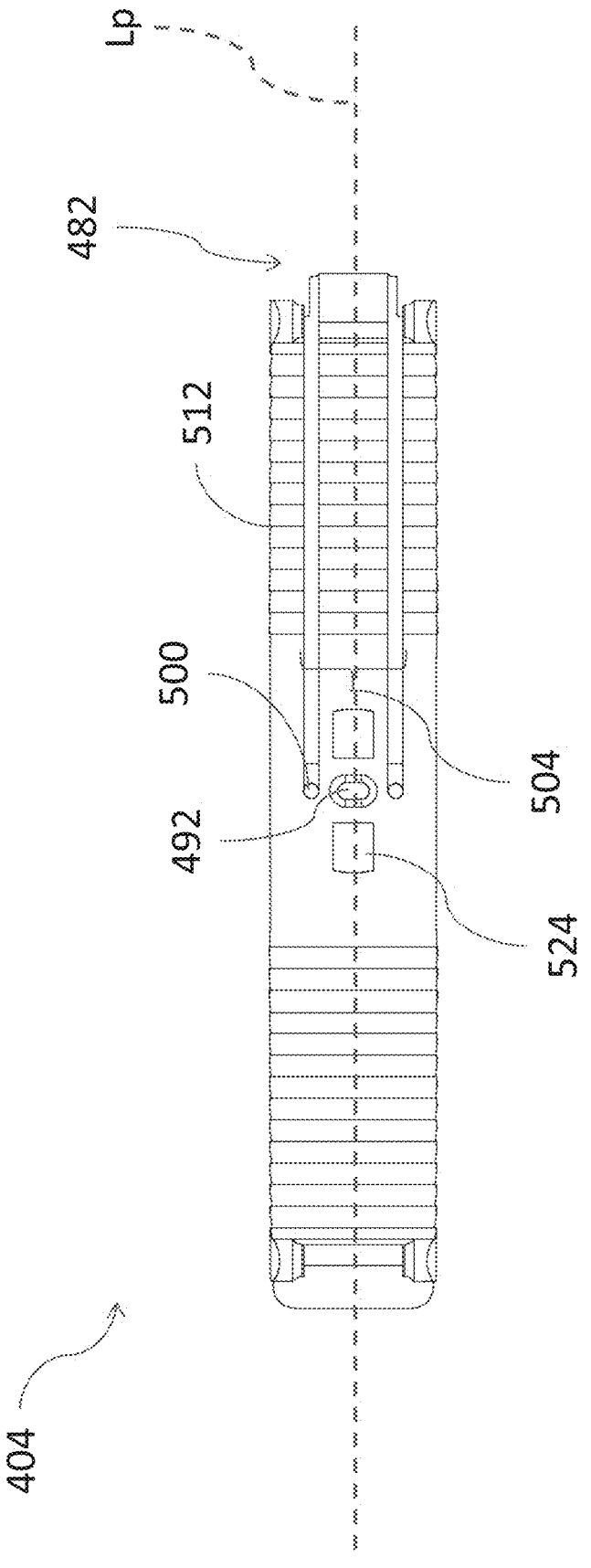
FIG. 16 is a distal side of the proximal member of FIG. 13.

FIG. 19 shows that the delivery configuration of the components of the prosthesis 108 includes a complex suture path. The suture path is facilitated by being routed through the members 400, 404 along segments of suture channels. Recessed portion of the suture channel 442 has been discussed above. FIGS. 7, 13, and 16 show that a first plurality of grooves 504 extends along the tissue facing side of the second member 404. The grooves 504 extend from the openings 500 to a lateral portion of the second member 404, e.g. to the location of the second hinge portion 482. The grooves 504, which are disposed on the tissue facing side of the second member 404, can extend parallel to the central longitudinal plane Lp. The grooves 504 are recessed into tissue engaging barbs 512 that are formed transverse to the longitudinal axis of the second member 404. The barbs 512 can take any suitable form, such as comprising friction enhancing feature such as teeth, bumps, or surface roughening. The recessed configuration of the grooves 504 reduces or eliminates interaction between the suture 412 and barbs 512 disposed on the tissue facing side of the second member 404. A second plurality of grooves 516 are formed in a side of the second member 404 that is opposite to the side of the second member having the barbs 512.

FIG. 19 shows how the suture 412 extends through the first and second members 400, 404 in a delivery configuration. In one embodiment, the suture 412 is a single continuous suture member. This permits both ends of the suture 412 to be outside the patient during delivery. The suture 412 extends from the side of the first member 400 opposite the tissue facing side thereof through the suture channel 442 and over the cylindrical hub surface 444. A span of the suture 412 extends from the cylindrical hub surface 444 through the first set of grooves 504. The suture 412 is protected from the barbs 512 in the recessed grooves 504. The suture 412 extends through openings 500 from the tissue facing side to the side of the second member 404 opposite the tissue facing side. A span of the suture 412 extends from the openings 500 through the second set of grooves 516. The grooves 516 are recessed into the side of the second member 404 opposite the barbs 512 thereon. The grooves 516 face the inside of the second elongate member 192 in the delivery system 108. The sutu7re 412 is protected in the grooves 516 from interacting with and potentially being damaged by edges or portions of the member 192 during delivery. The curvature of the grooves 516 and tension on the suture 412 causes a span of the suture proximal of the second member 404 to traverse toward the center of the lumen of the second elongate member 192. The suture 412 also extends through the openings 418 of the connector 414 as it transitions toward the center of the lumen of the second elongate member 192.

FIGS. 4B and 4C show more details about the suture path proximal of the distal end of the second elongate member 192 in connection with a modified embodiment of the prosthesis 108. The suture path extends from lateral ends of grooves 516A to apertures 418 formed in a proximal body 415A. The suture path then extends to a pre-tied knot portion 412A. The suture path then extends around the distal end 176 of the first elongate member 172 to a second knot portion 412B. The second knot portion 412B is disposed proximally of the first knot portion 412A. Preferably the knot portions 412A, 412B are slip knots or other configurations capable of being pushed remotely the first elongate member 172.

Movement of the knot portions 412A, 412B can be accomplished by relative sliding of the first elongate member 172 within the second elongate member 192. The distal end 176 of the first elongate member 172 can have a concave distal face 177 that can be used to urge the knot portion 172A distally into position, following the method step illustrated and discussed more fully below in connection with FIGS. 29 and 30. The distal face 177 also can be the structure that urges the second member 404A off of the distal end 176 of the second elongate member 192. The distal face 177 also can be used to advance the connector 412A if present. The distal end 176 can generally fill the interior space of the second elongate member 192, which is tubular. This prevents the knot portions 412A, 412B from inadvertently being lodged between the first and second elongate members 172, 192. In one embodiment, the clearance between the distal end 176 and the inner wall of the second elongate member 192 is less than the thickness of the suture or of the knot portion 412A, 412B of the suture 412.

In order to transition the distal end 176 to a position proximal of the knot portion 412B an opening 197 is provided in the second elongate member 192. To move the distal face 177 proximal of the knot portion 412B a proximal ramp portion of the distal end 176 is slid proximally relative to the knot portion 412B at the location of the opening 197. The opening 197 allows the knot portion 412B to move radially outward of the inner profile of the second elongate member 192. This avoids pinching, crushing or otherwise stressing the knot portion 412B or other adjoining lengths of the suture 412.

FIG. 4D show that the suture path continues from the knot portion 412B. In one embodiment, the suture 412 extends radially outward from the knot portion 412B through apertures 198 in the second elongate member 192 to suture channels 194 formed in the side of the second elongate member proximally of the apertures 198. The suture channels 194 can be seen in FIG. 4B. The suture channels are on both sides of the second elongate member 192. The suture channels do not extend distally of the apertures 198. The suture channels can be exposed the housing 152. FIG. 4C shows that the inner shell 312 defines a space that is large compared to the suture 412. The suture 412 are exposed to this space but carried within the suture channels 194. The suture path extends proximally through the shell 312 to the suture control assembly 240, discussed above in FIG. 4A.

Figure 15:
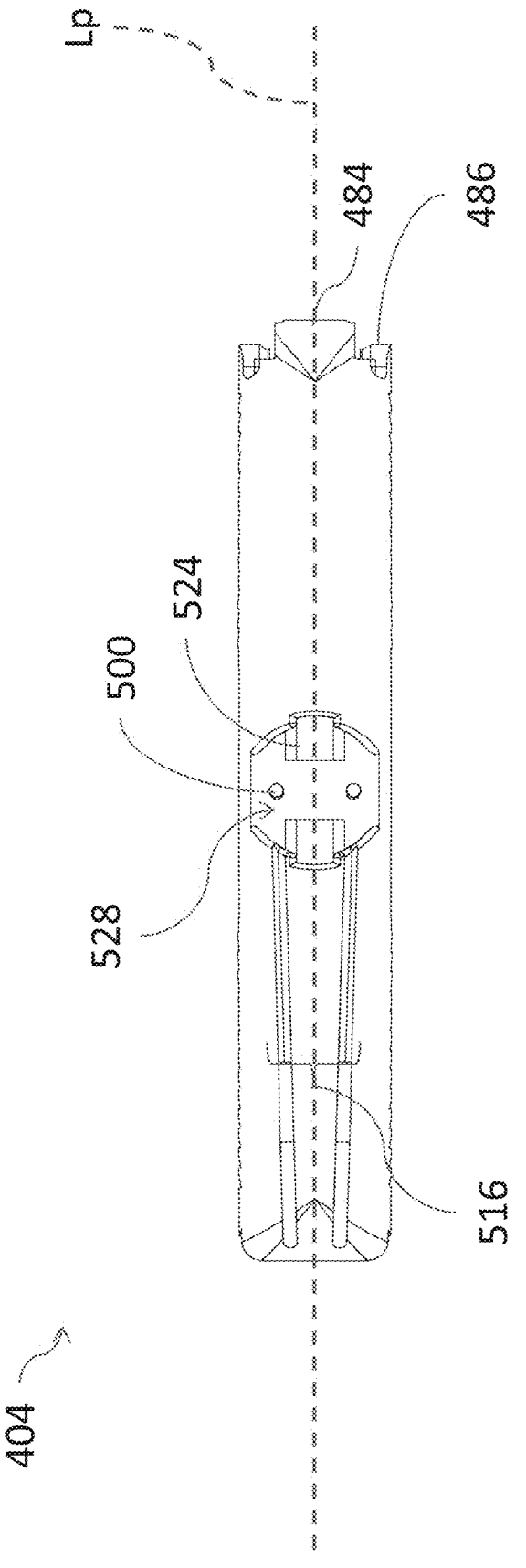
FIG. 15 is a proximal side of the proximal member of FIG. 13.

FIG. 15 also shows that in some embodiments, the grooves 516 are splayed, e.g., diverge toward the openings 500. The grooves 516 converge toward the peripheral edge of the second member 404 that engages the second elongate member 192 of the delivery system 108. Such convergence allows two spans of the suture to be more closely disposed within the delivery system 108. The suture 412 is then routed along the first elongate member 172 to be tensioned by the suture control assembly 240 adjacent to the proximal end 180.

FIG. 20 shows that the path for the suture 412 in a partially deployed configuration is similar to the suture path in the delivery configuration of FIG. 19. A difference is that the cylindrical hub surface 444 has pivoted on the curved wall 488. In certain arrangements, convex surface 486 and concave surface 432 provide the primary pivot for moving the prosthesis 108 from the delivery configuration to the deployed configuration, with the cylindrical hub surface 444 providing an offset path for the suture 412. In certain variants, the cylindrical hub surface 444 can provide a pivot for guiding movement of the prosthesis 108 from the delivery configuration to the deployed configuration. Such pivoting results in part from tension in the suture 412 and in that the portion of the suture 412 that extends through the recess of the suture path 442 is offset from the suture through holes in the first member 400. When the first member 400 is pivoted to the delivery configuration the suture 412 is partially wound around the cylindrical hub surface 444. Pivoting the first member 400 unwinds the partially wound portion of the suture 412. Accordingly, the suture path in the partially deployed state of FIG. 20 provides that the portion of the suture 412 that extends in the transverse portion of the suture path 442 is now directly below the through-holes in the first member 400 and the suture 412 extends substantially straight to the central portion 472 of the second member 404.

As discussed above, some embodiments employ the connector 414 to secure the first and second member 400, 404. FIGS. 9, 11, 13 and 15 show features of the members 400, 404 that enable the connector 414 to be secured thereto. FIGS. 9 and 11 show that the first member 400 can include apertures 520 disposed on the plane Lp and spaced laterally from the longitudinal mid-point of the member 400. The apertures 520 are identical in one embodiment. FIGS. 9 and 11 show that the apertures 520 extend from the tissue engaging side of the member 400 to the opposite side thereof. FIG. 9 further shows that the apertures 520 can include barbs 522 that can engaged with the barbs 417 on the members 416 of the connector 414. In one embodiment, the aperture 520 disposed adjacent to the cylindrical hub surface 444 comprises barbs 522. In one embodiment, one of the apertures 520 opens to, is adjacent, to, or is contiguous to the pocket 436 on the tissue engaging side of the first member 400. FIGS. 13 and 15 show that the second member 404 can include apertures 524 disposed on the plane Lp and spaced laterally from the longitudinal mid-point of the member 404. The apertures 524 are identical in one embodiment. FIGS. 13 and 15 show that the apertures 524 extend from the tissue engaging side of the member 404 to the opposite side thereof. The apertures 524 can include barbs or one or more ridges to engage a portion of the members 416. In one embodiment, the second member 404 has a recess 528 into which the connector body 415 is received when the prosthesis 108 is fully assembled. The apertures 524 open to the recess 528 on the side of the second member 404 opposite the tissue engaging side thereof.

IV. Heart Valve Prosthesis Delivery Methods & Systems

FIGS. 21-30 show additional features of the heart valve prostheses delivery system shown in FIGS. 3 and 4 and methods related to the same. As discussed above, the prosthesis 108 is delivered with the components disposed in a low profile state and is thereafter assembled within the heart. The systems described in connection with FIGS. 21-30 are configured to provide a high level of control of the position of the members 400, 404 by use of positively engaging latches or similar structures that can be un-latched to provide relative movement within the delivery system or among the members 400, 404

As discussed above, the coupling assembly 154 enables releaseably coupling the delivery catheter 132 to the housing 152. In one embodiment, the coupling assembly 154 includes one or a plurality of projections 156 that can be received in recesses or opening 560 formed in a proximal portion of the delivery catheter 132. The delivery catheter 132 can include a proximal disc 564 portion with axial through holes configured to receive the projections 156. In one embodiment, the disc 564 can include peripheral threads 568 that engage with internal threads 572 of a collar 158 of the coupling assembly 154.

In one method, access to vasculature of a patient is provided by inserting the introducer 120 through the skin into a peripheral blood vessel, such as the right internal jugular vein, the left internal jugular vein, or via the inferior vena cava. The deliver catheter 132 is coupled with the housing 152. For example, the projections 156 can be advanced into the openings 560 of the proximal disc 564 and the internal threads 172 of the collar 158 can be engaged to the external threads 568 of the proximal disc 564 of the delivery catheter 132.

Figures 22, 22A:
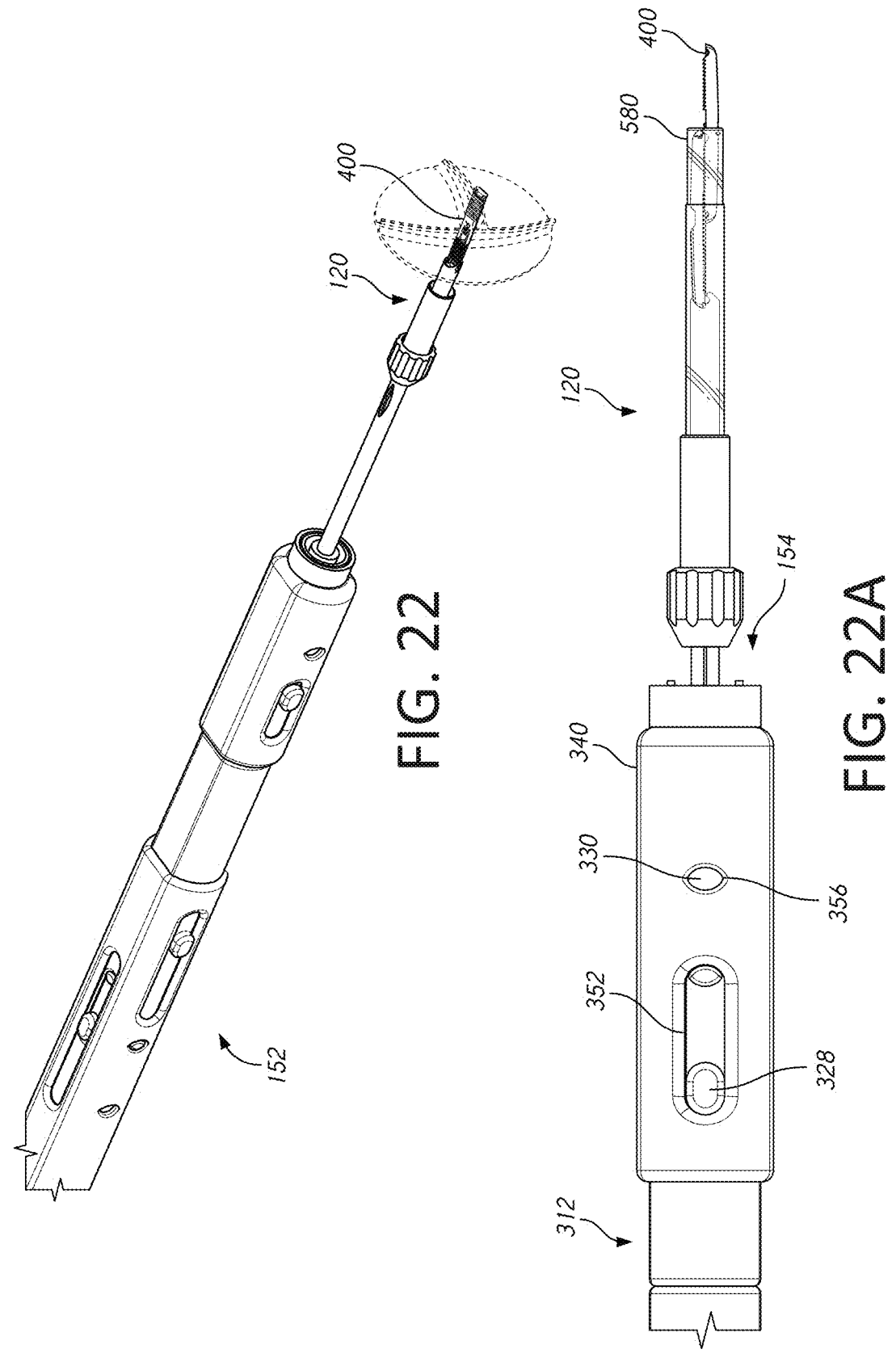
FIG. 22 shows a stage of a method in which the heart valve repair system is being advanced within the right atrium toward the tricuspid valve.
FIG. 22A is a close up view of a portion of the delivery system of FIG. 3 suitable for the stage of the method shown in FIG. 22.

The delivery catheter 132, coupled with the housing 152, can then be inserted into the introducer 120 and advanced toward the heart. FIG. 22 shows that insertion can continue until the first member 400 and the distal end 580 of the delivery catheter 132 are in the heart adjacent to the valve, e.g., in the right atrium adjacent to the tricuspid valve. The delivery catheter 132 is removed from FIG. 22 for clarity. Although there is very little length shown in FIG. 20 between the distal end of the introducer and the components of the prosthesis 108 disposed at the distal end of the delivery catheter, there may be substantial length in actual use, such that the delivery catheter 132 may traverse most of the distance from the peripheral percutaneous access site to the heart. FIG. 22(A) shows the relative position of the components of the prosthesis 108 and the delivery catheter 132 at the distal end of the heart valve repair system 100. For example, the first member 400 is disposed such that a longitudinal mid-point thereof is disposed across a distal end 580 of the delivery catheter 132.

Figures 23, 23A:
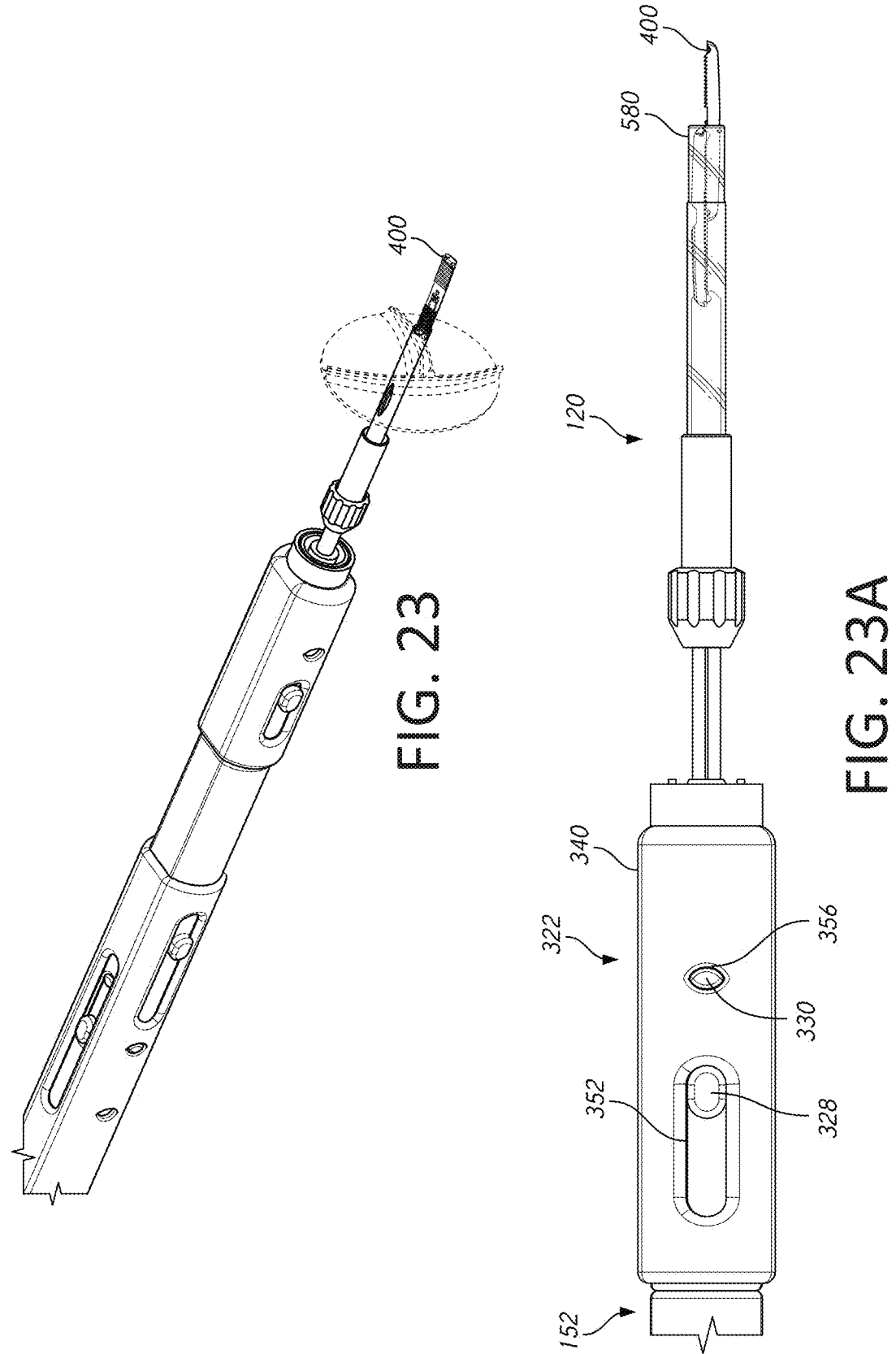
FIG. 23 shows a stage of a method in which the distal end of the heart valve repair system is disposed across the tricuspid valve in the right ventricle.
FIG. 23A is a close up view of a portion of the delivery system of FIG. 3, showing how the system is manipulated to expose the distal member in the right ventricle.

FIGS. 23 and 23A show a step subsequent to that of FIGS. 22 and 22A in which the first member 400 is fully exposed outside the distal end 580 of the delivery catheter 132. This result can be achieved by any suitable method or structure. FIG. 23A shows the end of one method. From the stage and configuration of FIG. 22A, the actuator 328 is depressed, e.g., moved into the page as shown in this view. This movement causes the locking feature 330 to be moved out of the slot 352 to within the distal portion 322 of the outer shell 340. The outer shell 340 can then be shifted proximally relative to the inner shell 312 until the locking feature 330 is in the aperture 356. In this position, the distal end 580 of the delivery catheter 132 is disposed proximally of the proximal-most portion of the first member 400. In the delivery configuration, the proximal-most portion of the first member 400 is a peripheral end of the member 400.

FIG. 24 shows a stage following that of FIG. 23 in which the first member 400 is pivoted about the transverse axes T1 and T2. In the delivery state these axes are aligned at the stage illustrated in FIG. 23. The tension in the suture 412 acts on the cylindrical hub surface 444 to cause rotation of the member 400, which rotation can be on the curved wall 488. As the rotation occurs the distal portion of the suture path changes from that shown in FIG. 19 to that shown in FIG. 20. The distal-most portion of the suture 412 changes from being transverse, e.g., perpendicular, to the orientation of the first plurality of grooves 504 to being aligned with the grooves 504. This pivoting can be controlled by tension in the suture 412.

FIG. 25 shows a stage following that of FIG. 24 in which portions of the delivery system 104 is retracted relative to the first member 400 and the suture 412. A distal portion of the delivery system 104 is retracted while retaining a proximal portion in place. The distal end of the second elongate member 192 and the second member 404 coupled therewith are retracted by drawing the second inner shell 312 into the second outer shell 344. To accomplish this, the actuator 332 is depressed relative to the outer shell 344 allowing the locking feature 334 to be shifted from the slot 372 to the proximal-most aperture 374. The advancement of the distal end of the second elongate member 192 relative to the proximal portion of the housing 152 provides clearance so that the full length of the second member 404 can be accommodated between the distal end 580 of the delivery catheter 132 and the tricuspid valve.

Figure 26:
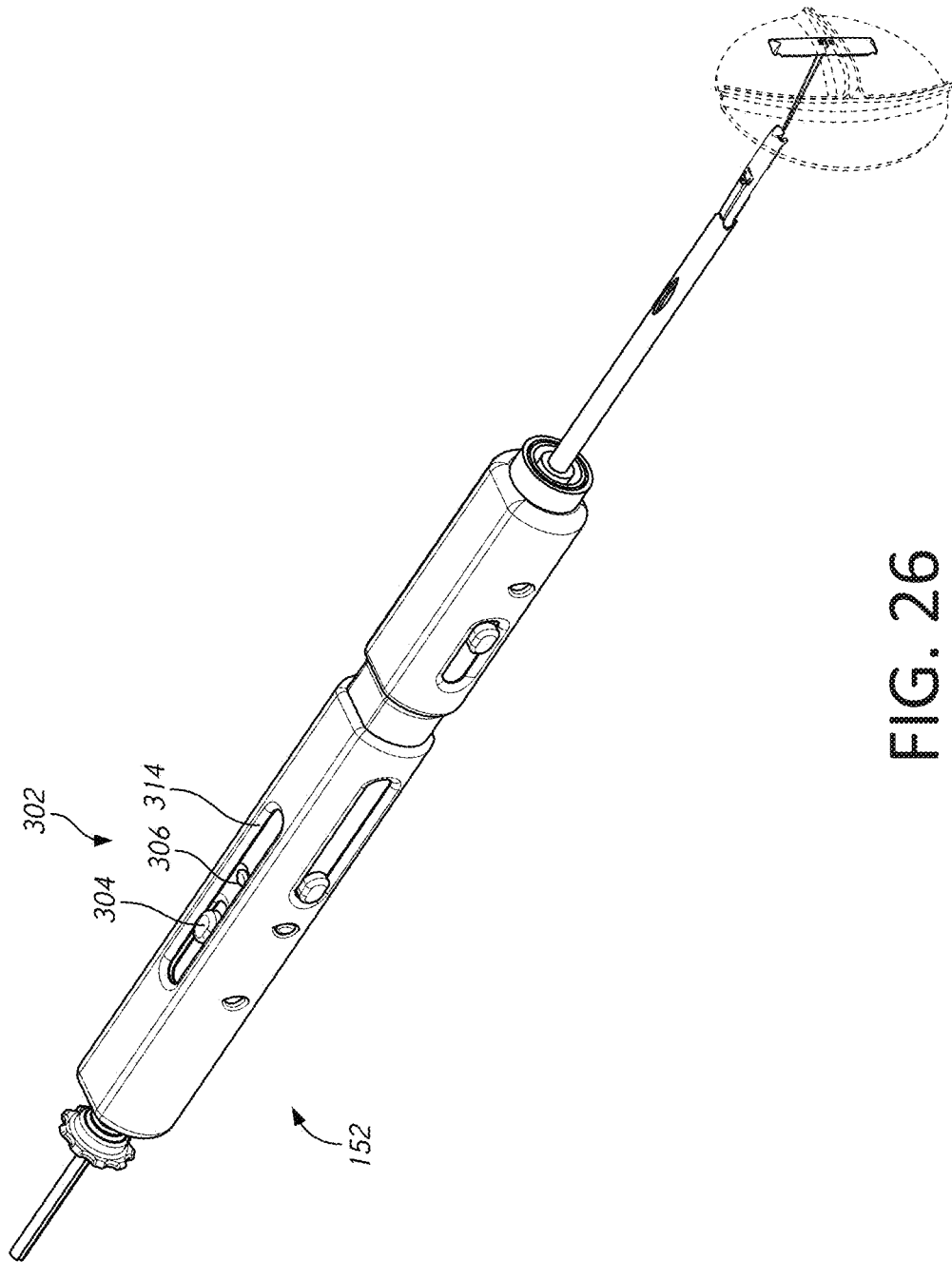
FIG. 26 shows a stage of a method following the stage of FIG. 25 in which the proximal member of the heart valve prosthesis has been advanced out of the distal end of the delivery system.

FIG. 26 shows a stage following that of FIG. 25. In this stage, the position of the second member 404 can be shifted forward while maintaining the position of the distal end 580 of the delivery catheter 132. This is accomplished by depressing the actuator 304 inward relative to the inner shell 312. This causes the locking feature 306 to be shiftable out of a slot in the inner shell 312 and to the locking aperture 316. Once fully clear of the distal end 580, the end face of the second member 404 can become separated from the second elongate member 192. If such separation does not occur, the second member 404 can be ejected from the elongate member 192 by urging the connector 414 distally or by directly pushing the distal end of the first elongate member 172 with the end of the second member 404.

Figure 27:
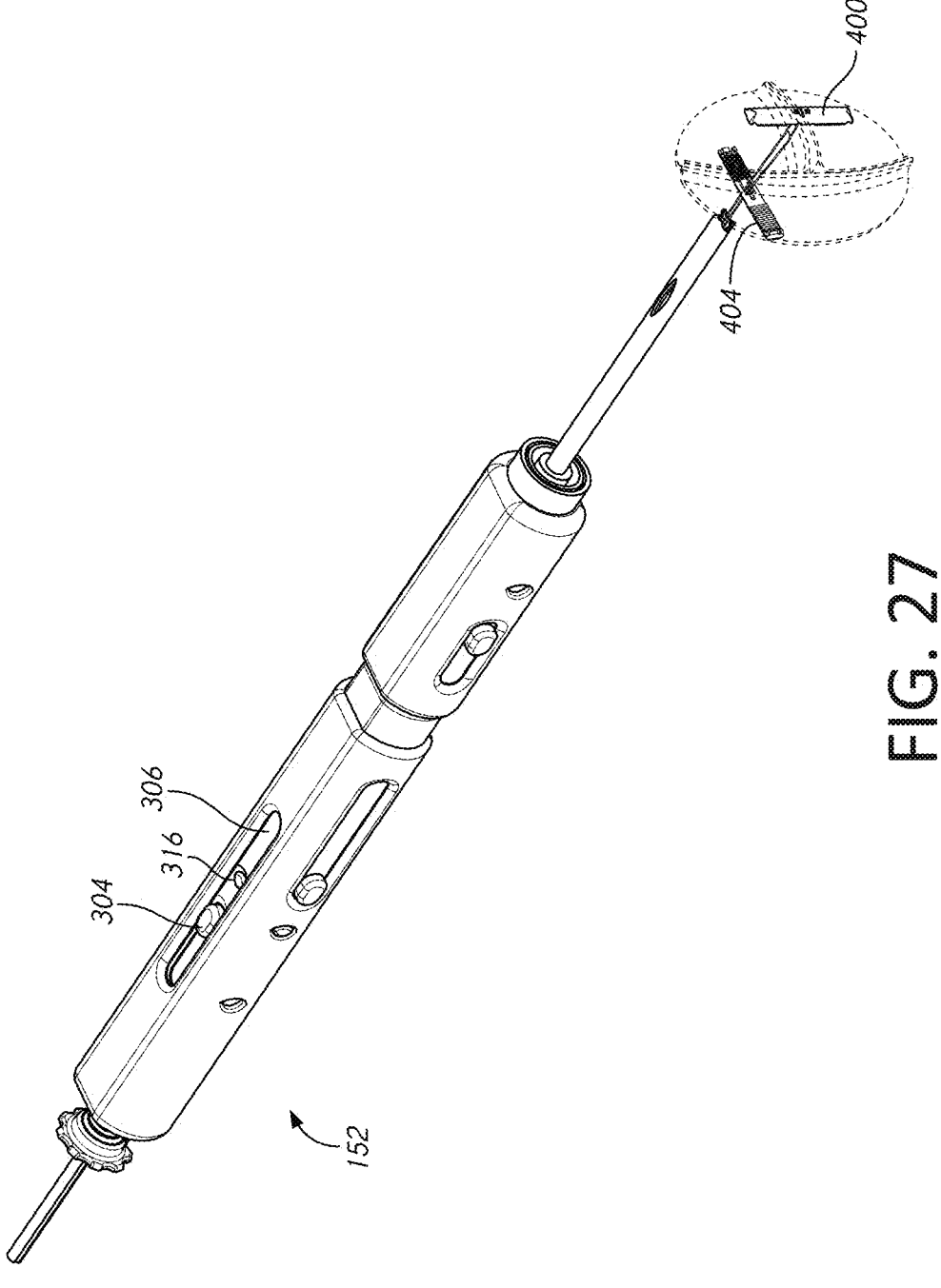
FIG. 27 shows a stage of a method following the stage of FIG. 26 in which the proximal member has been released and allowed to rotate toward a transverse orientation facing the line of coaptation of the tricuspid valve.

FIG. 27 shows a stage following that of FIG. 26, in which the second member 404 is optionally shifted further distally by selecting a third position of the first inner shell 300. The third position is further distal than the position shown in FIG. 26. This is accomplished by again depressing the actuator 304 and then shifting the locking feature 306 distal of the aperture 316. FIG. 27 also shows that once the second member 404 is free of the distal end of the second elongate member 192 the member 404 can rotate to an orientation suitable for traversing the line of coaptation of the valve leaflets and facing the first member 400 which is disposed across the valve.

Figure 28:
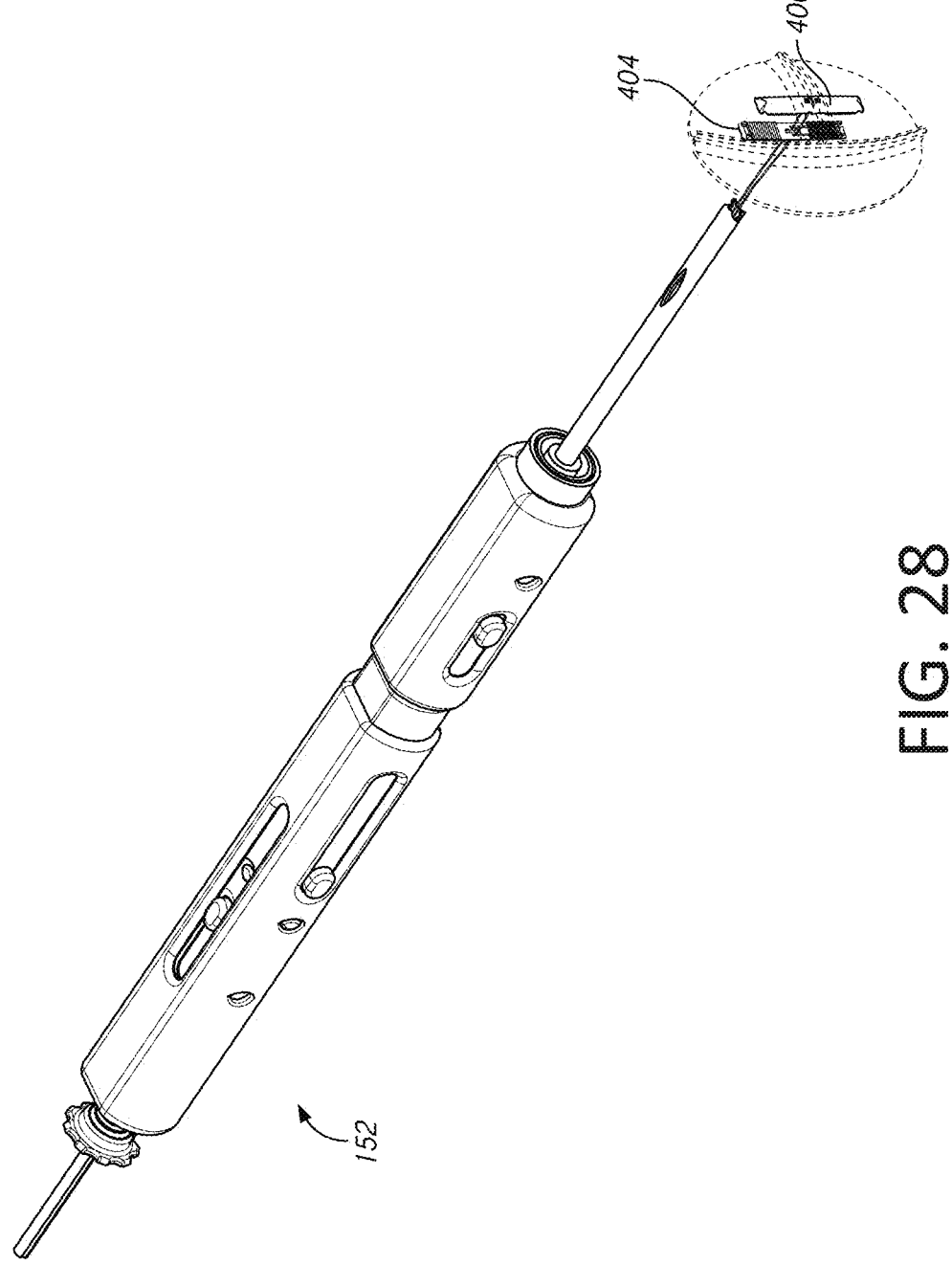
FIG. 28 shows a stage following the stage of FIG. 27 in which the proximal member of the heart valve prosthesis is advanced into position adjacent to the tricuspid valve.

FIG. 28 is similar to FIG. 27 but shows the second member 404 moved closer to the valve. This movement can be by the flow of blood within the atrium which provides a generally distal movement of the member 404. As discussed above, the movement of the second member 404 toward the first member 400 can be preceded by an ejecting movement or force applied by the connector 414 to the second member 404. The force can be transferred from a distal face of the first elongate member 172 through the connector 414.

Figure 29:
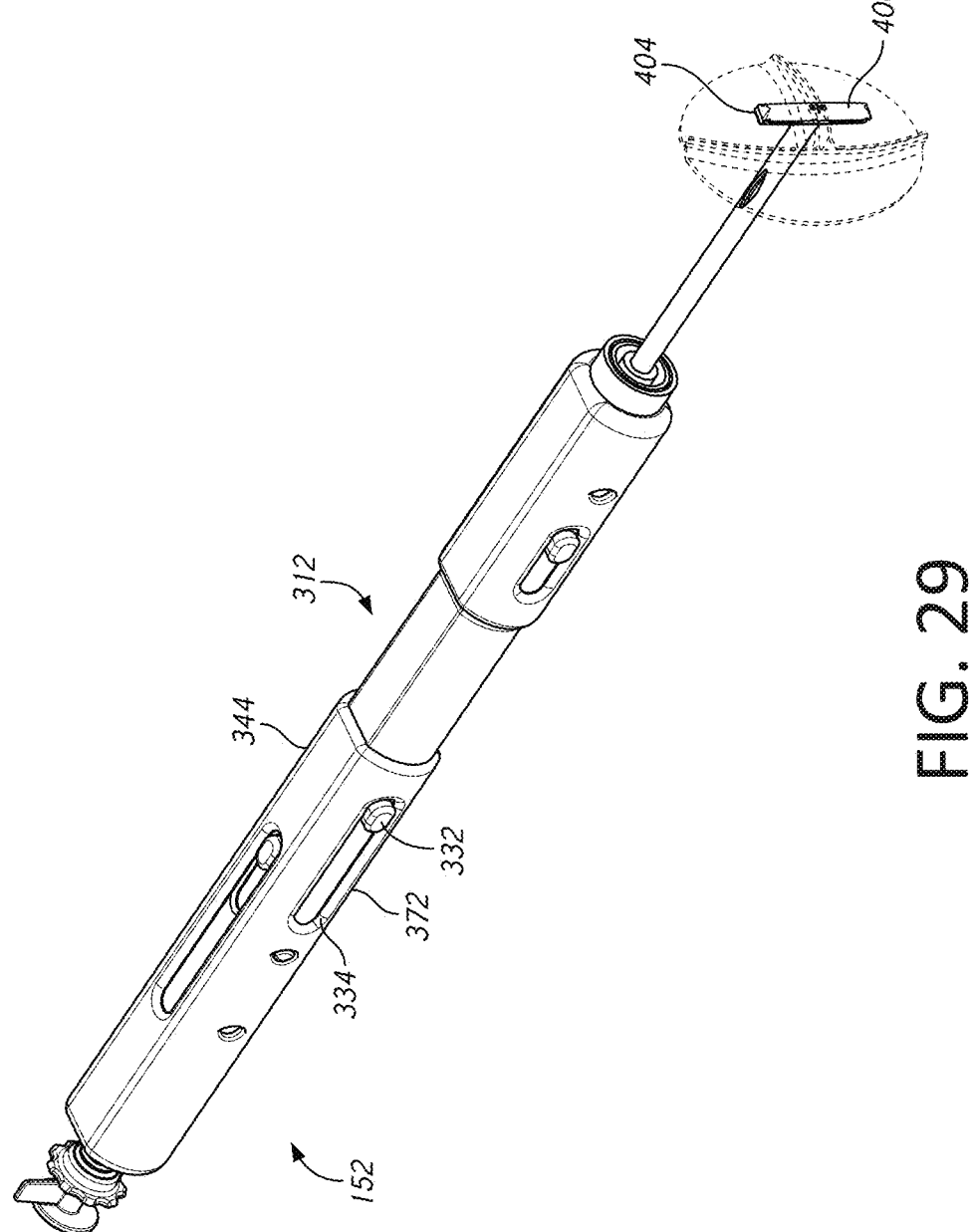
FIG. 29 shows a stage following the stage of FIG. 28 in which the proximal member is disposed adjacent to the distal member, across the tricuspid valve.
Figure 30:
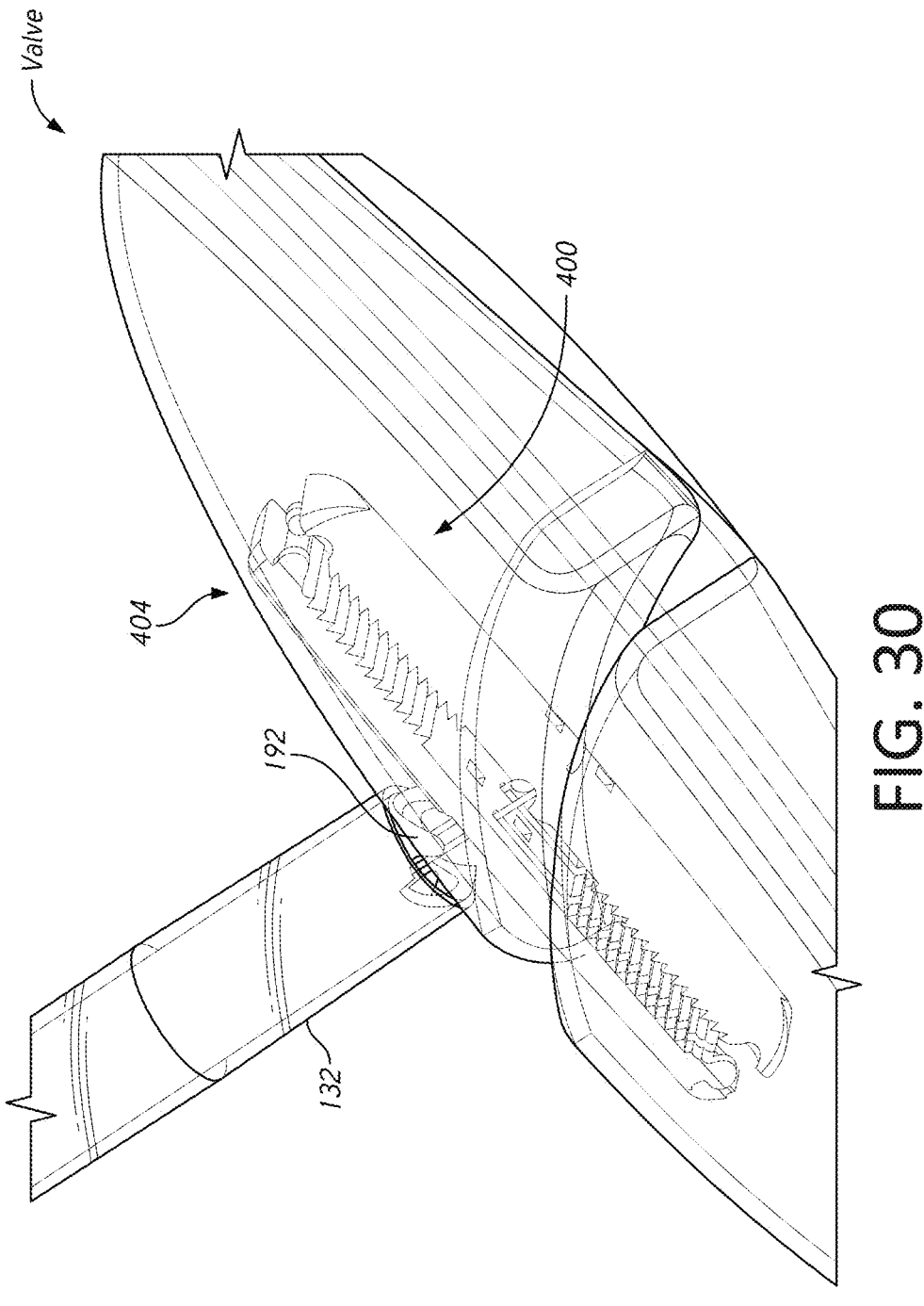
FIG. 30 show the distal member and the proximal member in the deployed configurations similar to that illustrated in FIG. 29.

FIGS. 29 and 30 show that the distal end of the second elongate member 192 can be shifted forward to be disposed over the proximal side of the second member 404. This shifting can be accomplished by moving the inner shell 312 distally relative to the outer shell 344. The movement of the inner shell 312 also moves the outer shell 340. FIG. 30 shows that the distal face of the second elongate body 192 can be formed to at least partially receive the proximal side of the second member 404. For instance, the distal face of the second elongate member 192 can have a concave profile. The proximal side of the second member 404 has a convex profile so the proximal side can be received within the concave area of the distal end of the second elongate member 192. When so positioned the distal end of the second elongate member 192 can exert control over the second member 404 and/or over the motion of the connector 414. For example, the connector can be guided in the lumen of the second elongate member 192 with little to no exposure to the side of the member 192 between the distal end of the elongate member 192 and the proximal side of the second member 404. This provides the benefit of minimizing the risk of the connector 414 partially or completely slipping out of alignment with the apertures 524. The suture 412 which is held taught by the suture control assembly 240 provides good control over the connector 414. But by nesting the distal end of the elongate member 192 over the proximal side of the second member 404 the step of connecting the connector 414 to the first and second members 400, 404 is enhanced.

V. Additional Embodiments Including Rigid Plates

FIGS. 31-35 show additional embodiments of heart valve prostheses that include rigid plate members that are assembled within the patient to secure the heart valve. These additional embodiments are similar to the prosthesis 108 except as described differently below. Aspects of the foregoing disclosures may be combined with the following disclosure.

FIGS. 31-34 show a prosthesis 600 that includes a first member 602, a second member 604 and a suture retainer 608. The first member 602 is similar to the first member 400 which has been described above. The second member 604 can have some or all of the same features of the second member 404. The second member 604 has a recess 612 that is similar to the recess 528 but is configured to receive the suture retainer 608.

The suture retainer 608 is configured to secure the suture 412 to the second member 604. The suture retainer 608 includes a retainer member 620 and a plurality of apertures 624. The retainer 608 includes one aperture for each span of the suture 412 that passes through the member 620 from a first side 628 to a second side 632. The first side 628 can be a valve facing, e.g., a distal, side. The second side 632 can be a proximal side, e.g., opposite to the valve facing side. The retainer 608 can have a saddle shaped body, e.g., having concavities on two sides that are oriented transversely to each other.

Figure 31:
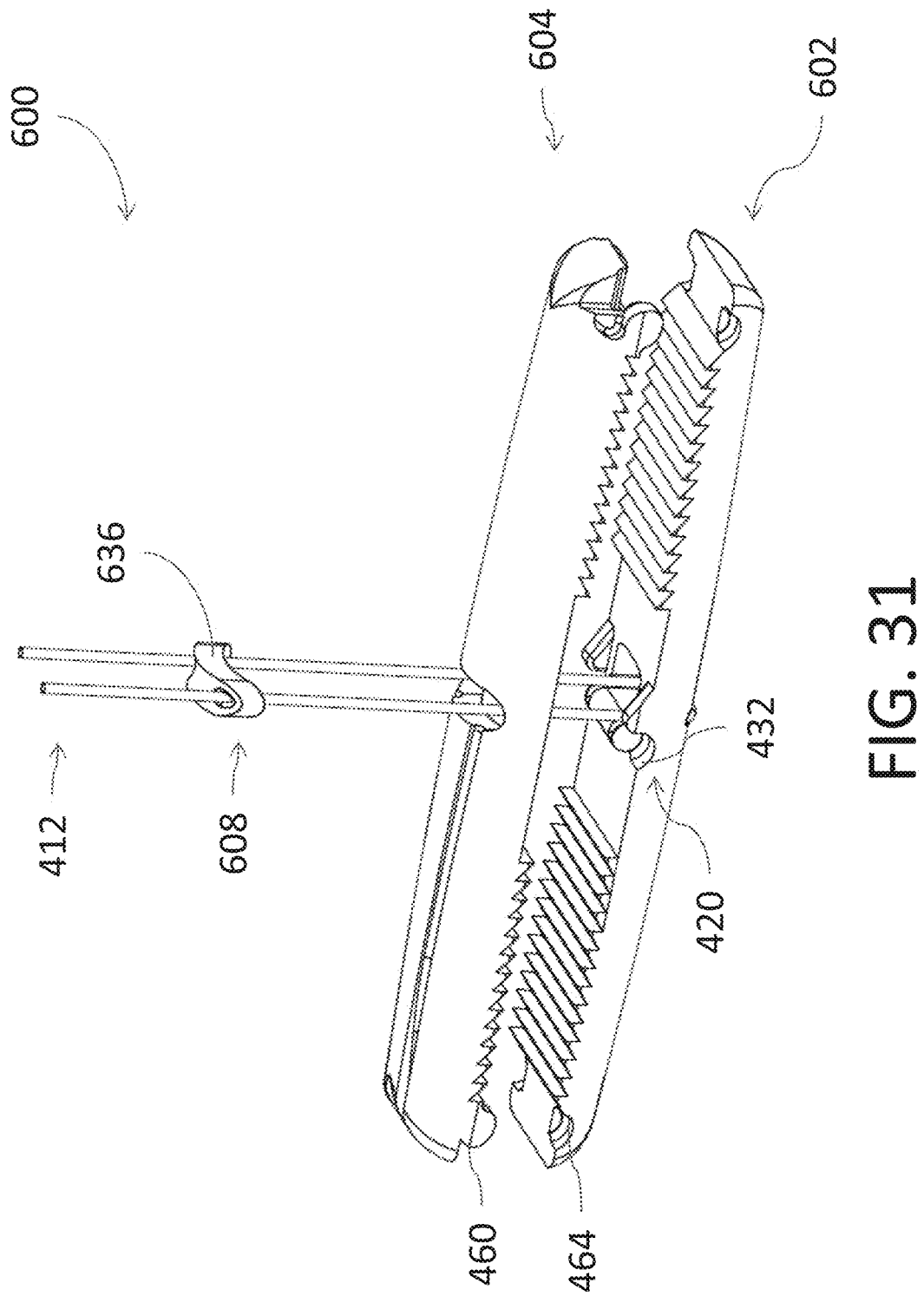
FIGS. 31-34 show another embodiment of a heart valve prosthesis having a suture securing device.
Figure 32:
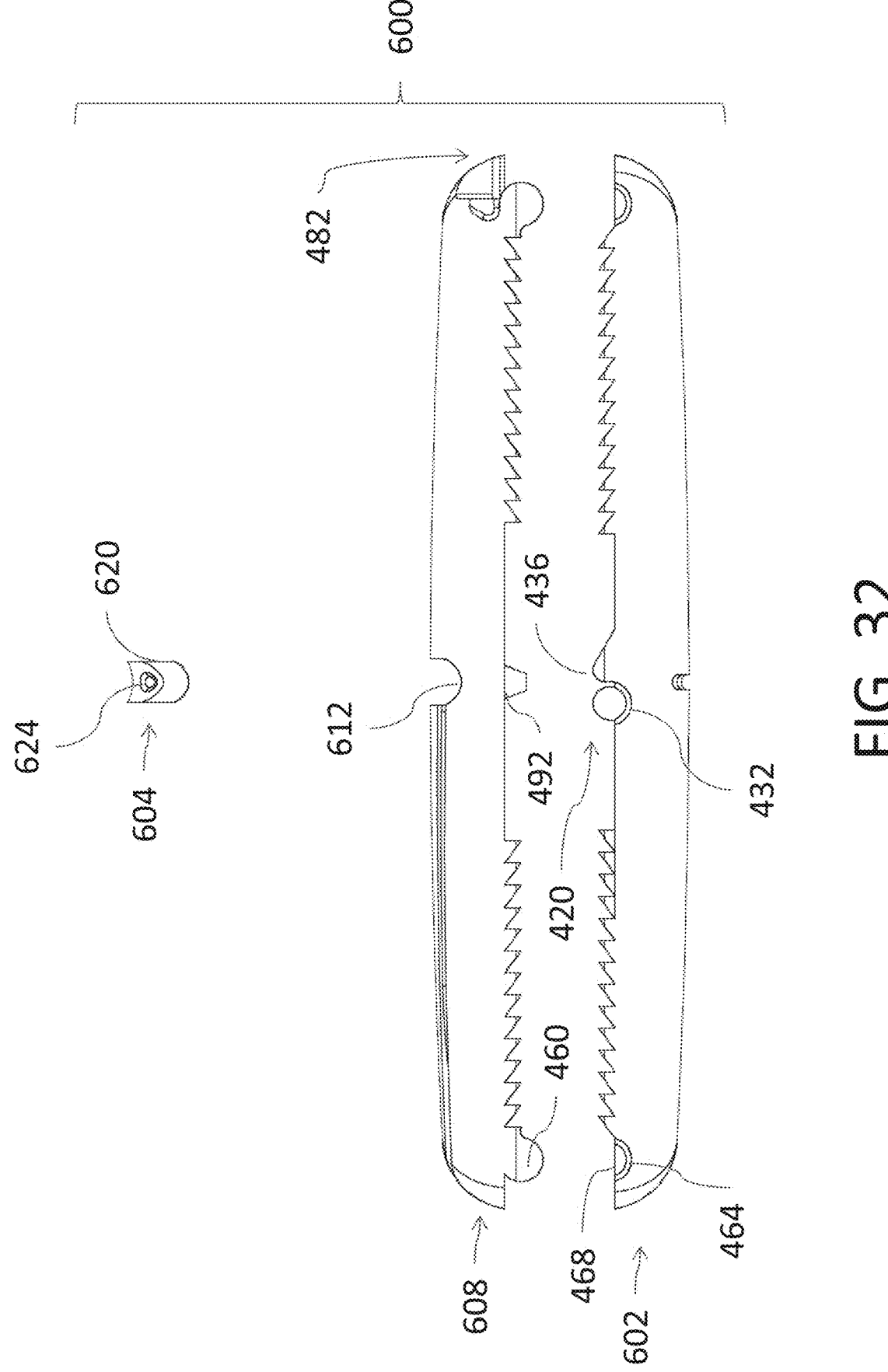
Figure 33:
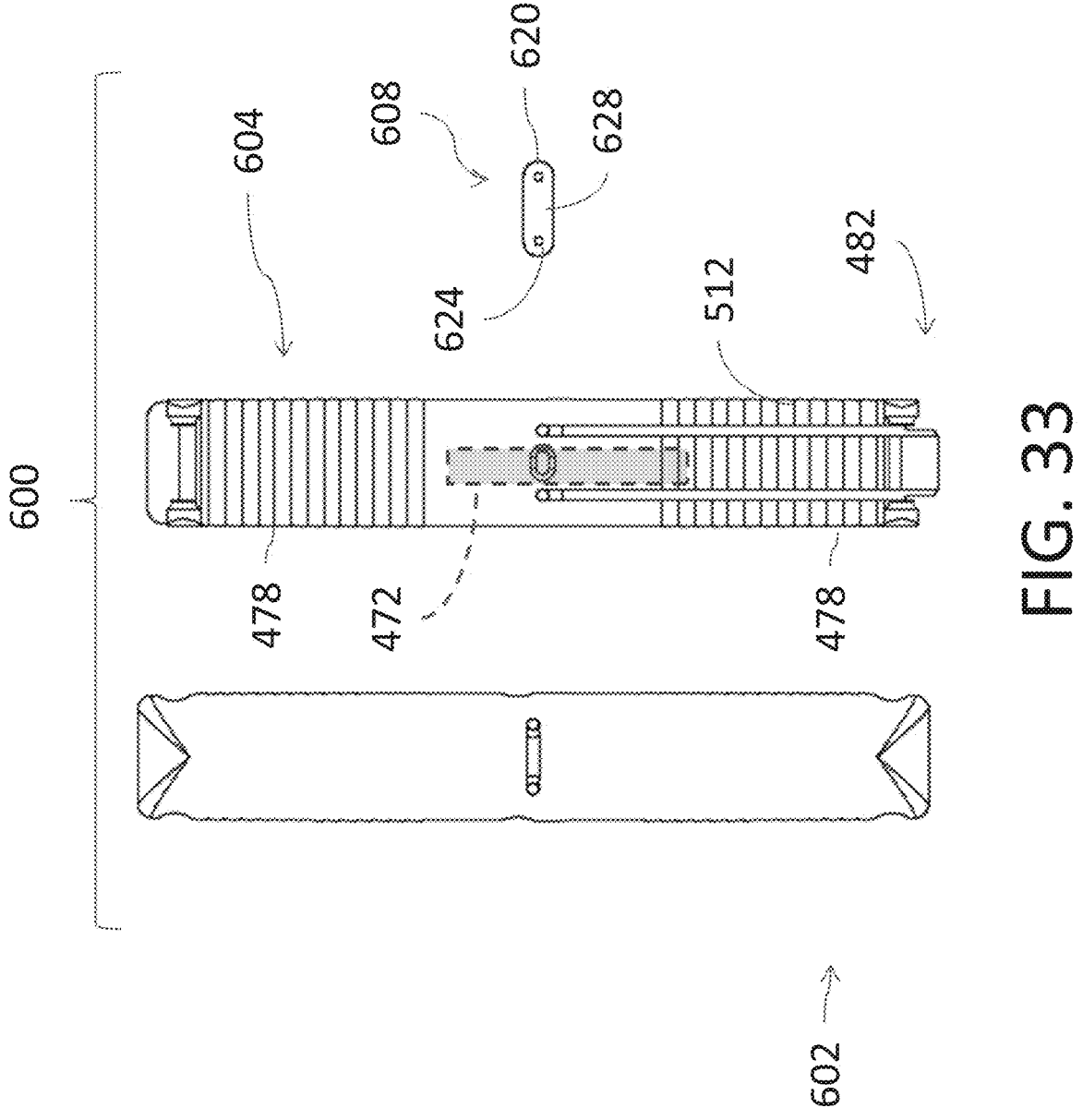
Figure 34:
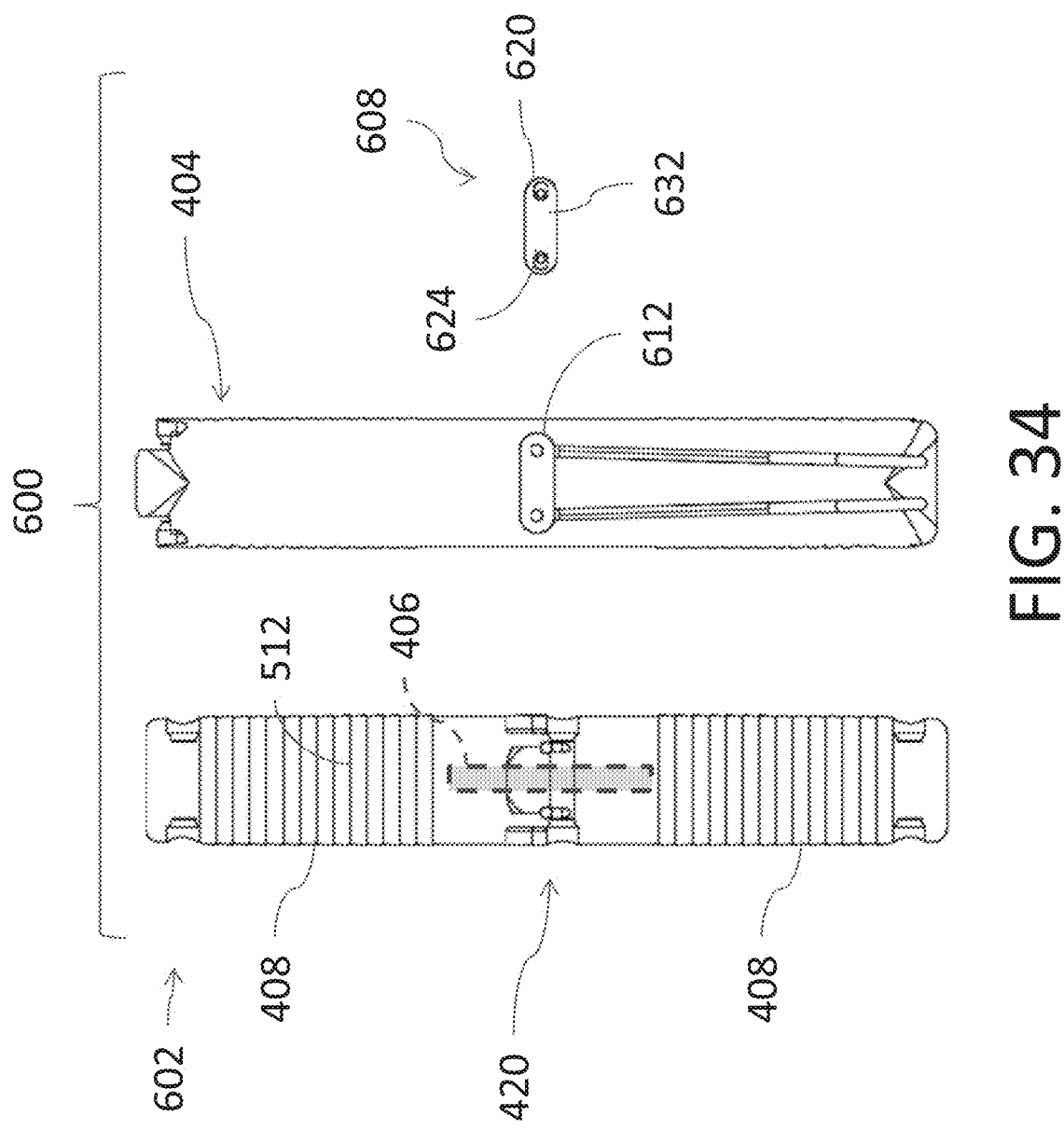

FIG. 31 shows that both the first and the second side 628, 632 can be curved. In one embodiment, the first side 628 comprises a concave curve when viewed from a side spanning between the two sides 628, 632, e.g., from a lateral side 636. The lateral side 636 can be disposed transverse to the longitudinal axis of the second member 604. The lateral side can be long enough to accommodate two apertures 624. The concave curve on the first side 628 can provide clearance between the suture retainer 608 and a bottom portion of the recess 612 such that the retainer 608 can be secured to the second member 604 without requiring excessive compression of the suture. In one embodiment, a knot is disposed between the suture retainer 608 and the bottom portion of the recess 612. Placement of the suture retainer 608 over the knot disposed between the suture retainer 608 and the second member 604 in the recess 612 holds the knot to prevent the knot from loosening.

FIG. 31 shows that the second side 632 of the suture retainer 608 can have a convex profile as viewed from the lateral side 636. The convex profile can be configured to match the curvature of the side of the second member 604 that is opposed to the tissue facing side, e.g., opposite to the side of the member 604 having the barbs 512. This convex profile allows the suture retainer 608 to be nested in the recess 612 in a manner providing reduced to no discontinuities in the curvature of the side of the prosthesis 600 disposed away from the valve engaging middle portion thereof. By reducing or eliminating discontinuities sites for blood clotting or tissue engagement are reduced or eliminated. The second side 632 also can have a concave profile when viewed in a cross-section transverse to the longitudinal axis of the suture retainer 608, e.g., a cross-section perpendicular to the lateral side 636. The concave profile provides space for a span of the suture, e.g., a knot formed in the suture, to be disposed. The concave profile in the transverse cross-section of the second side 632 allows the suture span to be disposed on the side of the prosthesis 600 disposed away from the valve engaging middle portion to be protected and partially or fully recessed in the side profile of the prostheses 600.

The prosthesis 600 is advantageous in that it need not span between the first member 602 and the second member 604. In the prosthesis 600 the sutures span the members 602, 604 and secure them together. This can reduce procedure time in that there is no need to align projections such as the member 416 with additional apertures in the member 602 and 604. Eliminating the apertures associated with the connector 414 provide in the embodiment of FIG. 5 also makes the members 602, 604 more rigid than the members 400, 404 which can improve the grip of these members on the heart valve leaflets. Advantageously the suture 412 is a tension member that acts as a connector in the prosthesis 600.

Figure 35:
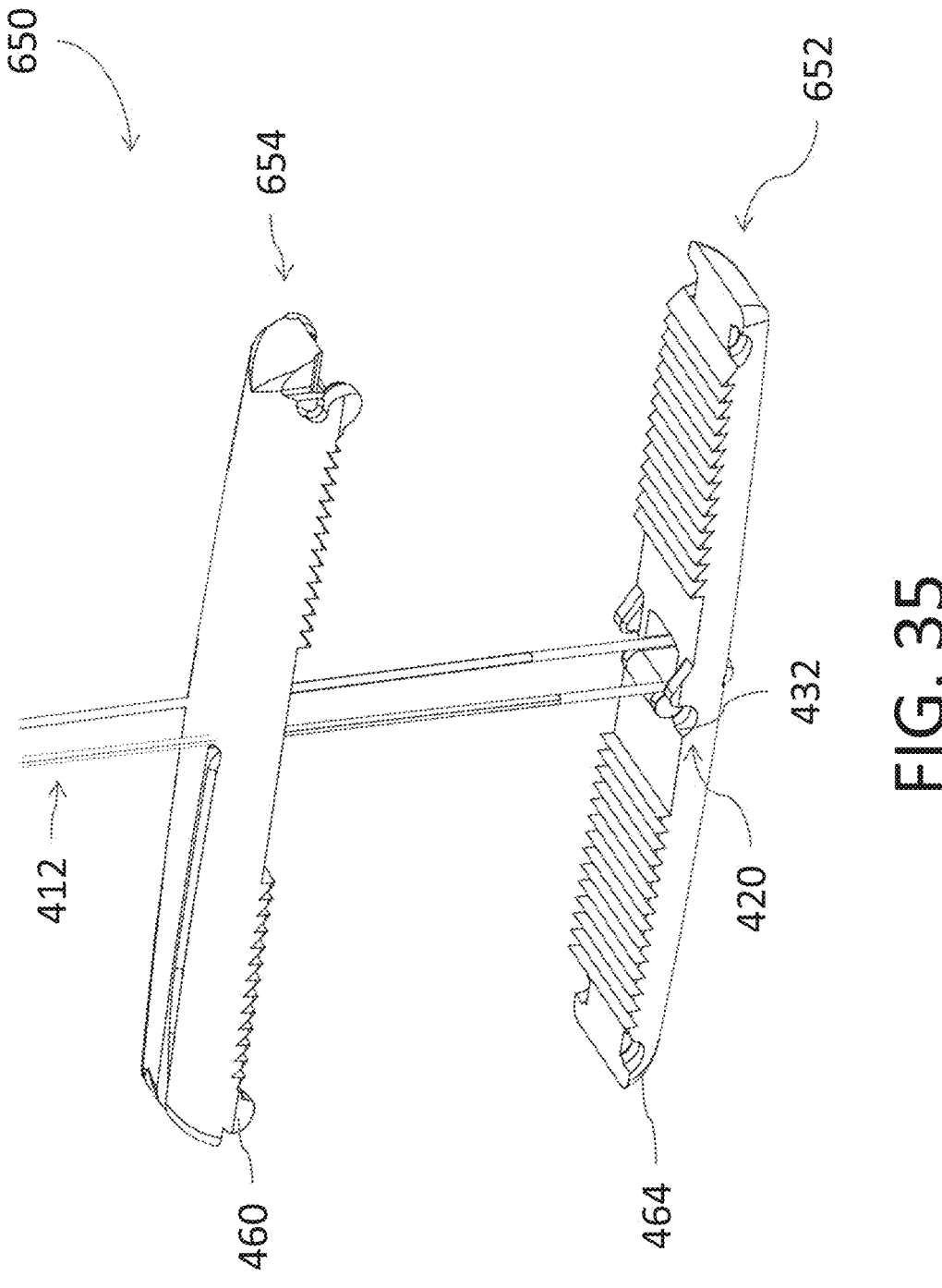
FIG. 35 shows another embodiment of a heart valve prosthesis having distal and proximal plates secured by a suture.
Figure 36:
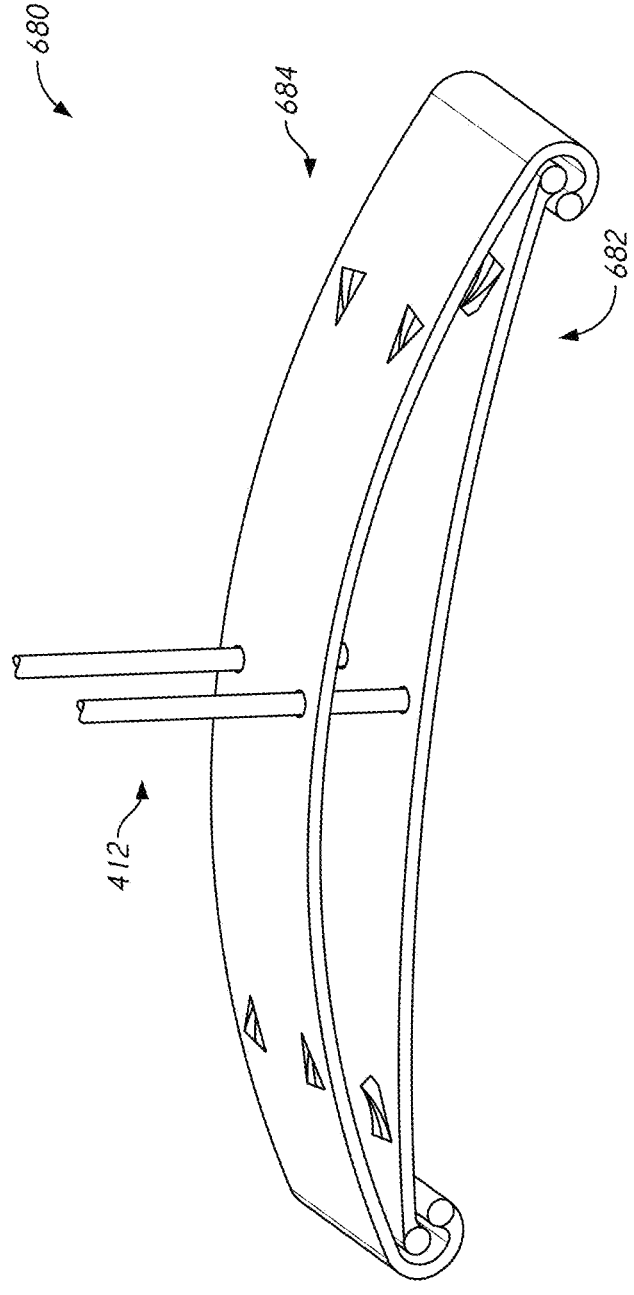
FIGS. 36-41 show another embodiment of a heart valve prosthesis employing one or more resilient members to trap valve leaflet tissue and to secure the prosthesis.

FIG. 35 shows a prosthesis 650 that is simplified compared to the prosthesis 108. The prosthesis 650 includes a first member 652 and a second member 654. Unlike the prosthesis 108, in the prosthesis 650 the connector 414 with the member 416 has been eliminated. In addition, because the connector 414 has been eliminated the recess 528 and the apertures configured to receive the members 416 of the connector 415 also can be eliminated. In this embodiment, the suture 412 alone acts as a connector. The first plate and second plate can be placed in the same manner described above in connection with FIGS. 21-30. After the second member 652 is placed against the side of the valve in the right atrium one or more tight knots can be formed in the suture 412 against the side of the second member 654 opposite the interface between the valve and the prosthesis 650. The knot or knots can be formed, advanced or tightened by the first elongate member 172. In one variation, the suture 412 can comprise a wire. The wire can be cinched, e.g., by twisting adjacent strands, to provide a secure connection between the first member 652 and the second member 654.

VI. Additional Embodiments Including Flexing Members

FIGS. 36-41 illustrate a heart valve prosthesis 680 that include the suture 412 and first and second flexing members 682, 684 that are assembled within the patient to secure a heart valve.

The first member 682 is configured to be advanced into a first heart chamber in a manner similar to that discussed above. The first member 682 has a central portion 686 to be disposed adjacent to a line of coaptation of two adjacent heart leaflets and peripheral portions 690 separated from one another by the central portion 686. The peripheral portions 690 are adapted to be placed into direct contact with the two adjacent heart leaflets. For example, the peripheral portions 690 can include one or more barbs 694 to engage the leaflet tissue. The first member can include apertures 698 to allow spans of the suture 414 to extend through the first member 682.

The second member 684 is configured to be advanced into the second heart chamber. The second member has a central portion 702 configured to be disposed adjacent to the line of coaptation of the two adjacent heart leaflets and peripheral portions 706. The peripheral portions 706 are configured to be placed into direct contact with the two adjacent heart leaflets. The second member 684 is separate from the first member 682, e.g., for delivery and for placing a heart valve leaflet therebetween. A tissue-engaging side 710 of the second member 684 has a concave arch 714 that joins together the peripheral portions 706 of the second member 684.

At least one of the first member 682 and the second member 684 is deformable to allow at least a portion of the first member 682 to be interposed between a base 712 of the arch 714 and an apex 718 of the arch 714. The base 712 of the arch 714 can include curled ends 722 that are configured to engage the first member 682 to promote deflection and/or deformation of the first and/or the second member 682, 684. For example, a portion of the curled end 722 can provide a concave space within which end portions of the first member 682 can be received and retained.

Figure 37:
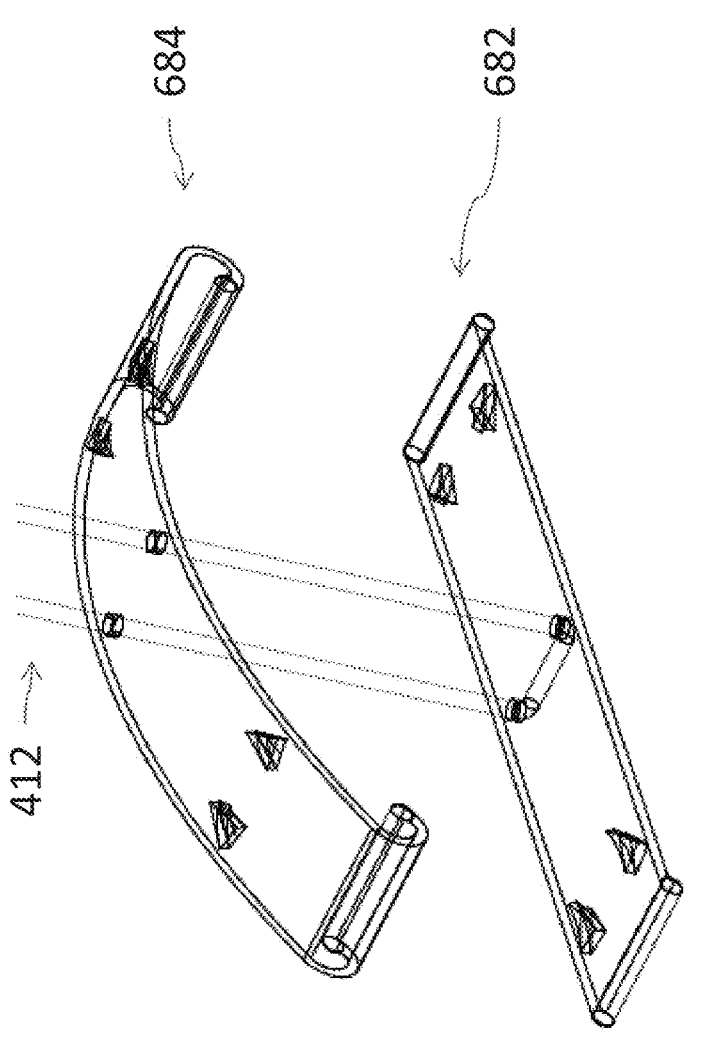
Figure 38:
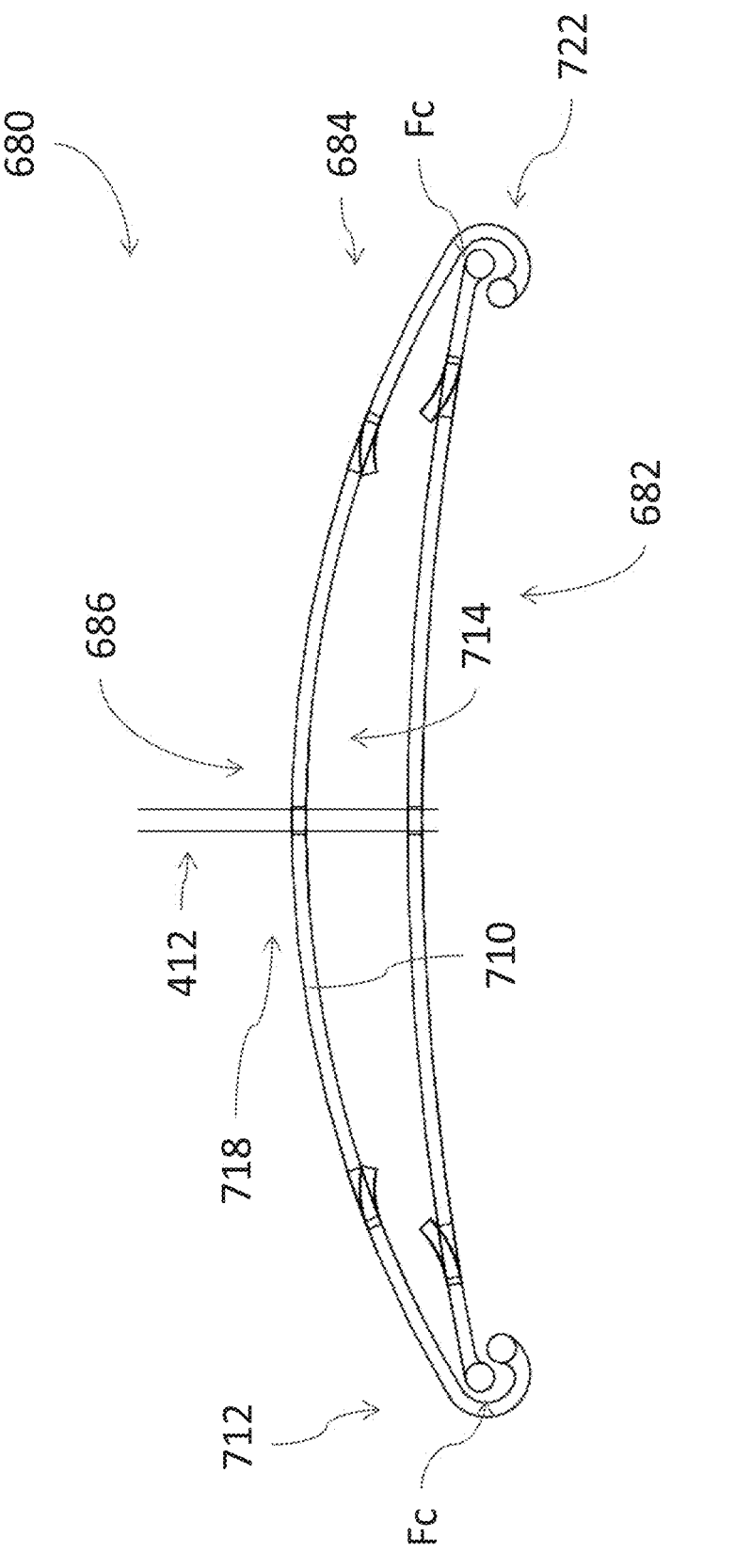
Figure 39:
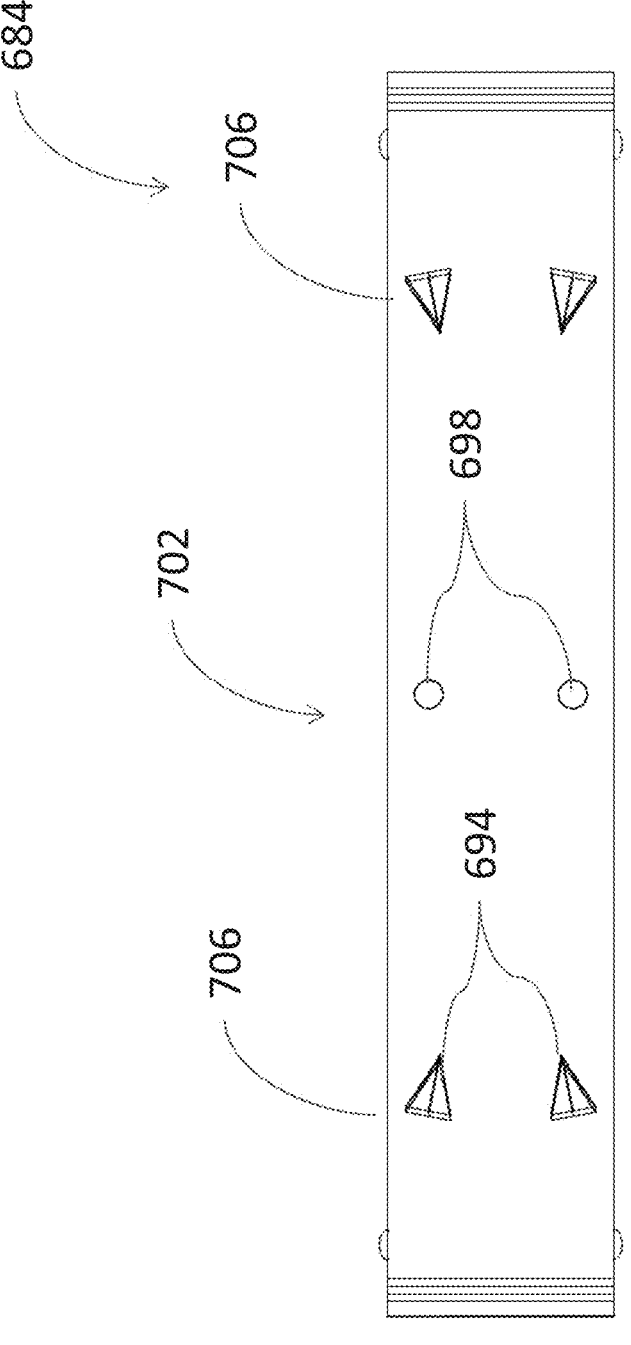
Figures 40, 41:
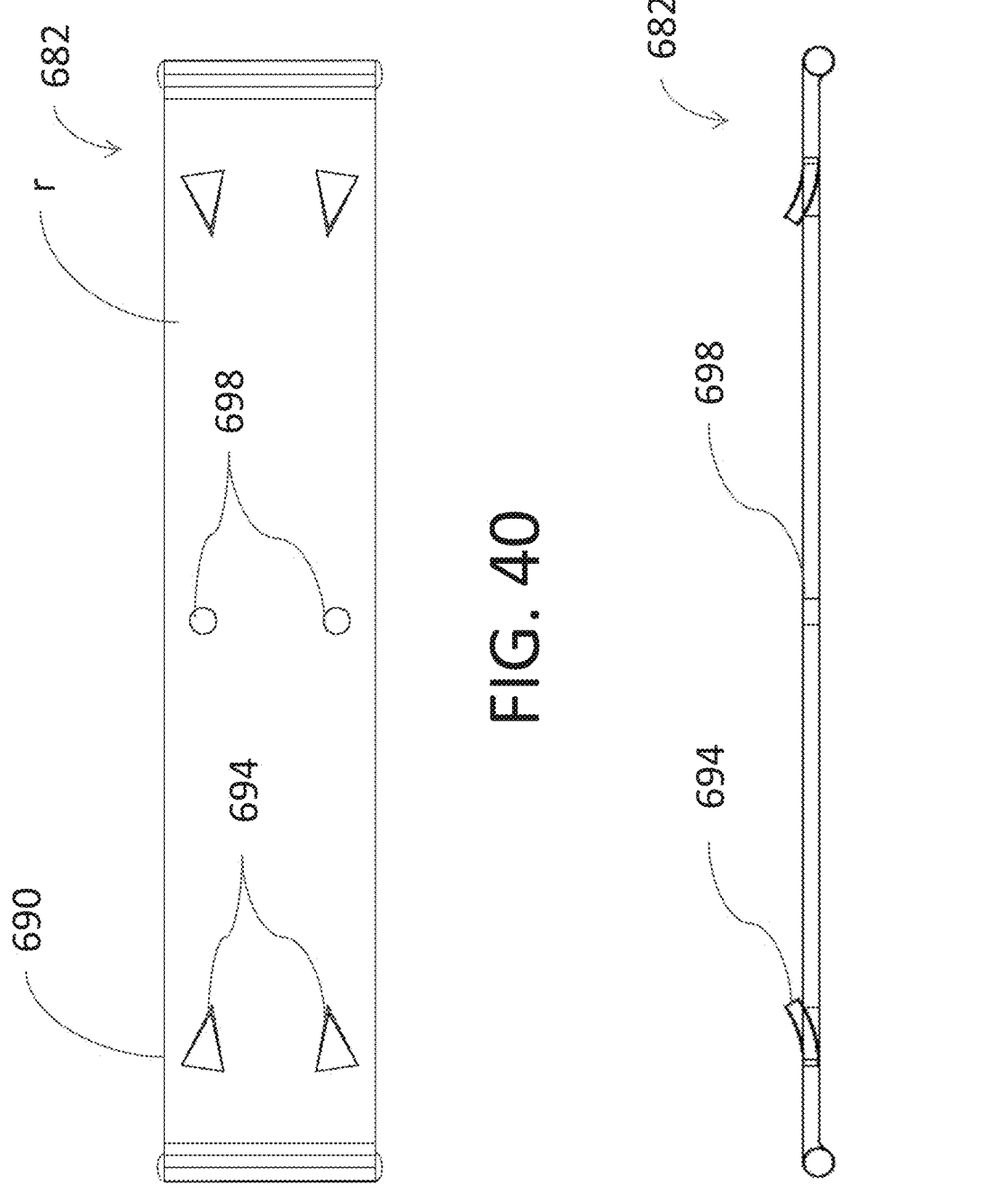

FIGS. 37 and 38 show how the first member 682 can be secured to the second member 684. In one embodiment, the second member 684 has an arched profile prior to being connected to the first member 682. The first member 682 can be substantially straight between ends thereof and between the peripheral and central portions 706, 702 during delivery and upon initial engagement with the second member 682. Further tension on the suture 412 causes the second member 684 to flex such that the concave arch 714 flattens to some extent. This expands the distance between the curled ends 722. This further tension also bends the first member 682 such that the distance between the ends thereof is reduced. Further tension on the suture 412 continues this lengthening of the second member 684 and shortening of the first member 682 until the ends of the first member 682 can be advanced past the curled ends 722 into the concave arch 714 to the position shown in FIG. 38. Once so received the first and second members 682, 684 can relax from the most deformed state of delivery to a less deformed state.

In one variation, the suture 412 can comprise a wire. The wire can be cinched, e.g., by twisting adjacent strands, to enhance the connection between the first member 682 and the second member 684.

FIG. 38 shows that in one embodiment when the first member 682 is secured to the second member 684 the first member 682 is flexed. As a result, a compression force Fc is provided in a space between the first member 682 and the second member 684 where leaflet tissue can be disposed. The engaged state of FIG. 38 illustrates multiple modes of securing leaflet tissue by the prosthesis 680. The barbs 694 can engage the leaflet tissue. Also, a span of leaflet tissue extending through the space where the force Fc is felt can be gripped by the force Fc.

FIGS. 36-41 illustrate embodiments where one or both of proximal and distal members can flex. In other embodiments, the proximal plate is rigid and includes a concave space into which ends of a flexing or deformable distal plate can be received. For example, the second member 684 could be made rigid and the first member 682 could be flexible. In one embodiment, one of the members 682, 684 is plastically deformable upon movement into engagement with the other of the members 682, 684 to provide a secure connection therebetween.

Figure 42:
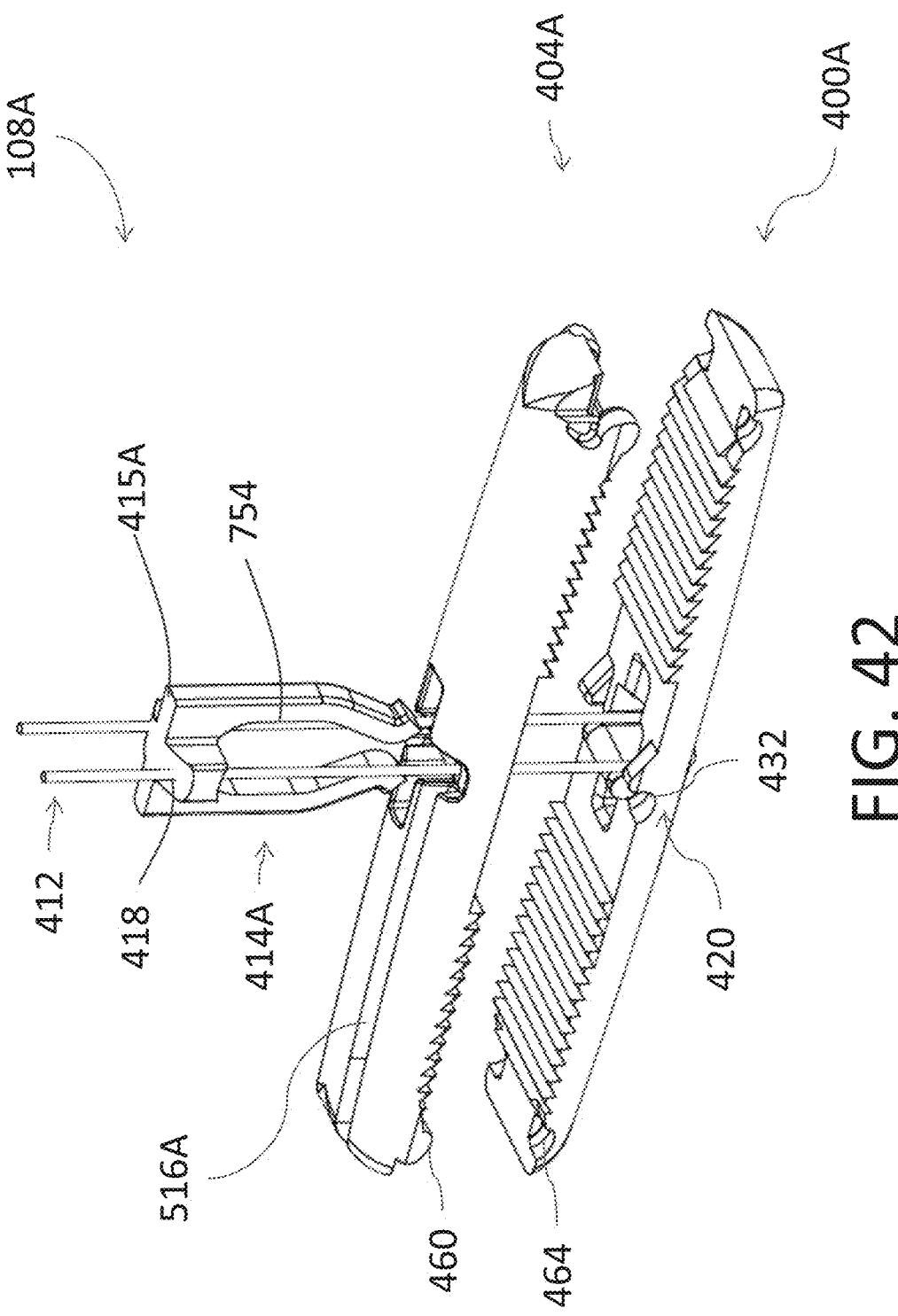
FIGS. 42-43 show another embodiment in which an elastic clip structure is used to secure proximal and distal elongate members, which can be plate bodies.
Figure 43:
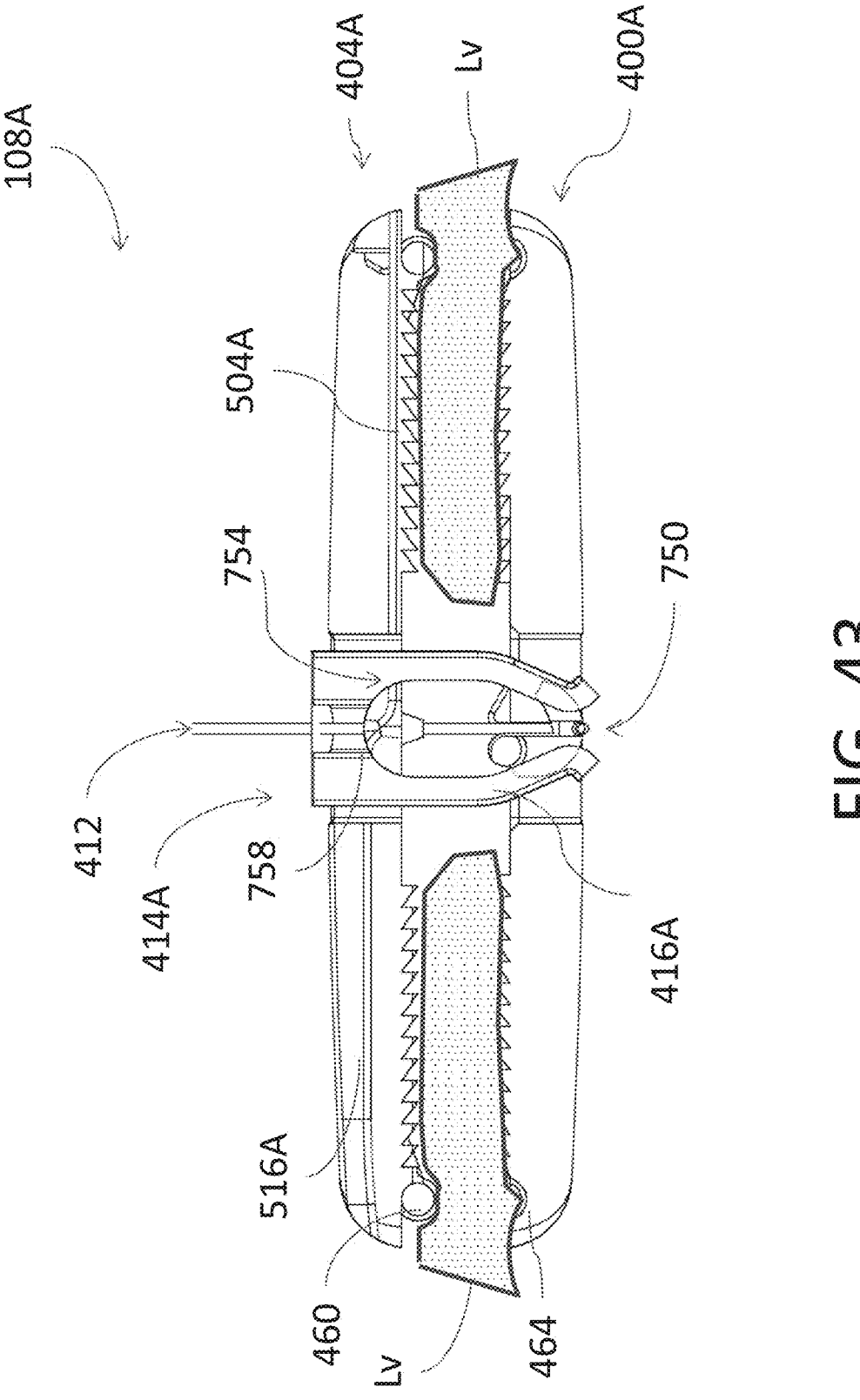

FIGS. 42 and 43 show another embodiment of a prosthesis 108A that is similar to the prosthesis 108 except as described differently below. The prosthesis 108A includes first and second members 400A, 404A. The first member 400A is generally configured to be disposed distal of the valve leaflets, e.g., distal to two leaflet portions of a tricuspid valve. A connector 414A is provided that can secure the first and second members 400A, 404A together.

The connector 414A has a proximal body 415A. The proximal body 415A is cross-shaped with a first span aligned with the longitudinal plane Lp of the members 400A, 404A and a second span transverse to the first span. The first span has a plurality of, e.g., two, elongate member 416A extending therefrom. The elongate members 416A are shaped to have a narrow opening 750 disposed away from the proximal body 415A. The inner edges of the members 416A form a curved profile 754 that facilitates engagement of the connector 414A to the members 400A, 404A.

In one embodiment, each of the members 400A, 404A has a curved, e.g., a semicircular hub disposed to engage the curved profile 754. An end 758 of the profile 754 adjacent to the proximal body 415A includes a semicircular profile that allows the semicircular hub of the proximal member 404A be nested therein. Between the end 758 and the opening 750 the curved profile 754 is able to engage the semi-circular hub of the distal member 400A over a range of positions. This allows a valve leaflet Lv (shown in FIG. 43 schematically) with a thicknesses over a range, e.g., from 1-5 mm, from 2-3 mm, 2 mm or 3 mm to be trapped between the members 400A, 400B while the connector 414A securely connects the member 400A, 404A as shown in FIG. 43. FIG. 43 suggests that the members 416A can return to an undeflected position in which the semi-circular hub of the member 400A does not deflect them outward. If the valve leaflet Lv is thick the members 416A may be somewhat deflected away from a plane containing the sutures and disposed transverse to the prosthesis 108A (e.g., left and right in the view shown in FIG. 43). The deflected state results in a compressive force being applied by the members 416A to the hub of the first member 400 which can enhance friction at the location of connection and correspondingly the connection The second span extends generally transverse to the longitudinal plane Lp of the members 400A, 404A. The second span comprises apertures 418 configured to permit a span of the suture 412 to extend therethrough. In one method, the members 400A, 404A are secured using the connector 414A. Then, the knot portions 412A, 412B are advanced to further secure the connector 414A to the members 400A, 404A. The suture 412 is then severed proximal of the knot portion 412B. One or both of the knot portions 412A or 412B are options with the connectors 414, 414A.

FIGS. 42 and 43 shows that in some applications the projections 460 and the recesses 464 may not overlap on a transverse axis. But the projections may dig into the leaflet Lv to some extend gripping it. Also, compression between the members 400A, 404A may cause the leaflet tissue to be deformed into the recess 464 such that lateral stability is still provided by theses or similar features.

In one variation of the prosthesis 108A, the connector 414A can be configured as a wire. The wire can be cinched, e.g., by twisting adjacent strands, to provide a secure connection between the first member 400A and the second member 404A.

VII. Additional Embodiments Including Looped Connectors

Figure 44:
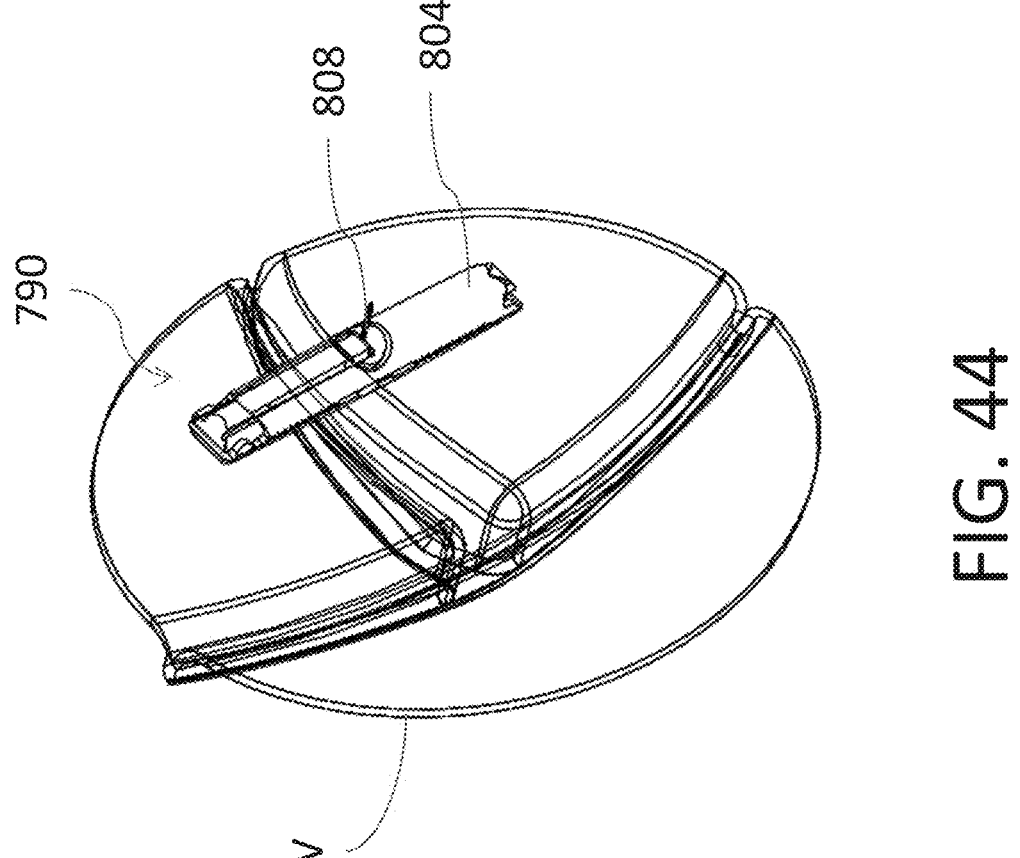
FIG. 44 is a perspective view of a heart valve having a heart valve prosthesis implanted thereon.

FIG. 44 shows a heart valve prosthesis 790 disposed in a valve V. The heart valve prosthesis 790 is similar to the prostheses hereinbefore described including, for example, the prosthesis 108 and the prosthesis 650. The description that follows supplements and can be combined with the descriptions of these and other similar prostheses described herein.

Figure 45:
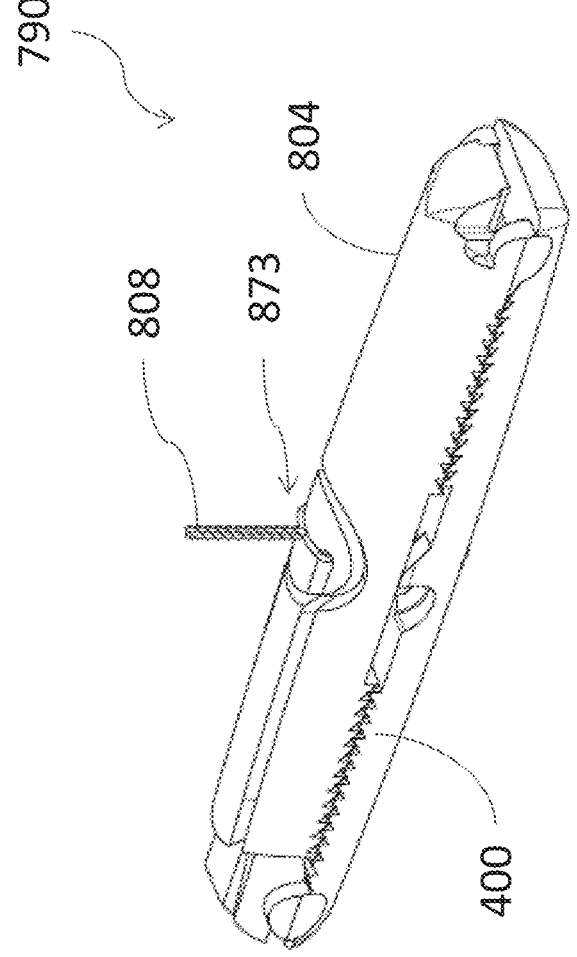
FIG. 45 is a perspective view of one embodiment of a heart valve prosthesis configured to be secured with a wire connector.

Referring to FIG. 45, the heart valve prosthesis 790 includes a first member 400 and a second member 804. The first member 400 is a prosthesis component that can be delivered in a catheter system separately from, e.g., before and in some cases sequentially with the second member 804. The first member 400 can be delivered out of the same or out of a different catheter than the second member 804. The first member 400 and the second member 804 can be coupled with a connector 808, which can comprise a loop-shaped member. The connector 808 can be looped around the first member 400. The connector 808 can be actuated to cause the second member 804 to be compressed toward or against the first member 400. The connector 808 can comprise a wire structure that can be twisted to secure the second member 804 to the first member 400.

FIG. 45 shows the heart valve prosthesis 790 in an engaged configuration. In this configuration, the first member 400 and the second member 804 are aligned. A longitudinal axis of the first member 400 is aligned, e.g., parallel to, a longitudinal axis of the second member 804. The longitudinal axis of the first member 400 is distal of (in the view, below) the longitudinal axis of the second member 804. This allows the first member 400 to be placed distal of a tricuspid valve in a right ventricle of a heart while the second member 804 is proximal of the tricuspid valve, in a right atrium of the heart. The longitudinal axes of the first member 400 and the second member 804 can be arranged perpendicular to a line of coaptation of the valve V (see FIG. 44).

Figure 46:
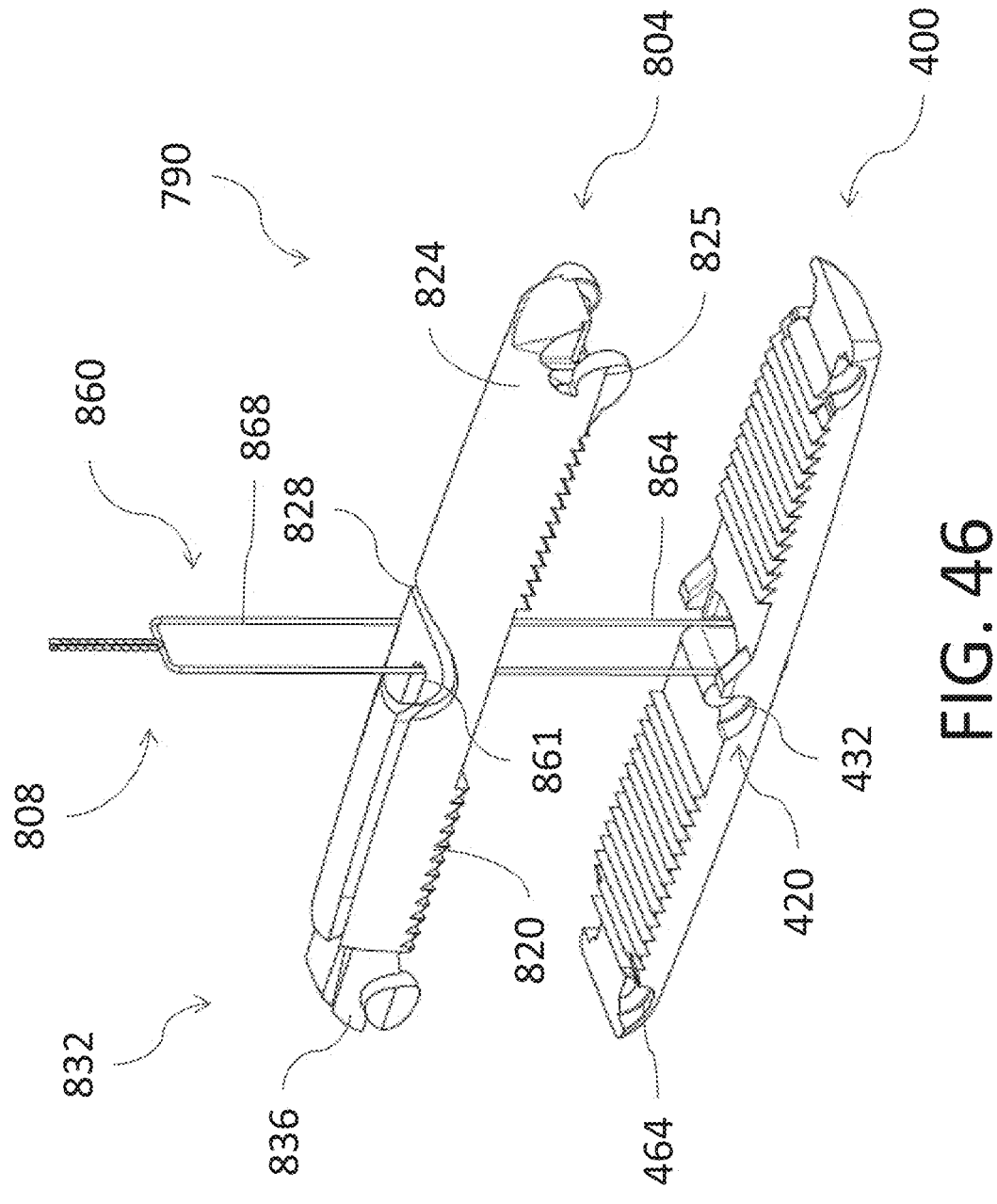
FIG. 46 is a partially assembled view of the heart valve prosthesis of FIG. 45.

FIG. 46 shows in greater detail the heart valve prosthesis 790 prior to application to the valve V. In certain delivery states (discussed further below in connection with FIGS. 53G and L), the first member 400 and the second member 804 are deployed out of a delivery system and the first member 400 and the second member 804 are separated from each other by a gap much larger than the thickness of the leaflets of the valve V. In these states, tissue facing surfaces of the first member 400 and the second member 804 are spaced away from each other. A loop-shaped tension member 860 is disposed through apertures 401 in the first member 400 and apertures 861 in the second member 804. The apertures 401 can be the same as described above. The aperture 861 can be similar to the openings 500, described above.

The second member 804 can be formed to couple with a control member in a low profile manner. For example, the second member 804 can include a low profile portion 836 at one peripheral portion. The low profile portion 836 can have a surface that is recessed relative to a surface opposite 824 a tissue engaging surface 820. The low profile portion 836 can be recessed by an amount that is the same as or more than a wall thickness of the control body as discussed further below.

The loop-shaped tension member 860 that can be routed through openings (e.g., apertures 861) in the second member 804 and openings (e.g., apertures 401) in the first member 400. The loop-shaped tension member 860 can be routed through a channel similar to the suture channel 442. A first enclosed end 864 can be routed through the channel on a side of the first member 400 opposite the tissue engaging side of the first member 400. The loop-shaped tension member 860 can be routed from the first member 400 through apertures 861 in the second member 804. A second end portion 868 of the loop-shaped tension member 860 can extend from the first enclosed end 864 to a second enclosed end 872 at the second end portion 868. The second end portion 868 can extend proximally of the surface opposite 824 of the second member 804. The second end portion 868 can be enclosed such that the loop-shaped tension member 860 can be connected to a control member as discussed further below.

Assembly of the first member 400 to the second member 804 can be achieved by reducing the distance between the first enclosed end 864 and a second enclosed end of the loop-shaped tension member 860. In a delivery assembly configuration, the distance can be defined between the first enclosed end 864 and the second enclosed end 872. In an intra-cardiac assembly configuration on the heart valve, the distance can be defined between the first enclosed end 864 and a distal portion of a twisted zone 873 (see FIG. 45).

The second member 804 also can include a control body interface. For example the surface 824 which is disposed opposite the tissue engaging surface 820 can include a torque control groove 828 that can mate with a control member, e.g., with a second elongate member 944 of the delivery system 792 discussed further below.

Figures 47, 48:
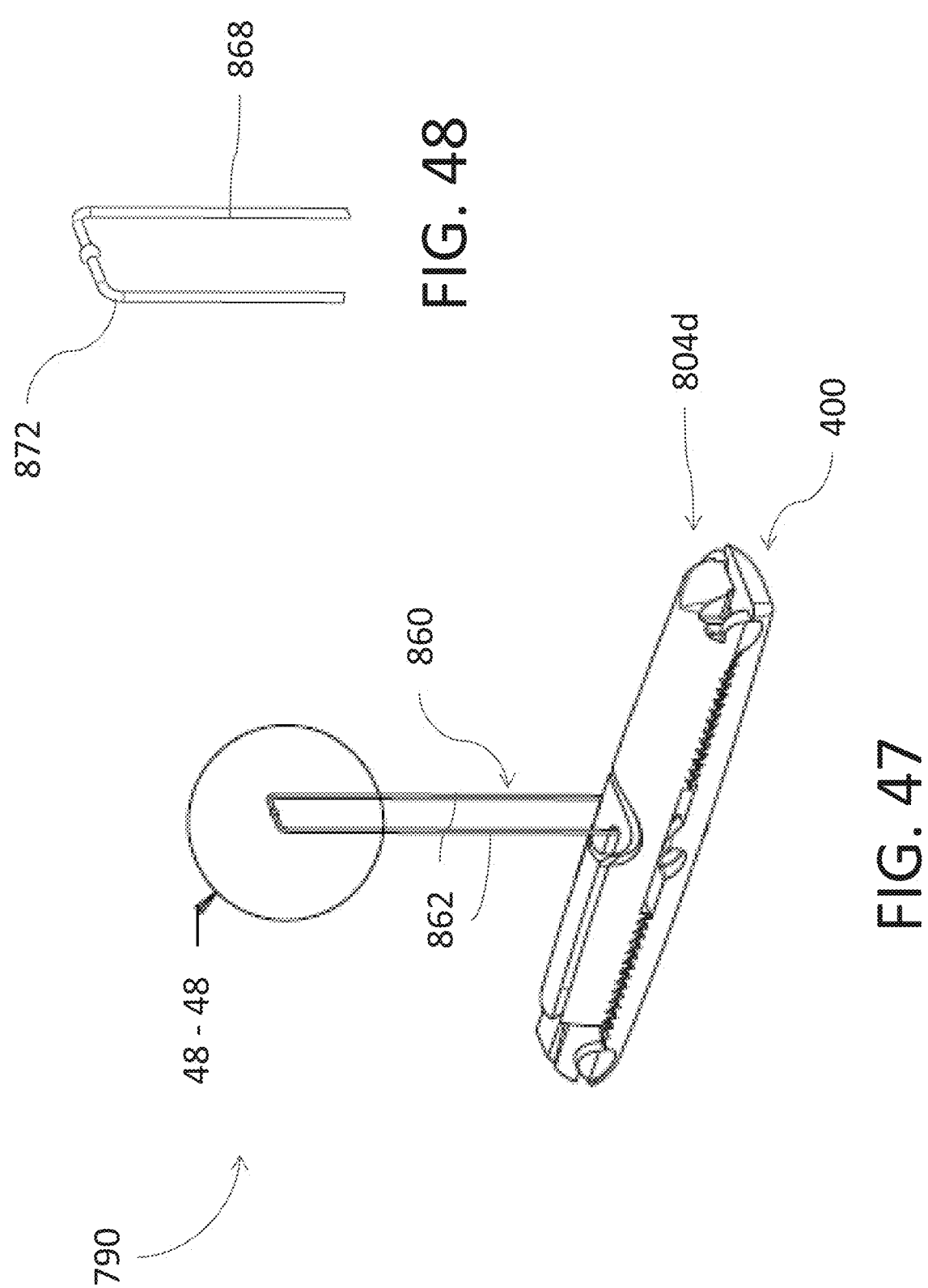
FIG. 47 is a perspective view of an embodiment of a heart valve prosthesis in a partially assembled state.
FIG. 48 is a perspective view of a wire connector comprising a second end portion having a second enclosed end.

FIGS. 47 and 48 show further details of the heart valve prosthesis 790 with the first member 400 and the second member 804 engaged with one another. This configuration can be provided by a control body engaging the surface 824, e.g., in a torque control groove 828, as discussed further below. In this configuration the loop-shaped tension member 860 remains in a delivery state with adjacent strands 862 of the loop-shaped tension member 860 aligned and spaced apart from each other. The loop-shaped tension member 860 can include a second enclosed end 872 at the second end portion 868. The loop-shaped tension member 860 can be enclosed at the second enclosed end 872 by welding or otherwise securing the free ends of the loop-shaped tension member 860 together.

As discussed further below, the adjacent strands 862 can be joined, e.g., can be twisted together to create tension in the first enclosed end 864. A plurality of twists draws the first member 400 and the second member 804 closer together. Each subsequent twist can draw the first member 400 and the second member 804 closer together and/or create more tension in the loop-shaped tension member 860 such that greater compression can be created between the first member 400 and the second member 804. In some methods discussed further below the loop-shaped tension member 860 will fracture in the first enclosed end 864, in the second end portion 868, or between these portions close to the surface 824 opposite the tissue engaging surface 820. In one method, the loop-shaped tension member 860 is twisted at least two times prior to fracture. In one method, the loop-shaped tension member 860 is twisted at least three times prior to fracture. In one method, the loop-shaped tension member 860 is twisted at least eight times prior to fracture. In one method, the loop-shaped tension member 860 is twisted at least twenty times prior to fracture.

Figures 49, 50:
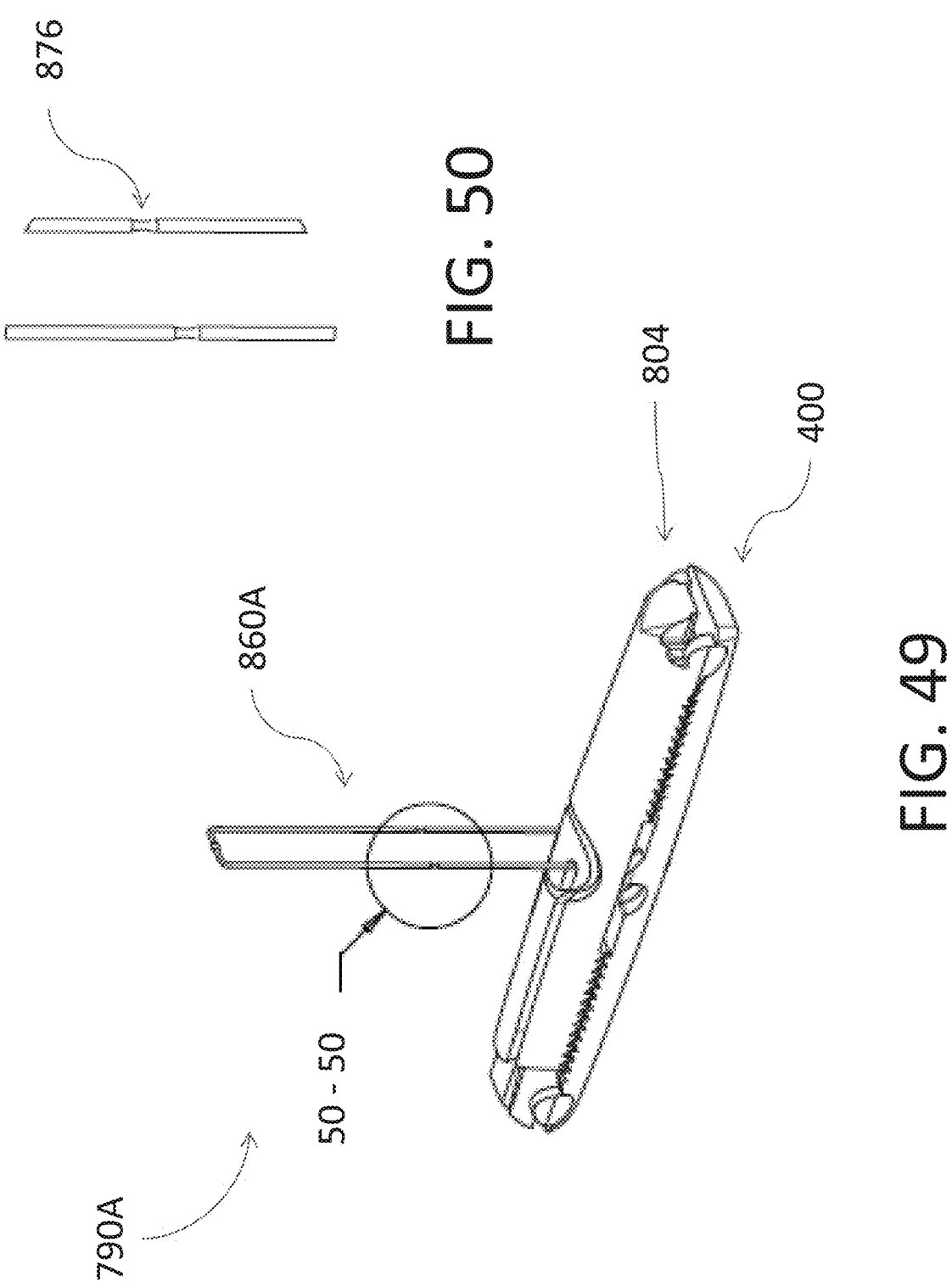
FIG. 49 is a perspective view of another embodiment of a heart valve prosthesis having a wire connector configured for controlled separation from a delivery system.
FIG. 50 is a detail view of the wire connector of the embodiment of FIG. 49 showing a fracture zone.
Figure 51:
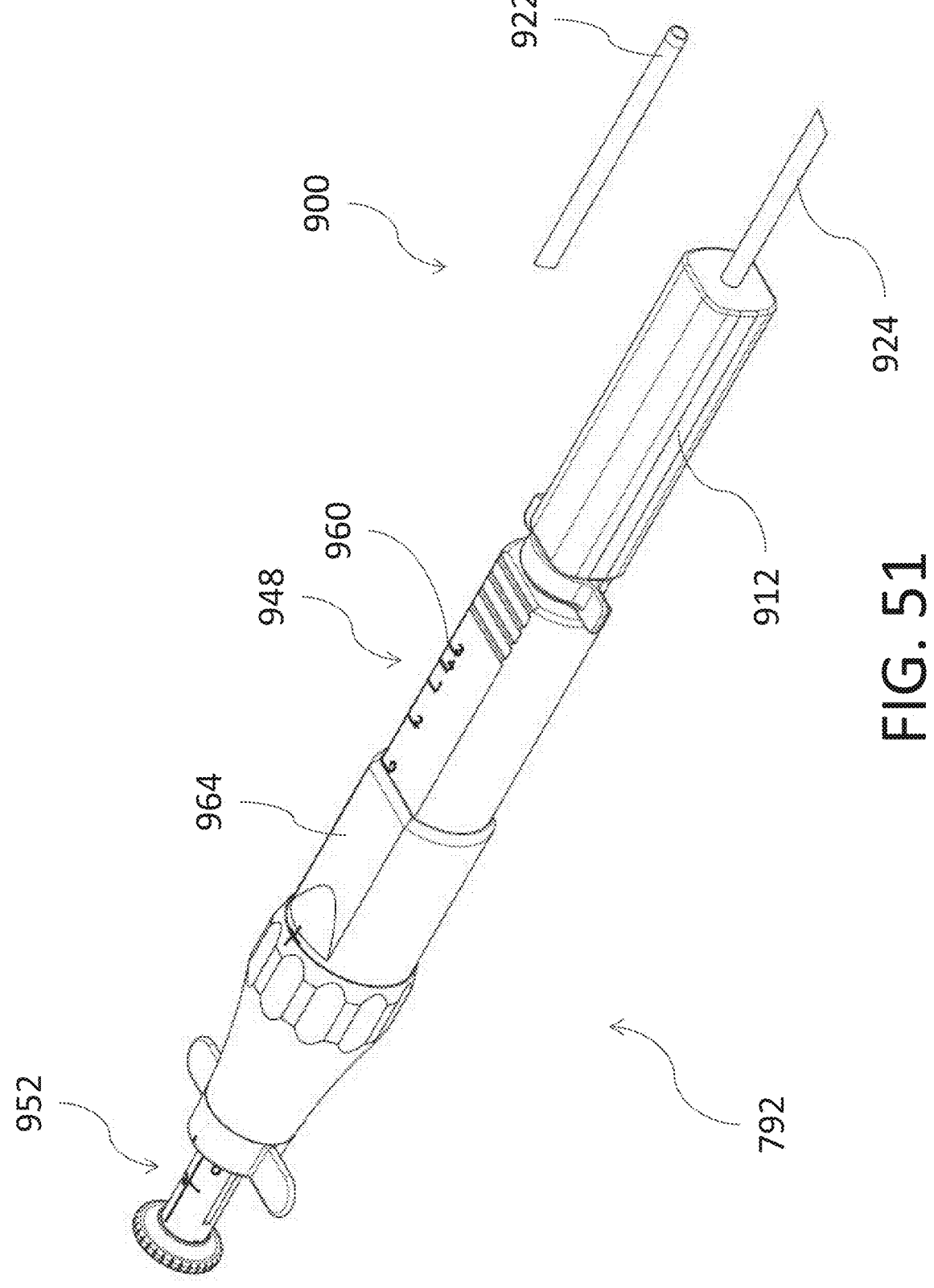
FIG. 51 is a perspective view of one embodiment of a delivery system for deployment and assembly of plate-like members of a heart prosthesis of certain embodiments disclosed herein.

FIGS. 49 and 50 show a heart valve prosthesis 790A similar to the heart valve prosthesis 790 except as described differently below. The heart valve prosthesis 790A can include a loop-shaped tension member 860A that is configured for controlled fracture. The loop-shaped tension member 860A includes a fracture zone 876 in the adjacent strands 862. The fracture zone 876 can include a necked-down portion of the adjacent strands 862. The necked-down region can focus stress such that the loop-shaped tension member 860A will fracture in the fracture zone 876. The loop-shaped tension member 860A, e.g., in the adjacent strands 862, can focus stress in other ways than reducing the thickness of the strands. In one embodiment, the diameter of the loop-shaped tension member 860A in the fracture zone 876 is between 40 and 95 percent of the diameter adjacent to the fracture zone 876. In one embodiment, the diameter of the loop-shaped tension member 860A in the fracture zone 876 is between 50 and 85 percent of the diameter adjacent to the fracture zone 876. In one embodiment, the diameter of the loop-shaped tension member 860A in the fracture zone 876 is between 60 and 75 percent of the diameter adjacent to the fracture zone 876.

FIGS. 51-56 show aspects of a delivery system 792 that can be used to deliver, deploy, and secure the heart valve prosthesis 790 or the heart valve prosthesis 790A to the valve V. The delivery system 792 includes a guide catheter 900, a prosthesis member manipulator 948, and a connector manipulator 952. The guide catheter 900 can be inserted into the patient initially such that a distal end 922 is disposed within the vasculature or within the right atrium of a heart. A low profile catheter body can extend proximally from the distal end 922 to a proximal portion 924. The proximal portion 924 can be coupled with a hub 912 into which control members of the delivery system 792 can be inserted. For example, the hub 912 can include an aperture having a hemostatic valve 928 disposed therein. The hemostatic valve 928 is shown in FIG. 57A. The hemostatic valve 928 can be configured to permit the control bodies to be inserted into the hemostatic valve 928 and distally thereof toward the distal end 922 of the distal portion 920.

The delivery system 792 includes a housing comprising a prosthesis member manipulator 948 configured to move the first member 400 and the second member 804 relative to the distal end 922 of the guide catheter 900. Movement of the first member 400 and the second member 804 can be provided by relative motion between a distal grip 960 and a proximal grip 964 of the prosthesis member manipulator 948. For example, the distal grip 960 can be coupled with the guide catheter 900 such that holding the distal grip 960 steady can hold the distal end 922 steady. The proximal grip 964 can be coupled with the second member 804 such that moving the proximal grip 964 can move the second member 804 distally. If the distal grip 960 is held stationary while the proximal grip 964 is moved distally the first member 400 can be moved distally out of the distal end 922. Further motion of the proximal grip 964 distally relative to the distal grip 960 can move the second member 804 out of the distal end 922.

The delivery system 792 includes a connector manipulator 952 that is configured to secure a connector, e.g., the loop-shaped tension members 860, 860a, to the first member 400 and to the second member 804. The connector manipulator 952 can include a wire twister 1020 configured to twist the adjacent strands 862 about each other to increase tension in the loop-shaped tension member 860 to provide compression between the first member 400 and the second member 804.

Figure 52:
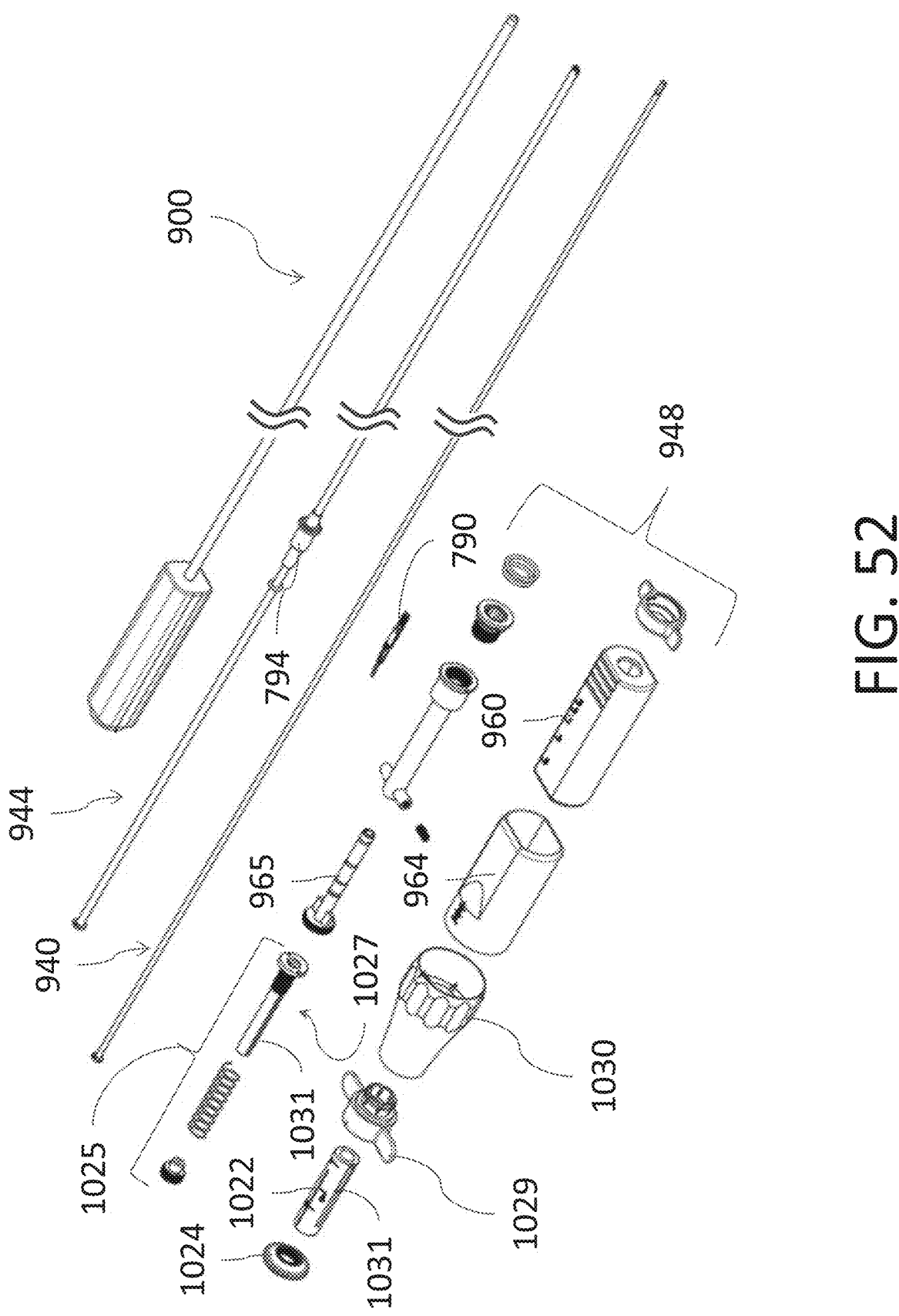
FIG. 52 is an exploded view of the delivery system of FIG. 51.

FIG. 52 shows components of the prosthesis member manipulator 948 that are disposed within or through or coupled with the distal grip 960 and the proximal grip 964. A first elongate member 940 can be provided to be coupled with a cap 1024 at a proximal end thereof and to be coupled with the loop-shaped tension member 860 at a distal end thereof. A second elongate member 944 can be hollow to be disposed over the first elongate member 940 such that the first elongate member 940 can rotate within the second elongate member 944. The second elongate member 944 can include a proximal end coupled with the proximal grip 964 such that advancement of the proximal grip 964 moves the second elongate member 944, e.g., distally relative to the distal grip 960. The first elongate member 940 and the second elongate member 944 are sometimes referred to herein as control bodies because the motion thereof controls one or more components of the heart valve prosthesis 790.

FIG. 52 shows the second elongate member 944 disposed through the loading capsule 794. As discussed further below, the loading capsule 794 is used to load the first member 400, the second member 804, and the loop-shaped tension member 860 into the guide catheter 900 for advancement into the patient. The loading capsule 794 can provide a connection between the prosthesis member manipulator 948 and the guide catheter 900 for ease of insertion and hemostatic operation.

The prosthesis member manipulator 948 also can include a tensioning mechanism 1025 to provide or enhance tension in the loop-shaped tension member 860 when the components of the heart valve prosthesis 790 are in the delivery system 792. As will be understood from the description herein the components of the heart valve prosthesis 790 are delivered in the delivery system 792 in other than their final assembled state. The components of the heart valve prosthesis 790 are assembled in a delivery state. The components are then at least partially disassembled within the heart and re-assembled using the delivery system 792. The tensioning mechanism 1025 facilitates this by providing or creating tension in the loop-shaped tension member 860 that is controlled. The tensioning mechanism 1025 can include a coil spring that acts on a tensioner 1027 to provide the desired tension. Further control can be provided by a locking mechanism 1029 disposed adjacent to the proximal end of the prosthesis member manipulator 948. The locking mechanism 1029 can affix the connector manipulator 952 to prevent inadvertent twisting of the loop-shaped tension member 860. Further, the locking mechanism 1029 allows tension to be applied to the loop-shaped tension member 860 by turning a knob 1030. The tension is provided as a result of a threaded connection between the knob 1030 and the tensioner 1027. This structure is similar to that described in connection with FIG. 4A which is incorporated here to supplement the description hereof. The tensioning allows the first member 400 to rotate relative to the second member 804 (between the positions of FIGS. 53E and 53F). After rotation, the tension can be relaxed allowing the first member 400 to separate from the second member 804 such that the second member 804 can be retracted (see FIG. 53G). The adjacent strands 862 are prevented from prematurely twisting and general alignment of the first elongate member 400 and the second elongate member 804 is maintained through key interfaces 1031 disposed between the bearing 1022 and the tensioner 1027 and between the wire twister and the bearing 1022. The locking mechanism 1029 can be released to allow the connector manipulator 952 to be activated. When the connector manipulator 952 is activated the cap 1024 can be turned to twist the adjacent strands 862. The locking mechanism 1029 can include a collet that is compressed upon rotational advancement of a knob of the locking mechanism 1029.

Figures 53A, 53B:
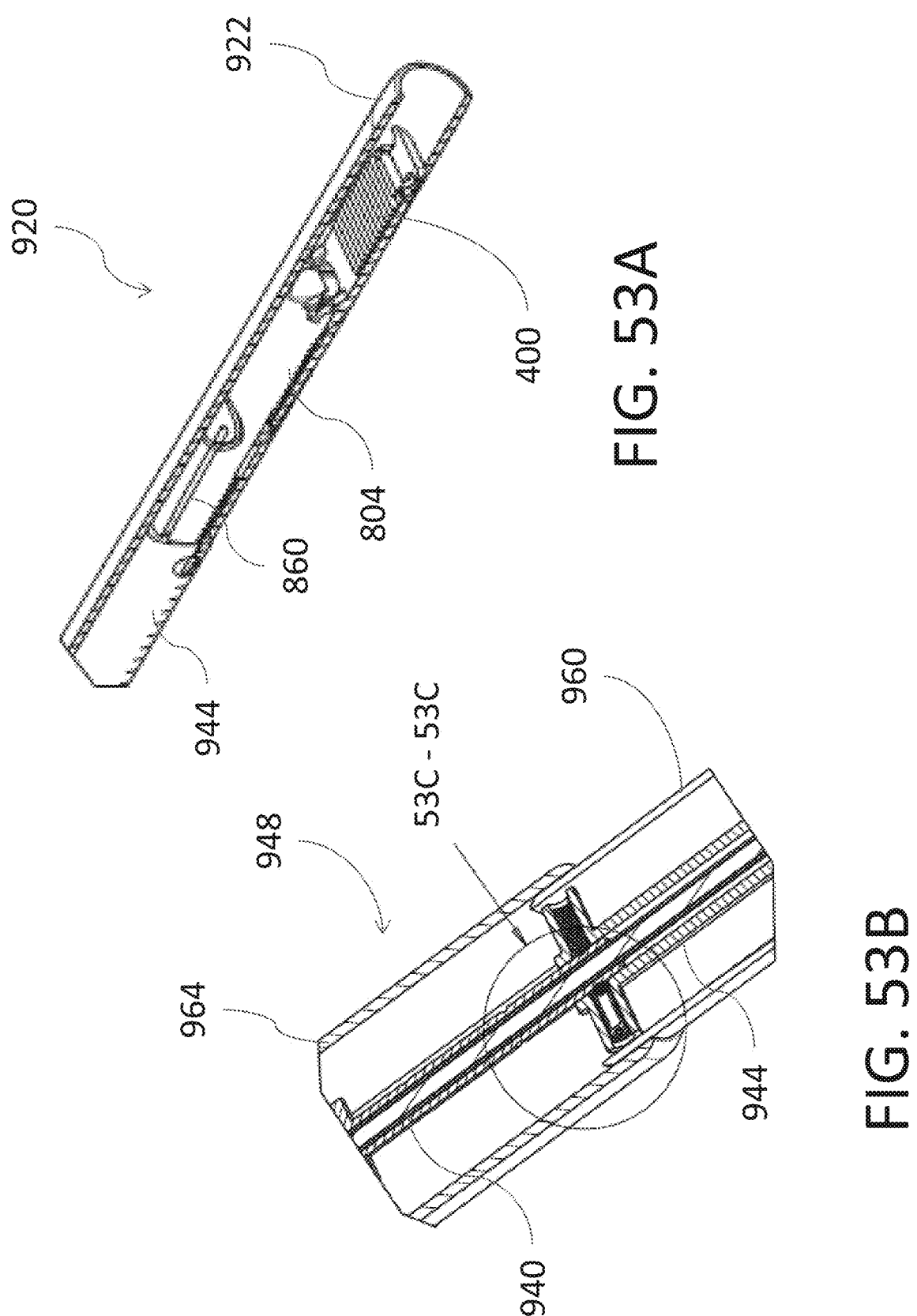
FIG. 53A is a cutaway view of a distal portion of the delivery system of FIG. 51, configured to deliver the heart valve prosthesis of FIG. 44.
FIG. 53B is a cross-sectional view of the delivery system showing a detent mechanism of a prosthesis manipulator for controlled delivery of the heart valve prosthesis.
Figure 53C:
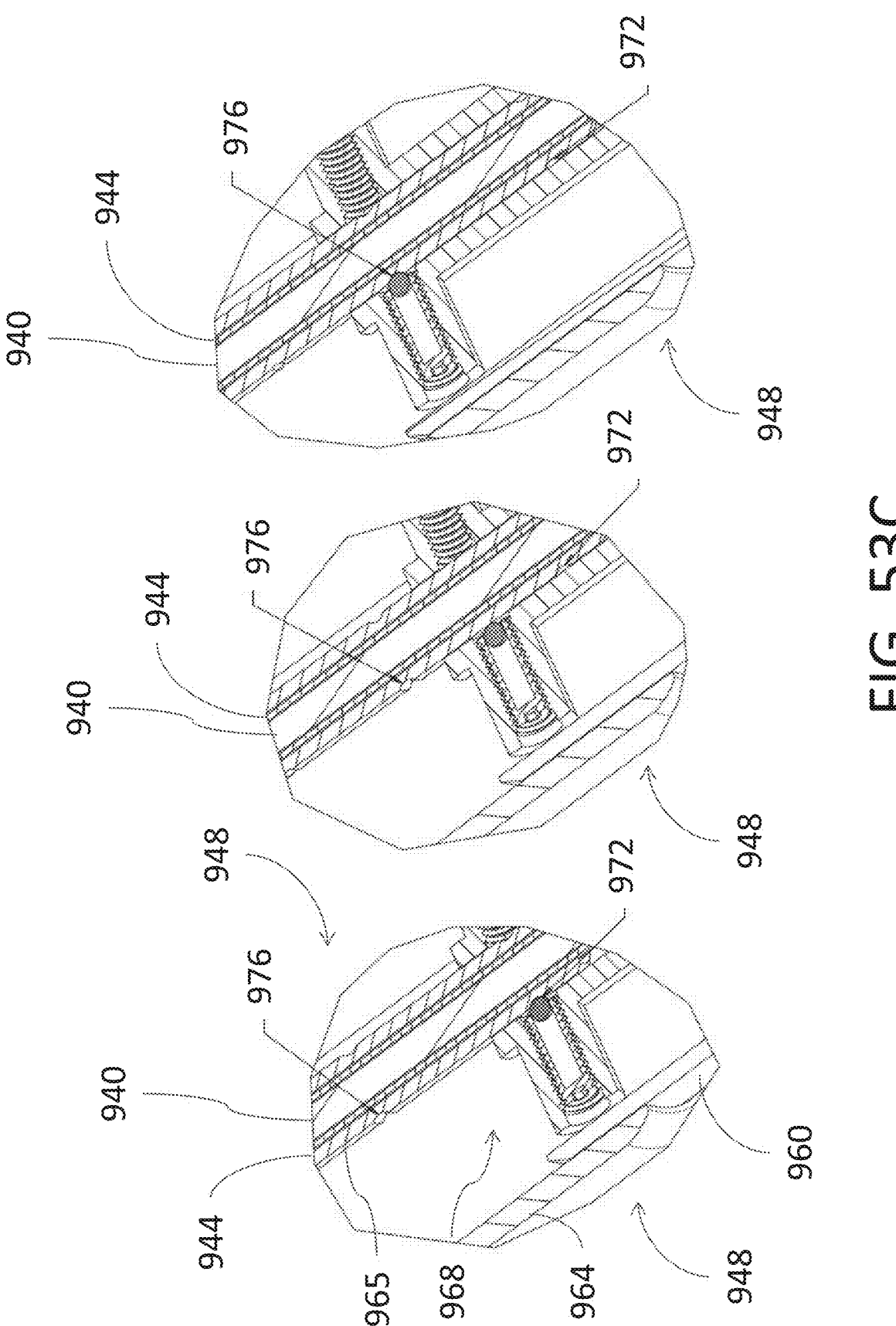
FIG. 53C shows the operation of the detent mechanism in three positions.
Figures 53D, 53E:
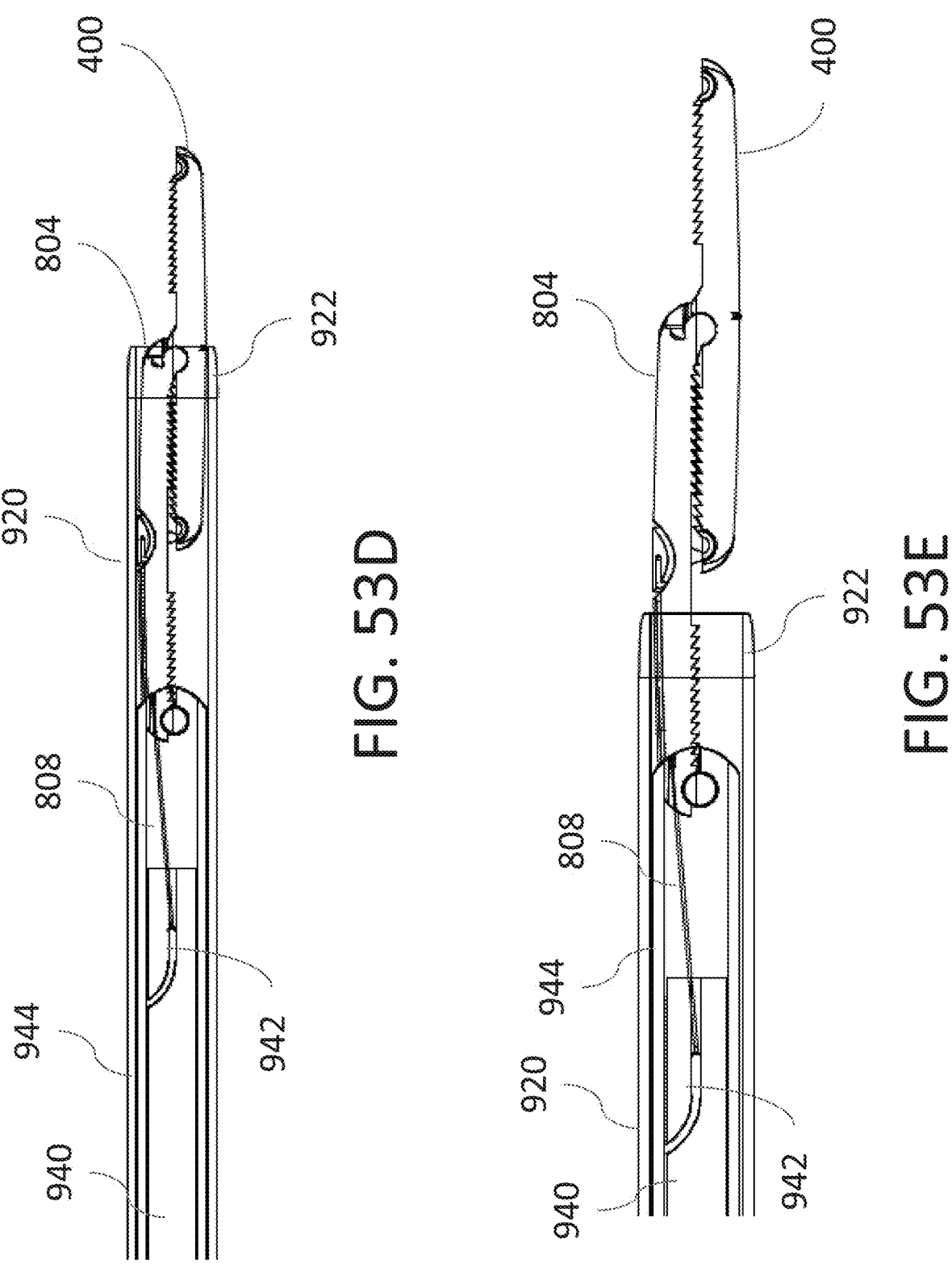
FIG. 53D shows the heart valve prosthesis initially emerging from a distal end of a distal portion of the delivery system in a first position relative to the prosthesis components.
FIG. 53E shows the heart valve prosthesis further advanced from the position of FIG. 53D with the distal end of the delivery system in a second position relative to the prosthesis components.

FIGS. 53A-53C show structures of one embodiment of the prosthesis member manipulator 948. As discussed above, the prosthesis member manipulator 948 is configured to provide controlled motion of the heart valve prosthesis 790 relative to (e.g., out of) the distal end 922. FIG. 53A is a cut-away of the distal end 922 showing the first member 400 and the second member 804 disposed therein. The first member 400 and the second member 804 are arranged such that their longitudinal axes are parallel to each other with the first and second members 400, 804 being longitudinally shifted relative to one another such that corresponding peripheral edges are off-set. A distal-most peripheral edge of the first member 400 can be disposed distally of a distal-most peripheral edge of the second member 804, e.g., by one-quarter by one-half or by three-quarters of the length of the first member 400. The second elongate member 944 can be coupled with a proximal most peripheral edge of the second member 804. The second elongate member 944 can be configured to releaseably couple to the second member 804 as discussed further below.

FIG. 53B shows an internal view of a portion of the one embodiment of the prosthesis member manipulator 948. In this view, the proximal grip 964 which is coupled to the second elongate member 944 is at a proximal position relative to the distal grip 960. This position corresponds to the first member 400 being retracted within the distal end 922 of the guide catheter 900 as shown in FIG. 53A. The first elongate member 940 is disposed through the second elongate member 944 as discussed above. The first elongate member 940 is coupled with the loop-shaped tension member 860, 860A.

FIG. 53C shows the detail indicated in FIG. 53B with the proximal grip 964 in three separate positions relative to the distal grip 960. The left most image corresponds to the position of FIG. 53B, e.g., a first, fully proximal position with the first member 400 retracted into the distal end 922 of the guide catheter 900. The center image shows the proximal grip 964 advanced to a second position distal of the first position. The motion can be controlled by a detent mechanism 968 disposed between the distal grip 960 and the second elongate member 944. For example, a spring-loaded ball can be disposed against the outside surface of an internal extension 965 of the proximal grip 964. The internal extension 965 can have one or a plurality of detents, e.g., a first detent 972 and a second detent 976 disposed on an outside surface of the internal extension 965. Motion from the first position (left image) to the second position (center image) can shift the position of the spring loaded ball from the first detent 972 to a compressed state for sliding the distal grip 960 and the proximal grip 964 toward each other. The shifted position can correspond to the distal-most peripheral edge of the first member 400 shifting distally out of the distal end 922 of the guide catheter 900 (See FIG. 53D). FIG. 53C right image shows a third position in which the proximal grip 964 is shifted distally relative to the position of the proximal grip 964 in the center image of FIG. 53C. Control of the distal shifting of the proximal grip 964 can be controlled by the detent mechanism 968, e.g., by motion of the spring loaded ball from the first detent 972 to the second detent 976. Motion of the internal extension 965 along the detent mechanism 968 between the positions of the first detent 972 and the second detent 976 is provided by a force for hand manipulation but when the second or third positions are arrived at the motion is noticeably stopped. A third position (not shown) corresponds to the first member 400 fully extended form the distal portion 920, e.g., with the proximal-most peripheral edge disposed distal of the distal end 922 of the distal portion 920.

Figure 53F:
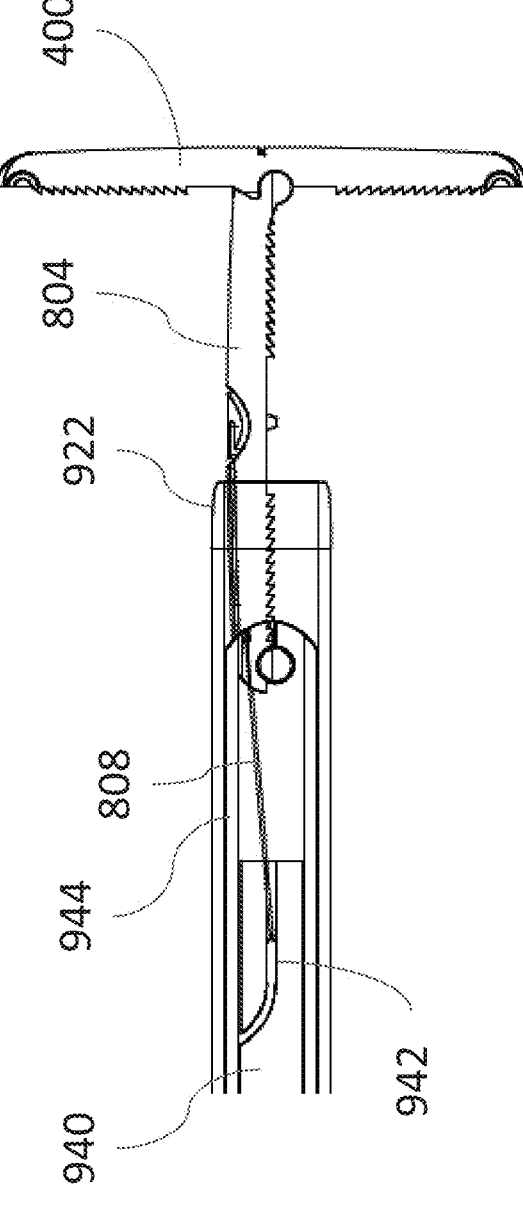
FIG. 53F shows the heart valve prosthesis in a modified configuration relative to that of FIG. 53E with the distal end of the delivery system in the second position.
Figure 53G:
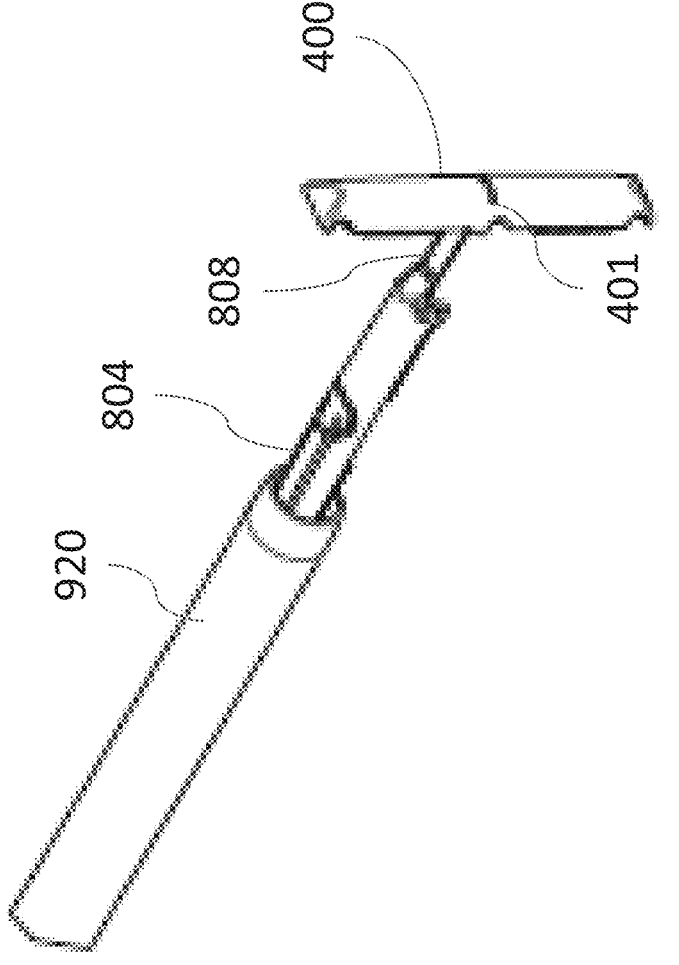
FIG. 53G shows the second member of the heart valve prosthesis emerging from the distal end of the delivery system in a third position at a stage following that of FIG. 53F.

In a manner similar to that discussed above in connection with the first member 400 in FIG. 24, the delivery system 792 allows the first member 400 to pivot to a transverse position, e.g., with the longitudinal axis of the first member 400 disposed perpendicular to the longitudinal axis of the second member 804 while the prosthesis member manipulator 948 is in the third position (right image of FIG. 53C). The transverse position of the first member 400 can be seen in FIGS. 53F and 53G. In FIG. 53F the distal-most peripheral edge of the second member 804 is distal the distal end 922 of the distal portion 920 and the proximal-most peripheral edge of the second member 804 is proximal of the distal end 922. FIG. 53G shows that while the prosthesis member manipulator 948 is in the third position, the first member 400 can be moved or can be allowed to move distally of the distal end 922. The first member 400 can be moved or can be allowed to move distally of the peripheral edge of the second member 804 that is distal-most in the delivery position. Such motion can be provided for or allowed by movement of the first elongate member 940 relative to the second elongate member 944 within the prosthesis member manipulator 948. Such motion would cause the distal end of the first elongate member 940 to be shifted closer to the distal end 922 relative to the position shown in FIG. 53F.

The position of FIG. 53G allows the first member 400 to be disposed on a first side of the valve V (e.g., in the right ventricle) while the second member 804 is disposed on a second side of the valve V (e.g., in the right atrium). The prosthesis member manipulator 948 can be manipulated to bring the first member 400 into contact with the leaflets in the right ventricle by applying a proximally directed force on the proximal grip 964.

Figure 53I:
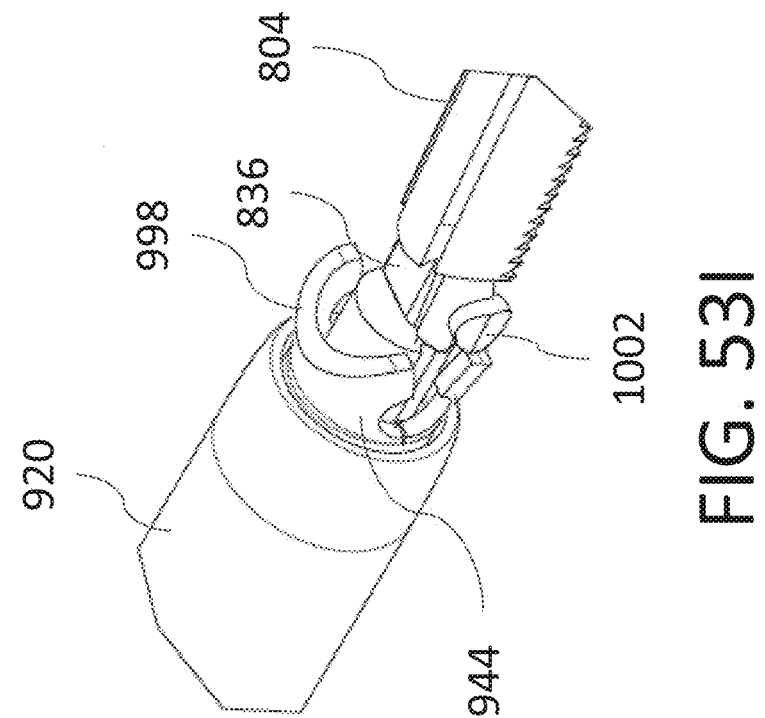
FIG. 53I shows the second member of the heart valve prosthesis being released from a control body of the delivery system.
Figure 53H:
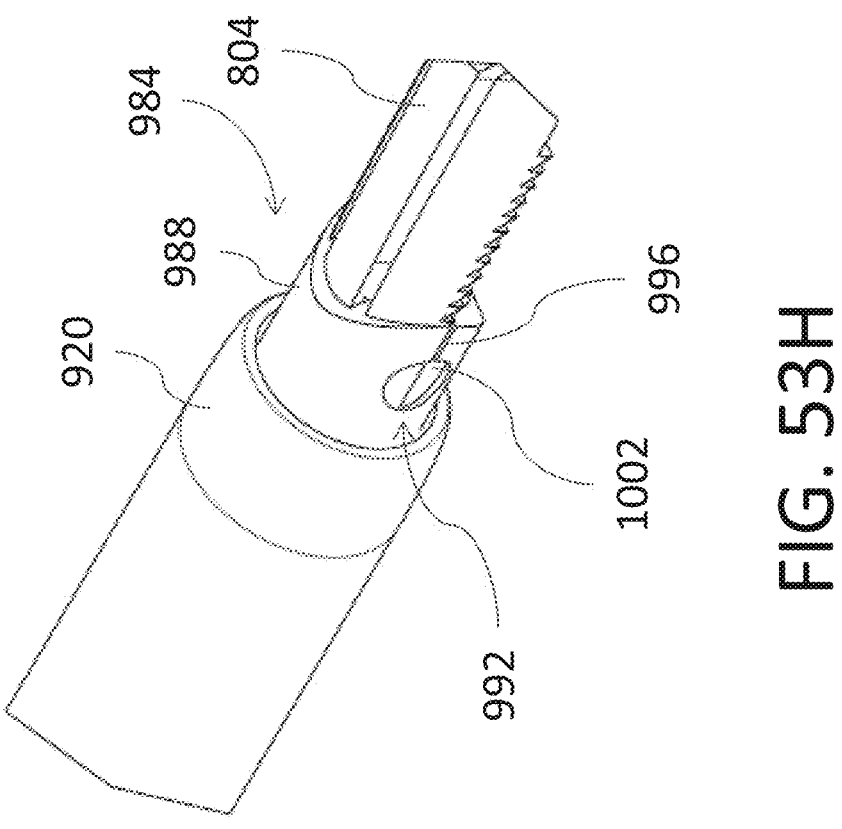
FIG. 53H shows the second member of the heart valve prosthesis fully extended from the distal portion of the delivery system in a fourth position at a stage following that of FIG. 53G.

FIG. 53H shows that the proximal-most end of the second member 804 can be advanced out of the distal end 922 of the distal portion 920. Though not shown in FIG. 53C, a fourth position of the detent mechanism 968 can be provided that includes a third detent where shifting from the third position (right image of FIG. 53C) to the fourth position (not shown) provides the relative position of the second member 804 to the distal end 922 shown in FIG. 53H. In this position the second elongate member 944 is disposed partially distally of the distal end 922. The second elongate member 944 can include a flexible retainer 984 that can hold a circular projection 1002 (or one or more other features) disposed at or near the peripheral edge of the second member 804 that is disposed proximally in the delivery system 792. The flexible retainer 984 can include a circular opening 992 disposed between opposing jaws 988. A slit 996 can separate a portion of the opposing jaws 988 distal of the circular opening 992 such that the distal portions of the opposing jaws 988 can separate from each other. FIG. 53I shows the distal portions of the opposing jaws 988 separated from each other. In one arrangement, the free state of the second elongate member 944 unconstrained by the inside of the distal portion 920 can be as shown in FIG. 53I. This results in the second elongate member 944 opening upon extension of the second elongate member 944 from the distal portion 920 such that the circular projection 1002 is not held or constrained in the circular opening 992. When extended from the distal end 922 and unconstrained, the second member 804 can pivot from the position of FIGS. 53H and 53I to a transverse position as in FIG. 53J.

In another embodiment, the proximal peripheral edge of the second member 804 can be pushed out of the flexible retainer 984 by the distal end of the first elongate member 940. The force of the distal end of the first elongate member 940 on the second member 804 can force the jaws 988 to open. The jaws 988 are configured by the guide catheter 900 when disposed therein and cannot open even if the distal end of the first elongate member 940 were to push on the second member 804 because the jaws are contained by the inner surface of the guide catheter 900.

The second member 804 can be configured for low-profile placement in the guide catheter 900. For example, the low profile portion 836 can be recessed relative to the surface 824 that is opposite to the tissue engaging surface 820 by an amount equal a partial or total thickness of the wall 998. The thicknesses of wall 998 can thus be received partially within the thickness of the second member 804. This allows a larger second member 804 to be received in the guide catheter 900 or can allow the guide catheter 900 to have a lesser thickness than if the entire thickness of the second member 804 between the tissue engaging surface 820 and the surface opposite 824 were disposed within the innermost surface of the second elongate member 944.

An advantage of the configuration of the second elongate member 944 is providing great security in the holding the second member 804 until release of the second member is desired. In the illustrated embodiment the flexible retainer 984 holds the second member 804 in a delivery position or configuration (as shown in FIGS. 53A and 53D-53G) until release is appropriate. When an appropriate release stage is released the flexible retainer 984 can be extended out of the distal end 922 of the delivery catheter at which time the second member 804 can be released. Prior to this point the second member 804 is prevented from being released from the second elongate member 944 of the delivery system 792. This is one of the aspects in which the prosthesis 790 and the delivery system 792 are configured to provide for controlled catheter based assembly of components that are separated from each other within the body, e.g., with a chamber of the heart, and thereafter re-assembled in a treatment configuration in the heart.

Figure 53J:
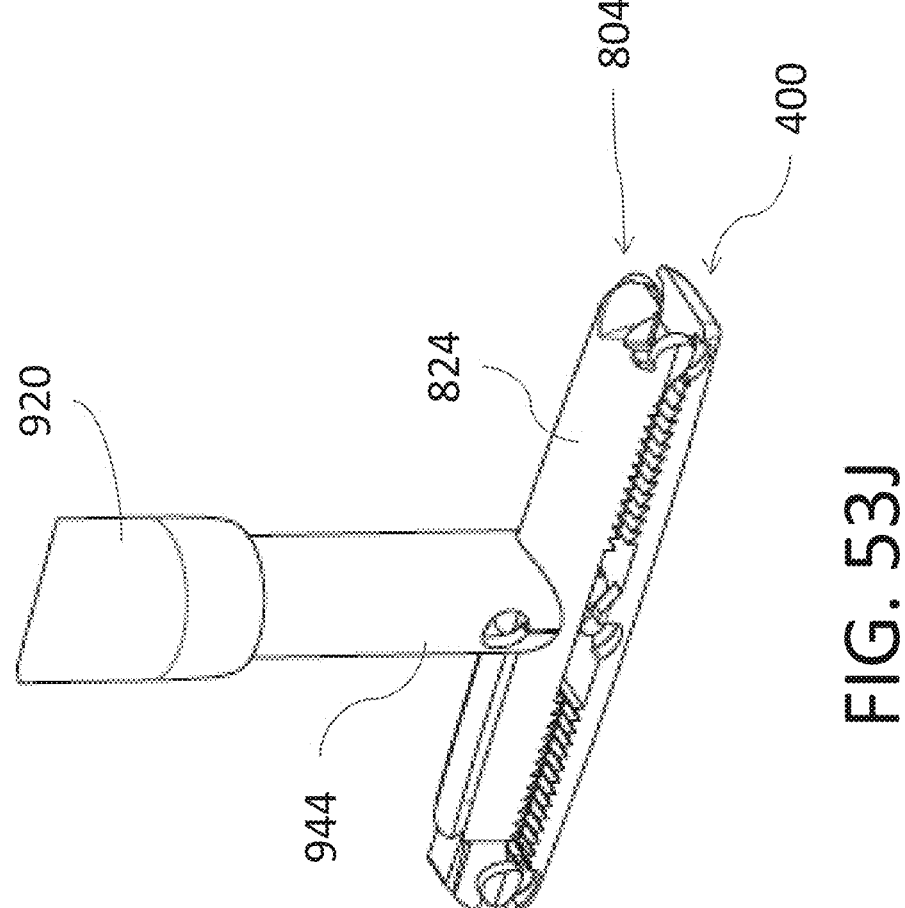
FIG. 53J shows the heart valve prosthesis in configuration where the first member and the second member are engaged such that a heart valve leaflet can be secured therebetween.

FIG. 53J shows that the second elongate member 944 can be advanced into contact with the surface 824 that is opposite the tissue engaging surface 820. The distal face of the second elongate member 944 can be curved to match the curvature of the surface opposite 824 as seen in a cross-section taken perpendicular to the longitudinal axis of the second member 804 or in an end view of the second member 804 (see, e.g., FIG. 18 which is similar in this regard).

Figure 53K:
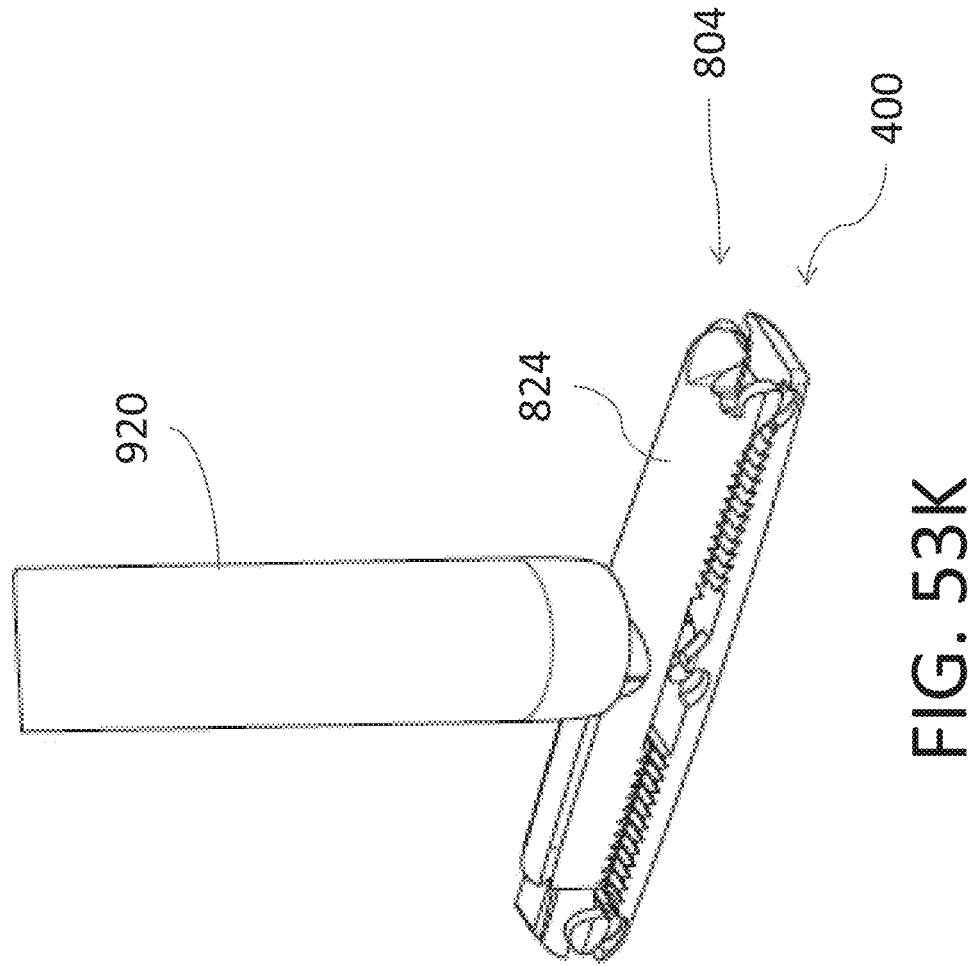
FIG. 53K is a perspective view showing the distal portion of the guide catheter advanced over a distal portion of a first control body of the delivery system.

FIG. 53K shows that in another embodiment, the distal portion 920 of the guide catheter 900 can be advanced into engagement with the surface 824 that is opposite the tissue engaging surface 820. When so engaged, the distal portion 920 can be used to manipulate the second member 804 to rotationally position the second member 804. The distal portion 920 also can be used to advance the second member 804 into the leaflet grasping position relative to the first member 400, as shown in FIG. 53K. This arrangement also allows the members 400, 804 to be compressed together during wire twisting. With the prosthesis member manipulator 948 held stationary and the proximal grip 964 pulled proximally, the member 400, 804 are brought closer together for a tighter fit. Twisting the wire connector 808 holds them in place.

Figures 53L, 53M:
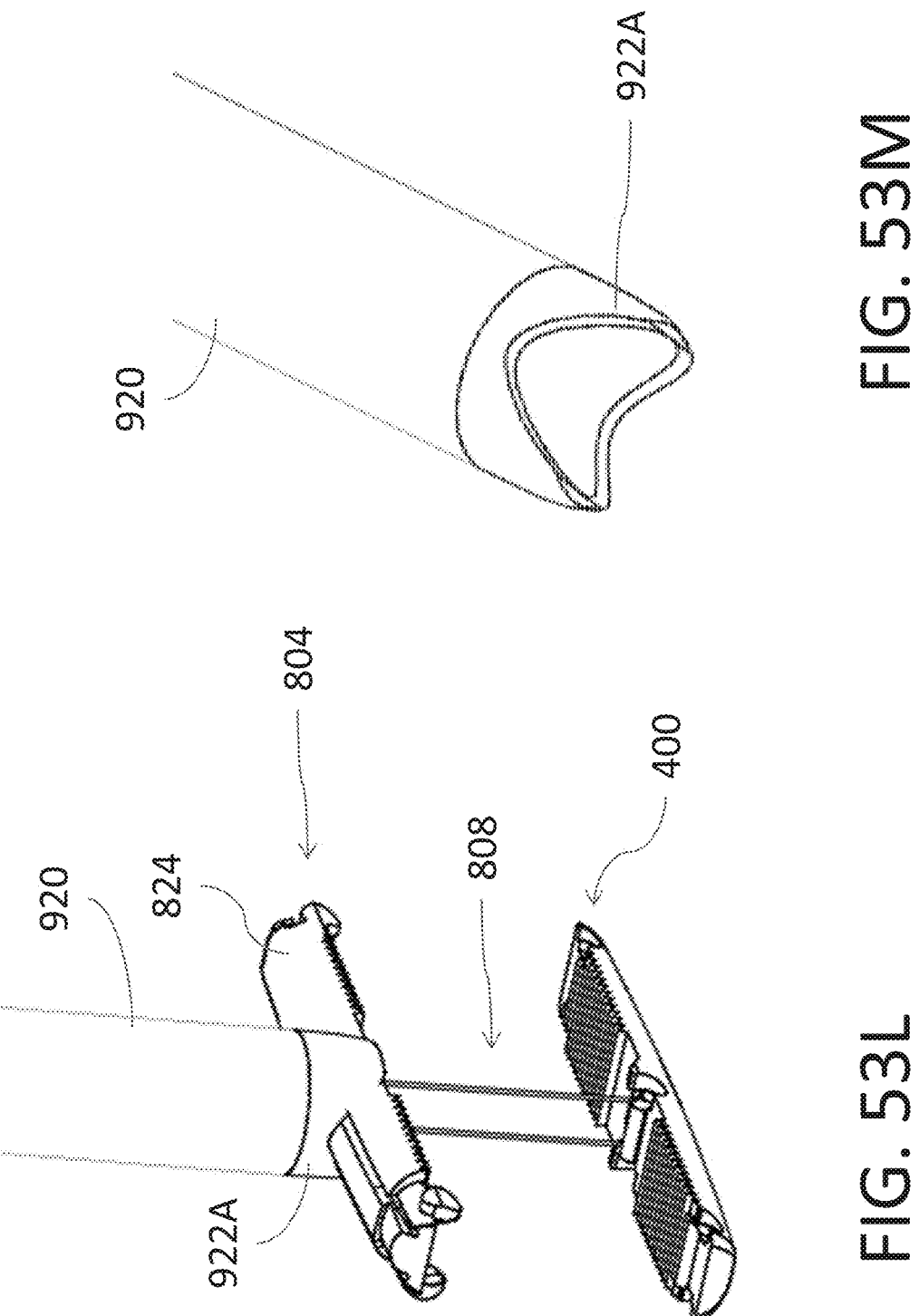
FIG. 53L shows an another embodiment of a guide catheter having a distal end configured for improved torque control.
FIG. 53M is a perspective view of a guide catheter adapted to rotationally control a second member of the heart valve prosthesis.

FIGS. 53L and 53M show that an alternative embodiment of the guide catheter 900 provides a distal end 922A having a contoured face. The face of the distal end 922 is generally flat, e.g., comprises a circle or other curve disposed in a plane transverse to the guide catheter 900. FIG. 53M shows that the distal end distal end 922A is curved and would not reside in a single plane but could have two portions (edges at 12 and 6 o'clock) in a plane and portions away from these edges spaced away from the plane (e.g., by progressively greater amounts away from the 12 o'clock position and the 6 o'clock position toward the 3 o'clock and the 9 o'clock positions respectively). The curvature of the distal face of the distal end 922 can be configured to mate with the surface

824 that is opposite the tissue engaging surface 820 as shown in FIG. 53L. The distal end 922A is saddle-shaped in some embodiments.

The contoured surfaces of the distal end 922A and the second elongate member 944 provide enhanced control of the rotational position of the second member 804. However, if the distal end 922 is relatively soft the guide catheter 900 can provide good control of the second member 804 as well.

Figure 54:
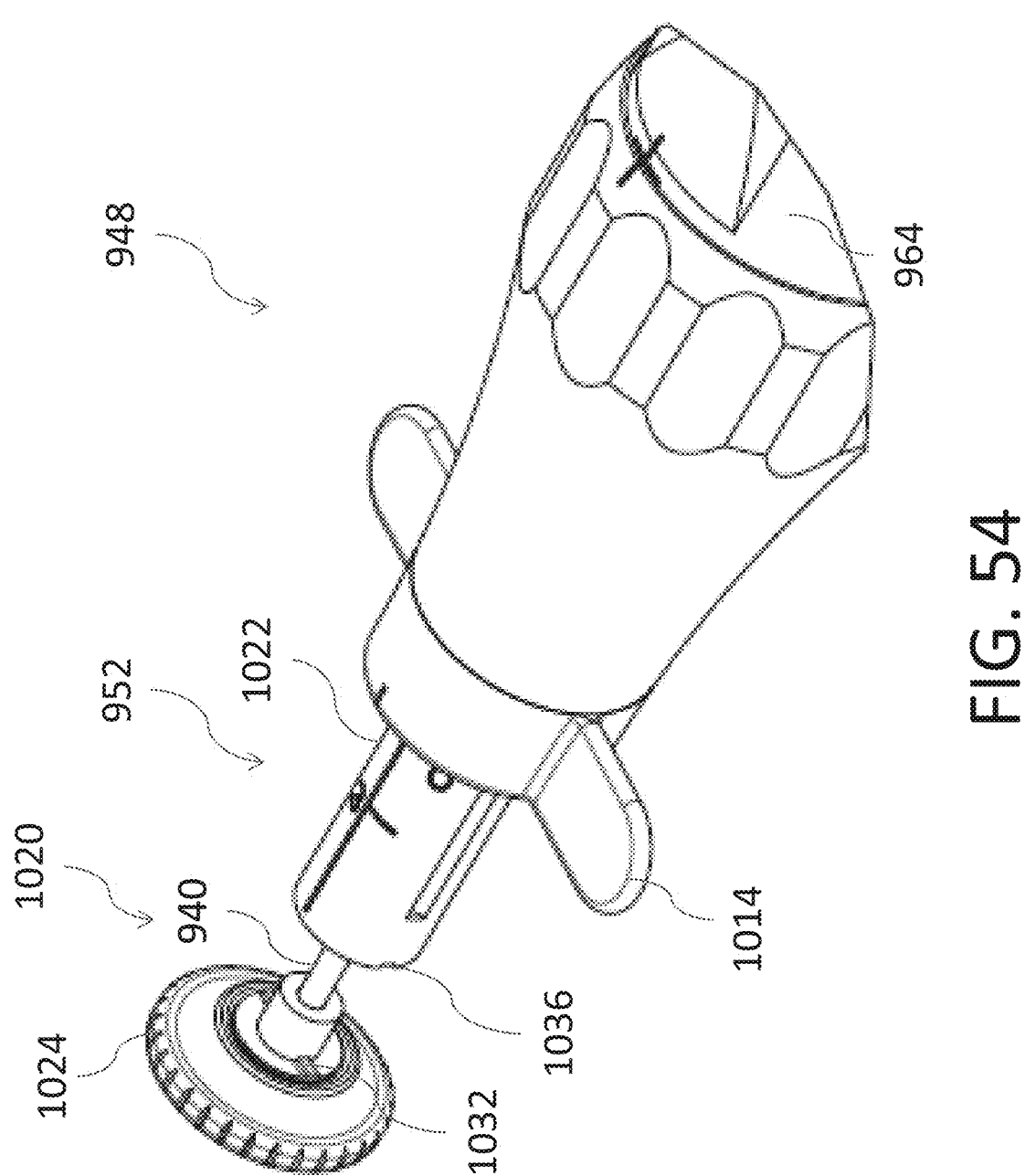
FIG. 54 is a perspective view of a proximal portion of the delivery system of FIG. 51, showing a prosthesis member manipulator.
Figure 56:
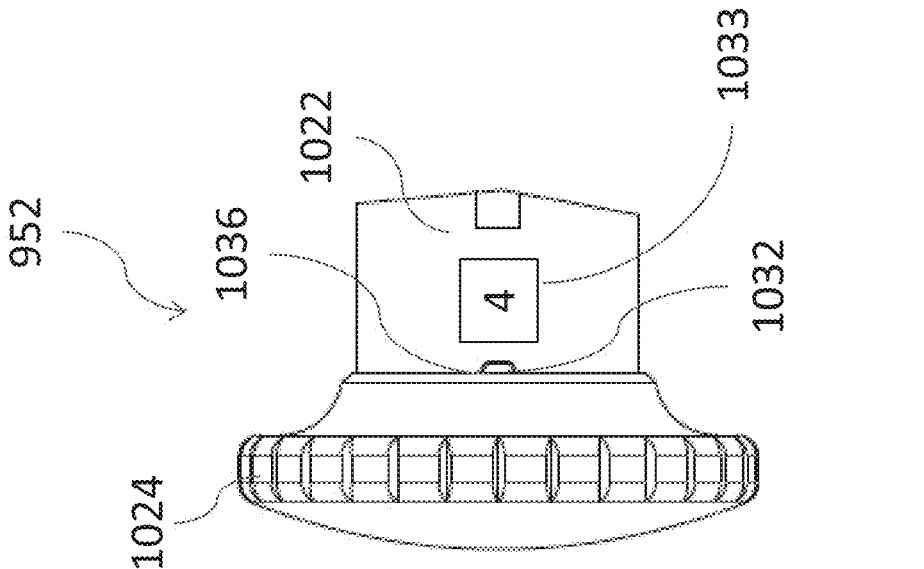
FIG. 56 shows a cap configured to be rotated to secure portions of the heart valve prosthesis together while providing tactile feedback to the physician.
Figure 55:
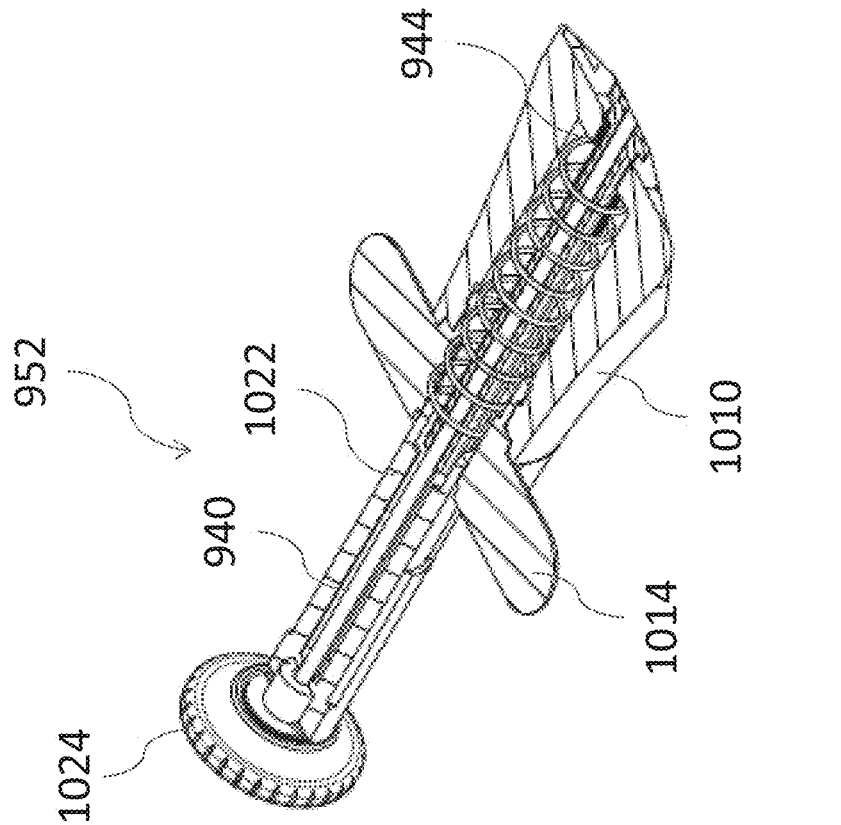
FIG. 55 is a cross-sectional view of a proximal portion of the prosthesis member manipulator.

FIGS. 54-56 show further aspects of the connector manipulator 952 of the prosthesis member manipulator 948. The first elongate member 940 extends out of the proximal grip 964 through a bearing 1022 of the wire twister 1020. The first elongate member 940 is coupled to the cap 1024 such that rotation of the cap 1024 causes 1:1 rotation of the first elongate member 940. The wire twister 1020 also has a tactile feedback feature such that the user can know how much twisting has been provided during application of the connector 808. The tactile feedback feature can include a distal protrusion 1032 facing distally on the cap 1024 and a proximal recess 1036 facing proximally on the bearing 1022. Rotation of the cap 1024 moves the distal protrusion 1032 from a position in which the distal protrusion 1032 is received in the proximal recess 1036 (see FIG. 56) to a position where the distal protrusion 1032 is not in the proximal recess 1036 but instead slides along the periphery adjacent to the proximal recess 1036 (e.g., 90 degrees from the position of FIG. 56). The bearing 1022 can have two proximal recesses 1036 spaced 180 degrees apart so that when the cap 1024 rotates the distal protrusion 1032 into engagement with the proximal recess 1036 opposite an initial proximal recess 1036 the user knows that a one-half rotation has occurred, causing the adjacent strands 862 to have a one-half twist. Another one-half twist will be noted by the user through the tactile feedback of the distal protrusion 1032 and the proximal recess 1036 such that full twist can be noted. Further rotations in the same direction can be counted to keep track of how many twists of the adjacent strands 862 are provided. This can allow the user to know if the proper tension is provided in the connector 808 and/or if the heart valve prosthesis 790 is operating as expected. As discussed above, the loop-shaped tension member 860 can be configured to fracture. The fracture can occur after one, two, three, four, five, six, eight or 10 full revolutions of the cap 1024. In some embodiments, the fracturing of the wire can occur on or after twenty, twenty-five, thirty, thirty-five, forty, forty-five, fifty, sixty, seventy, eighty, or even a hundred revolutions.

In various embodiments a need for the user to keep track of the number of half or full rotations can be reduced or eliminated. For example, a counter 1033 can be provided on the connector manipulator 952 to keep track of half or full rotations. The counter can include a visible window located on an external side of the bearing 1022. In FIG. 56 the counter 1033 includes a number display in which the number '4' indicates that 4 half turns or 4 full turns of the cap 1024 have been provided. As additional half turns or full turns occur the number display increments from '4' to '5' and so on. This position is advantageous if the user will grasp a knob 1010 or lateral projections 1014 of the prosthesis member manipulator 948 with one hand and will twist the cap 1024 with the other hand while viewing the side surface of the bearing 1022 between the hands. The counter 1033 could be located on the proximal surface of the cap 1024 or in another convenient position. In another embodiment the counter 1033 is optional but a limiter is provided on the number of half or full rotations of the cap 1024 such that the cap 1024 will cease rotating upon exceeding a pre-defined number of rotations upon which the connector 808 will fracture. In this embodiment the user need not count the number or half or full rotations, though of course they can, but will know upon reaching the stop position that the connector 808 has fractured based on the design.

The tactile feedback of the wire twister 1020 can be provided by a rotational detent mechanism, e.g., one that urges the bearing 1022 toward the cap 1024 by spring-loading as shown in FIG. 55.

Figure 58:
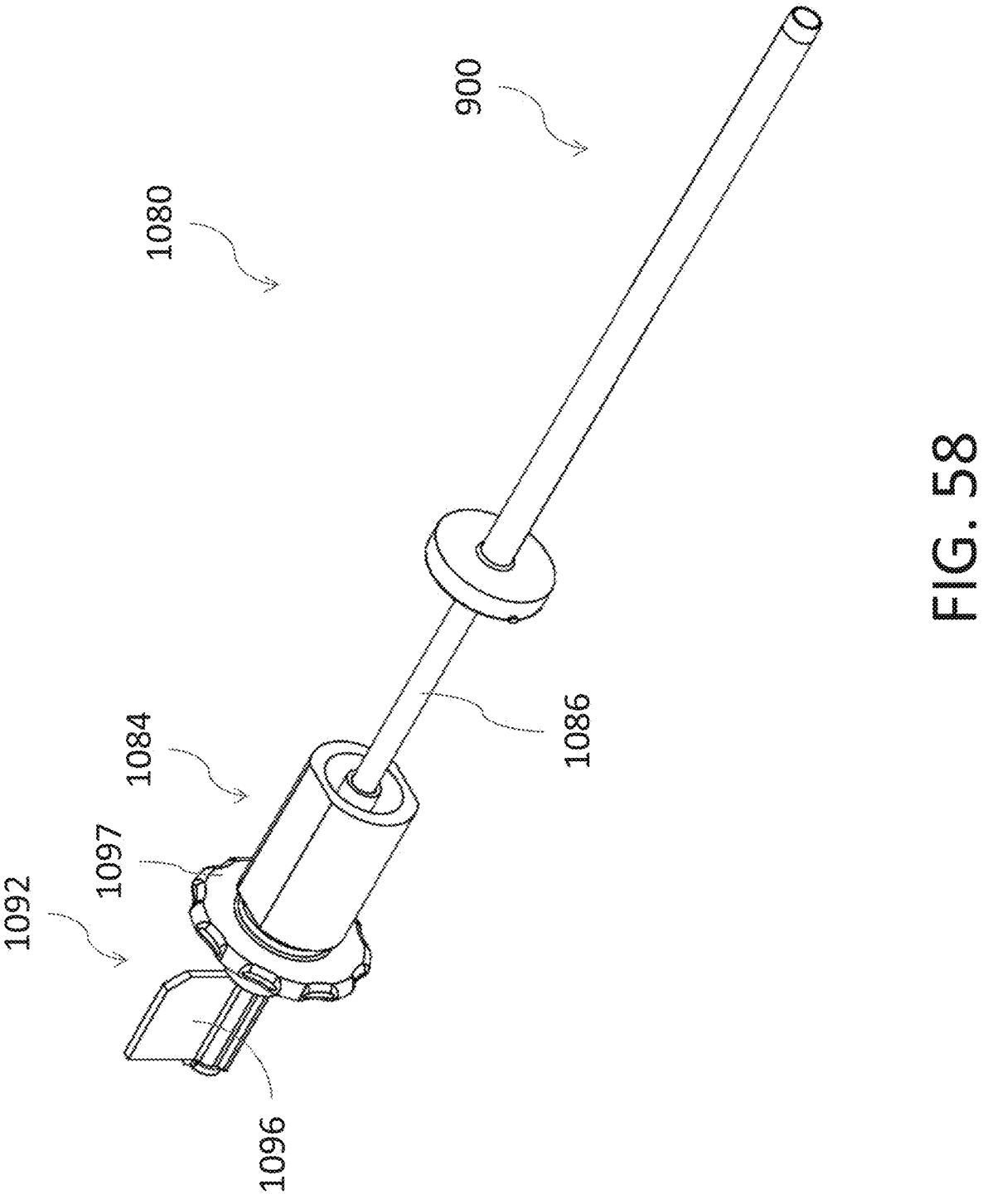
FIG. 58 is a perspective view of another embodiment of a delivery system.
Figure 59:
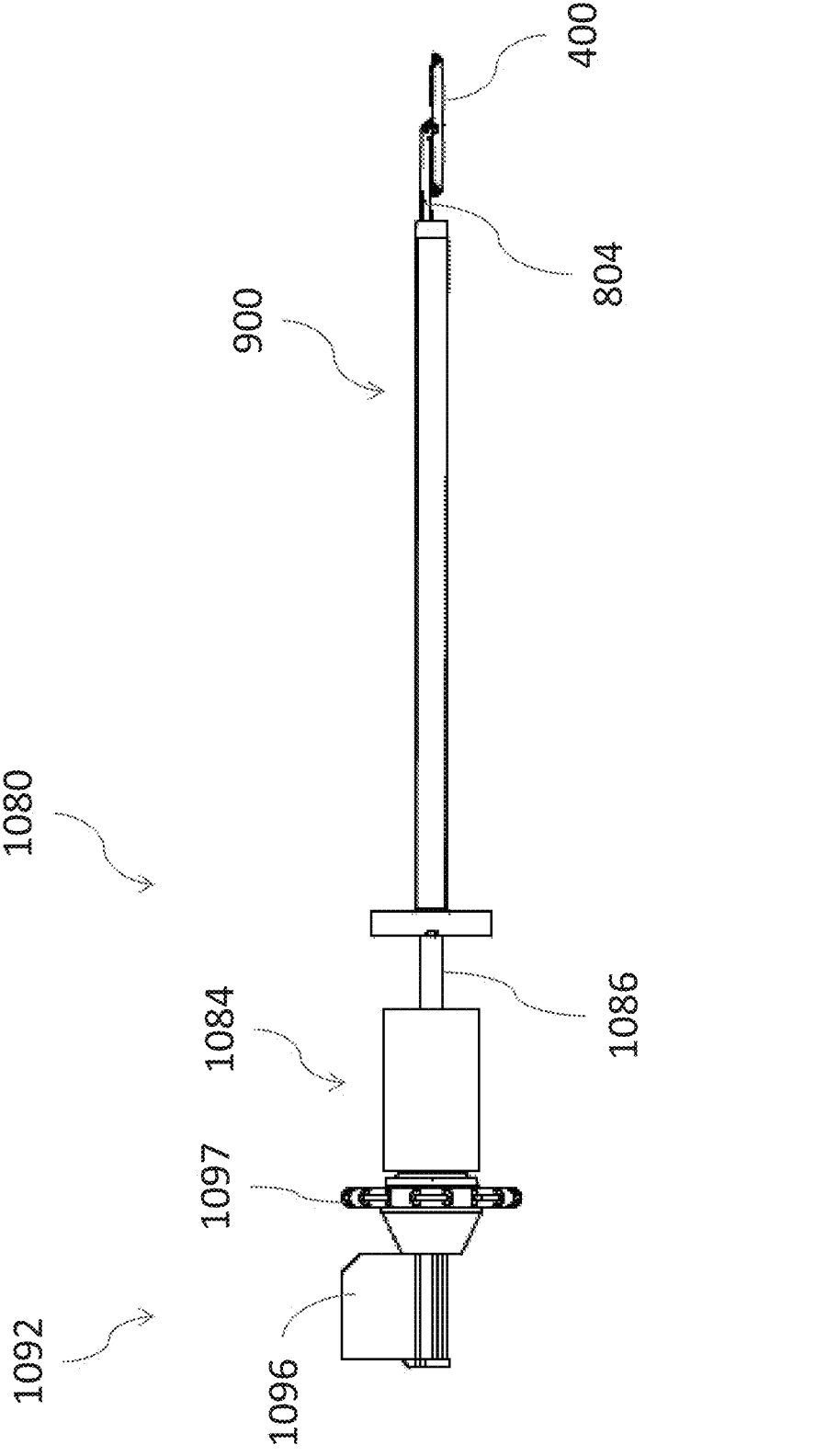
FIG. 59 is a side view of the delivery system of FIG. 58 with a prosthesis component shown fully advanced out of a delivery catheter thereof.
Figure 60:
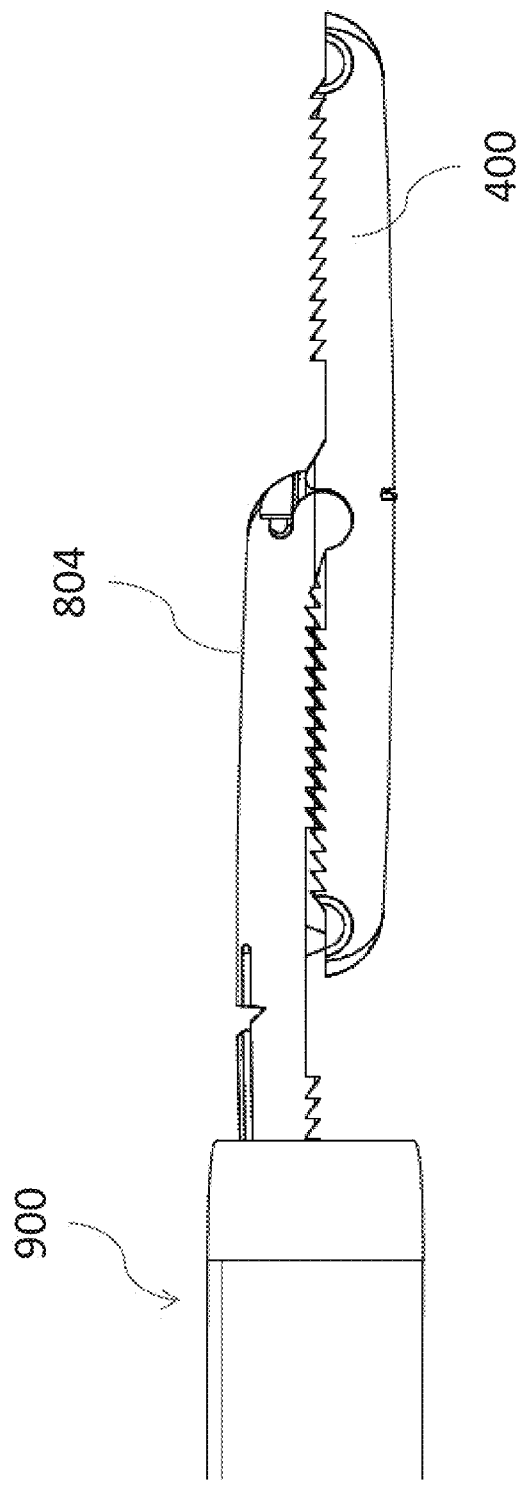
FIG. 60 is an enlarged distal end view showing a distal prosthesis component fully extended out of the delivery catheter.

The delivery system 792 provides both control and immediate response to user input. Features of the delivery system 104 could be incorporated into the delivery system 792. For example, the actuators 304, 328, 332 and the corresponding locking features can be provided in place of or in addition to the detent mechanism 968 for better positive locking in set positions. Or, one or more of the first detent 972, second detent 976, third detent 978 could be incorporated into the delivery system 104 to provide a combination of detent and positive locking with actuators for a device that combines some of the features of the system 104 and the delivery system 792. FIGS. 58-60 depict another delivery system that includes less position control than the delivery system 792 but provides greater immediacy of response to user input. Each of the delivery systems 104, 792, and 1080 can be used for different users. For example, the least experienced user may prefer the system 104 which gives more positive position control. The most advanced user may prefer the immediacy of the delivery system 1080 discussed below. The delivery system 792 provides a compromise for the typical user preferring relatively immediate response to inputs but some feedback about position using the detent mechanism 968 and a tactile feedback interface 1028 including the distal protrusion 1032 and the proximal recess 1036 of the wire twister 1020.

Figure 57:
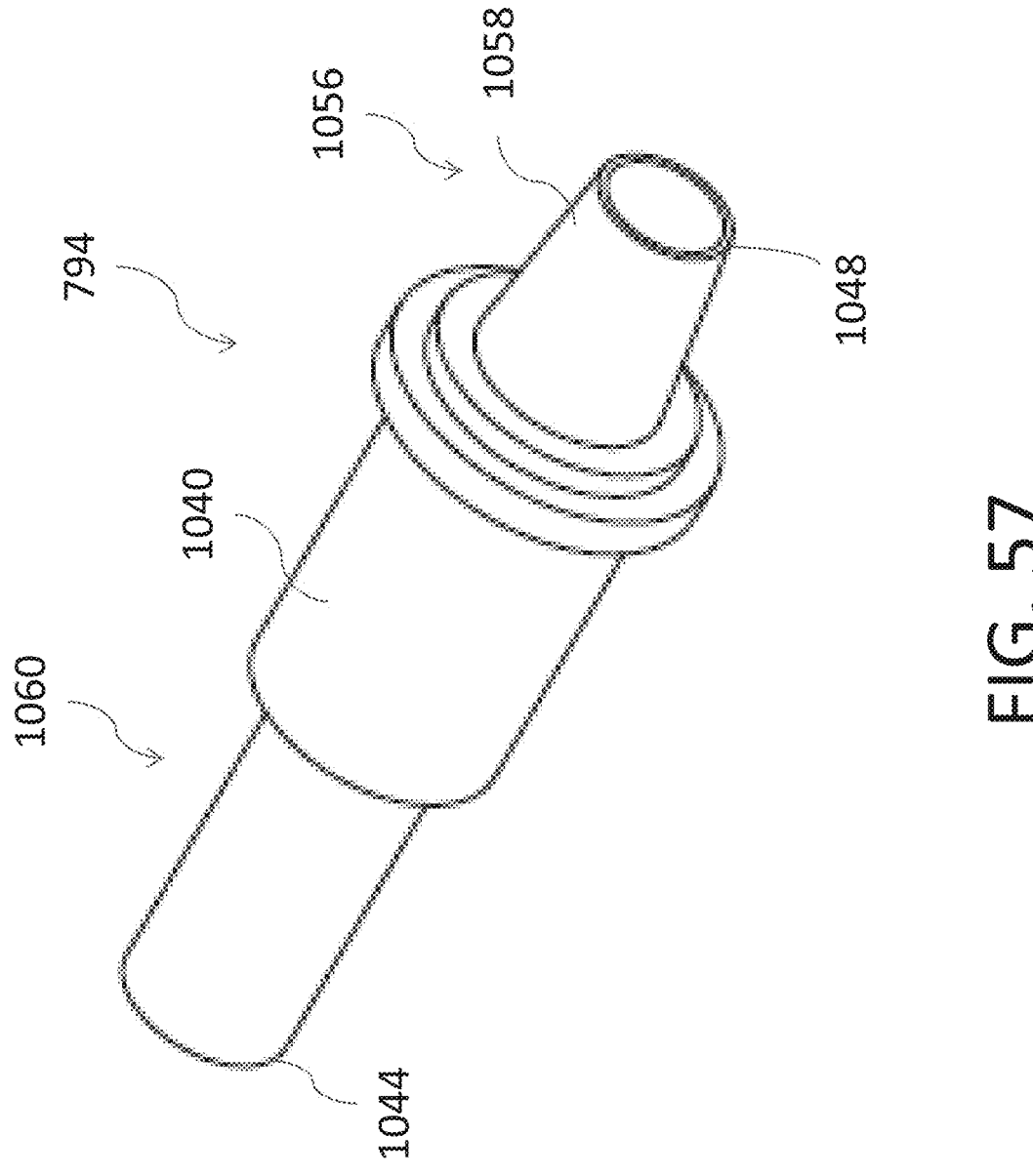
FIG. 57 is a perspective view of a loading capsule that can be used to place components of a heart valve prosthesis into a delivery system.
Figure 57A:
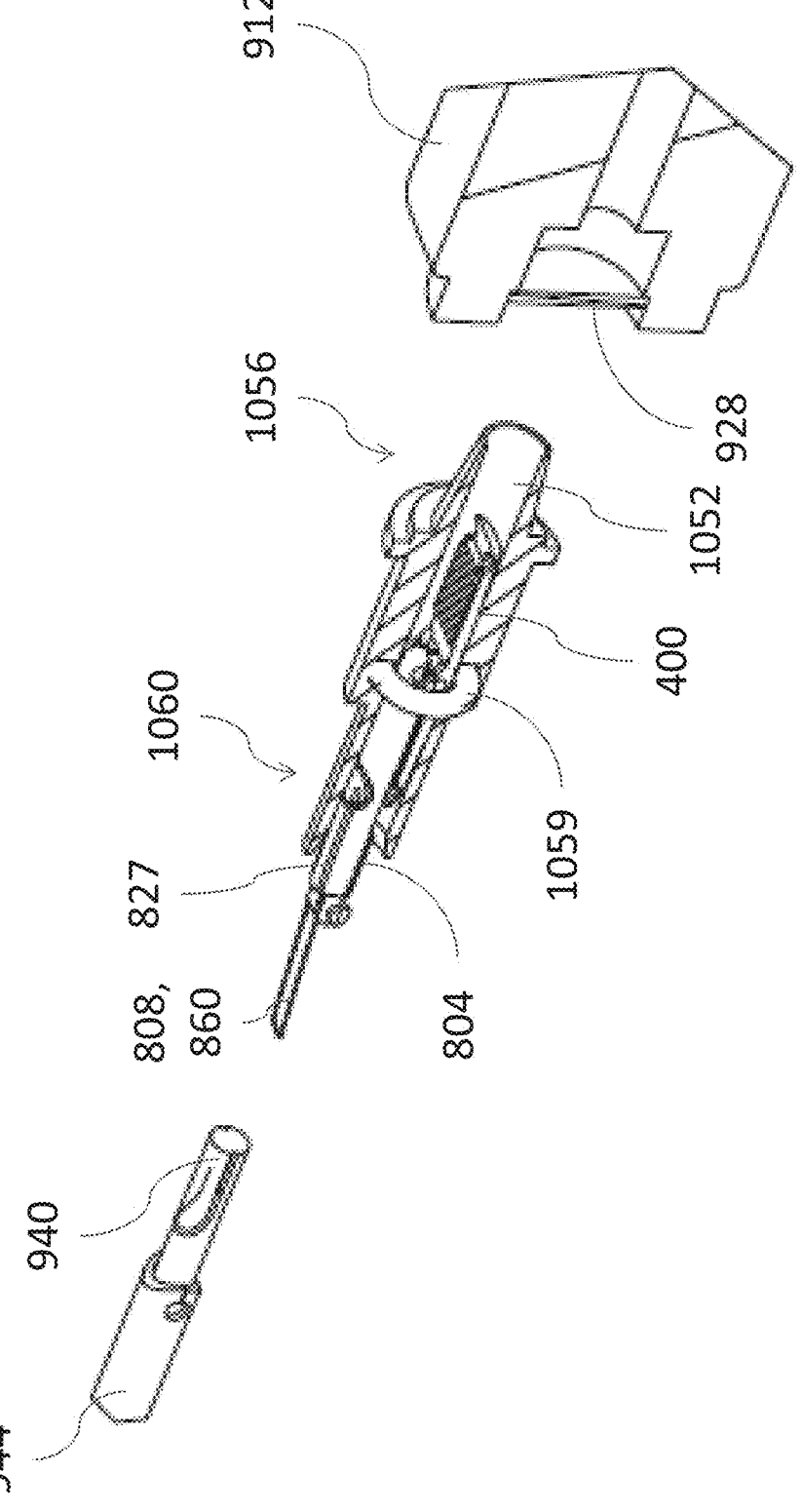
FIG. 57A is an exploded view of the delivery system illustrating an early portion of a method of loading the heart valve prosthesis into the delivery system.

FIG. 57 & FIG. 57A-F show the loading capsule 794 and its use in assembling the components of the heart valve prosthesis 790 to the components of the delivery system 792. FIG. 57 shows that the loading capsule 794 includes a capsule body 1040 that extends between a proximal end 1044 and a distal end 1048. A lumen 1052 extends between the proximal end 1044 and the distal end 1048. See FIG. 57A. The lumen 1052 is sized to slideably receive the first member 400, the second member 804, and the second elongate member 944. The loading capsule 794 also includes distal zone 1056 and a prosthesis loading zone 1060. The distal zone 1056 is configured to be inserted into the guide catheter 900 and to mate therewith in a sealed manner. The distal zone 1056 includes a tapered surface 1058 that can mate with an internal recess of the hub 912 of the guide catheter 900 as discussed further below. Mating tapers can provide a robust interference fit in use.

FIG. 57A shows that a seal 1059 can be provided in the lumen 1052 to reduce or eliminate blood flow in a proximal direction in the lumen 1052. The seal 1059 can include an O-ring that is sized to closely fit around any one or all of the first member 400, the second member 804, and the second elongate member 944.

FIG. 57A shows an early phase of the assembling of the heart valve prosthesis 790 to delivery system 792 using the loading capsule 794. Prior to the phase shown in FIG. 57A, the connector 808 can be looped through the first member 400. For example the loop-shaped tension member 860 can be passed through openings in the first member 400 and along a channel in the surface of the first member 400 opposite the tissue engaging surface thereof. The loop-shaped tension member 860 can be passed through openings in the second member 804 as shown in FIG. 46. The second end portion 868 can be enclosed as shown in FIG. 46. In one technique the second end portion 868 can be enclosed by welding or other techniques as discussed in connection with FIGS. 47 and 48.

With the components of the heart valve prosthesis 790 assembled, the first member 400 can be inserted into the proximal end 1044 of the delivery system 792 until the first member 400 is less than one-half inserted into the lumen 1052. In this position the concave surface 432 and the first hinge portion 420 are exposed. The second member 804 can then be brought into contact with the first member 400 by placing convex projections 825 onto the concave surface 432 to mate with the first hinge portion 420. When connected in this manner, the second member 804 can be advanced into the lumen 1052 which causes the first member 400 to be further and fully advanced into the lumen 1052. The loop-shaped tension member 860 can be threaded through grooves 827 formed in the surface 824 that is opposite the tissue engaging surface 820. The second end portion 868 can be disposed proximally of the proximal end 1044. In various embodiments at least some of the foregoing positioning can be pre-assembled.

Figure 57B:
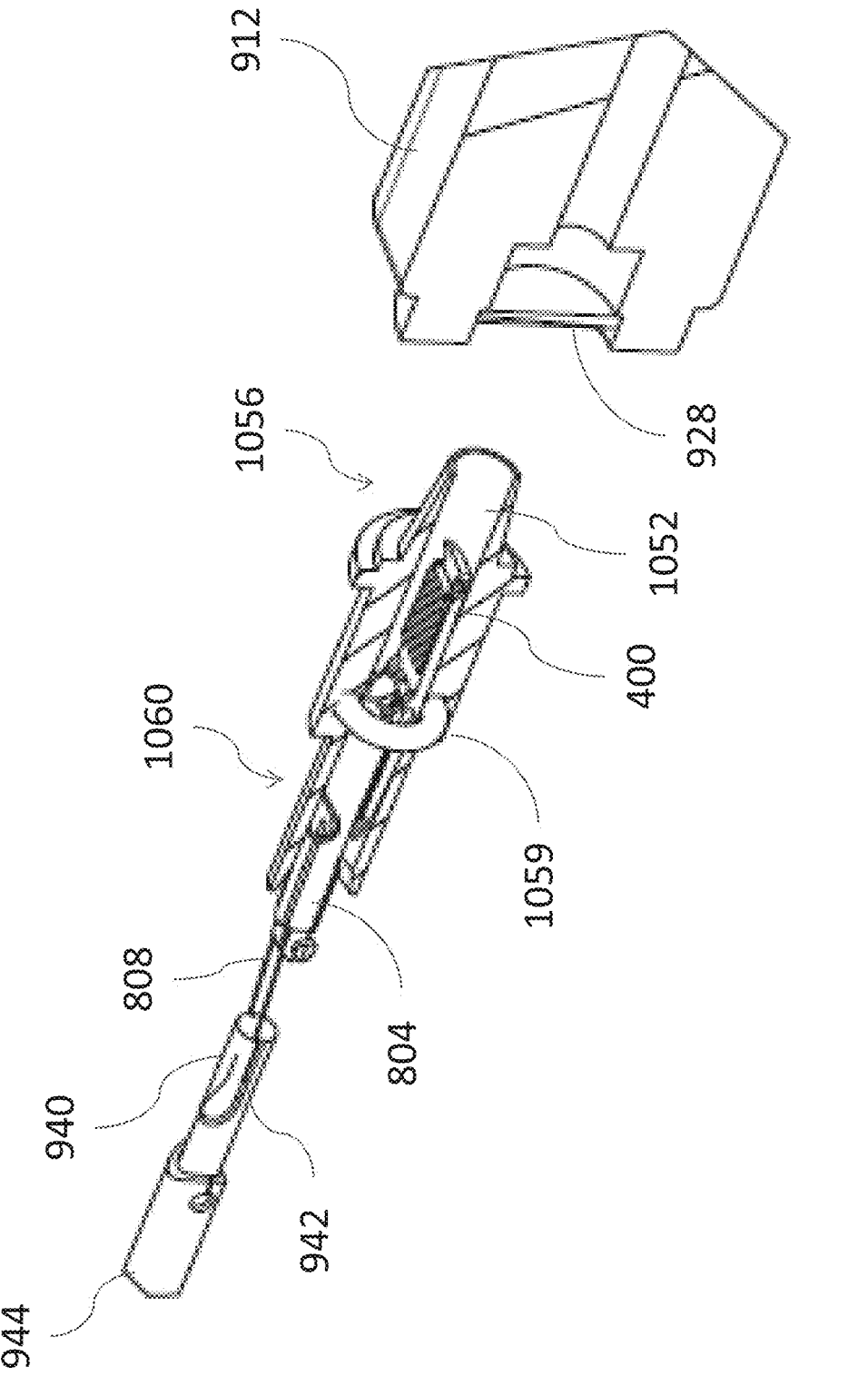
FIG. 57B is a view similar to that of FIG. 57A showing a loop shaped tension member of the heart valve prosthesis coupled with a distal portion of a control member while at least one of the first and second members of the heart valve prosthesis is partially inside the loading capsule.

FIG. 57B shows that the first and second elongate members 940, 944 can be brought adjacent to the proximal end 1044 such that the second end portion 868 can be threaded through a twisting groove 942 in the first elongate member 940. The twisting groove 942 can take any suitable form, but preferably includes an opening on a side surface of the first elongate member 940. The opening can lead to a proximally oriented surface against which the second enclosed end 872 can be seated. When seated in this manner, proximal force on the first elongate member 940 can pull the loop-shaped tension member 860 proximally. Proximal motion of the loop-shaped tension member 860 can be used in a method to move the first member 400 into engagement with leaflets of the valve V.

Figure 57C:
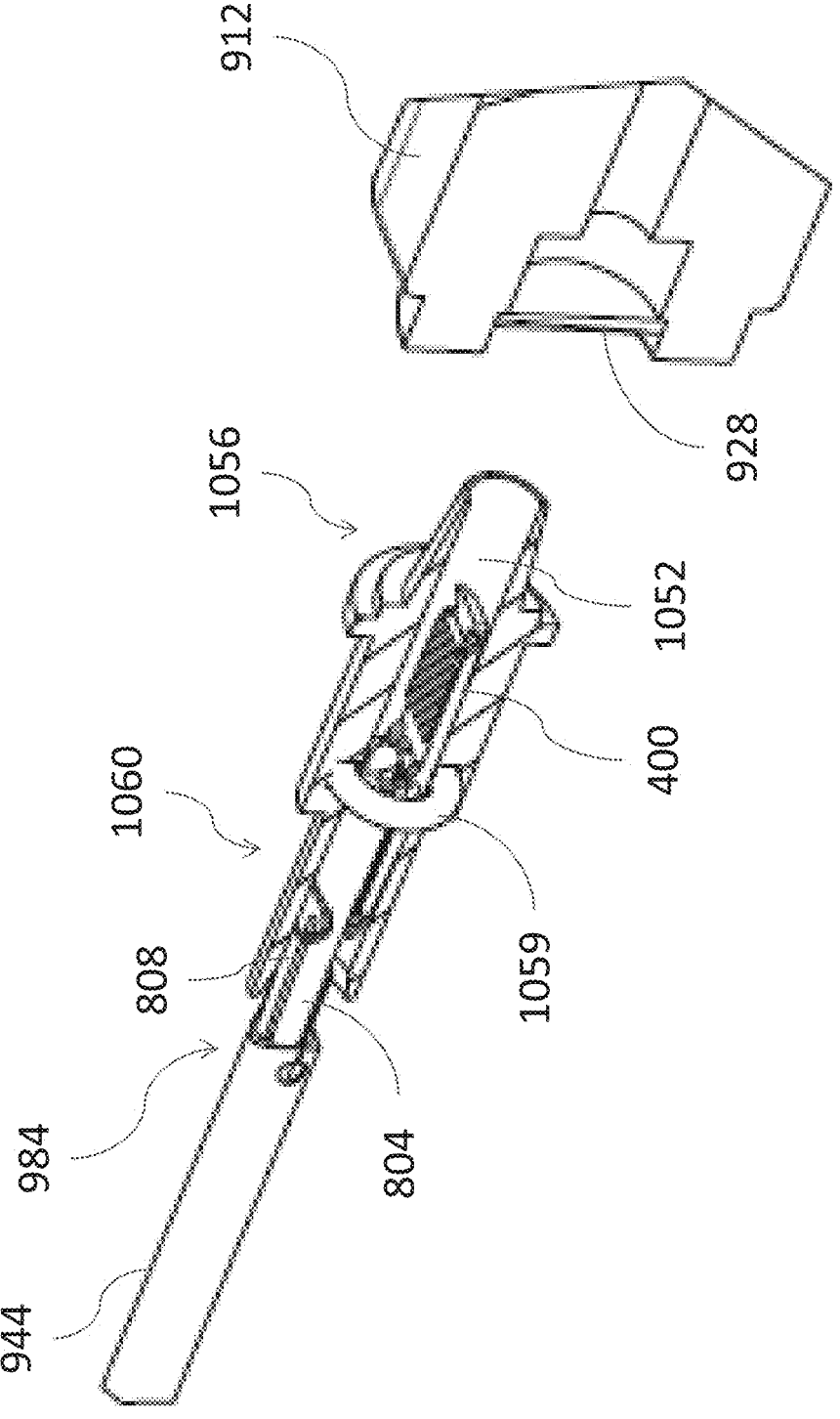
FIG. 57C is a view similar to that of FIG. 57A showing a distal portion of a control body coupled with a peripheral portion of a prosthesis component of the heart valve prosthesis, while the heart valve prosthesis is partially located inside the loading capsule.

FIG. 57C shows that after the second end portion 868 is engaged with the twisting groove 942 the second elongate member 944 can be advanced over the first elongate member 940 up to the second member 804. The flexible retainer 984 can be advanced over the circular projection 1002. If the flexible retainer 984 includes opposing jaws 988 that are biased to a spaced apart or open configuration the opposing jaws 988 can be compressed such that the second elongate member 944 can advance the second member 804 into the lumen 1052. The outer surface of the flexible retainer 984 is sized such that the flexible retainer 984 and the second elongate member 944 can be slideably inserted into the lumen 1052 and can pass through the seal 1059.

Figure 57D:
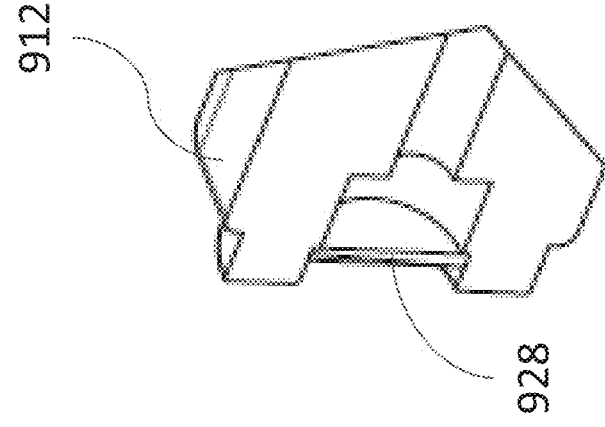
FIG. 57D is a view similar to that of FIG. 57C showing a distal portion of a control member coupled with a peripheral edge of a prosthesis component, the distal portion being advanced into the loading capsule.
Figure 57D:
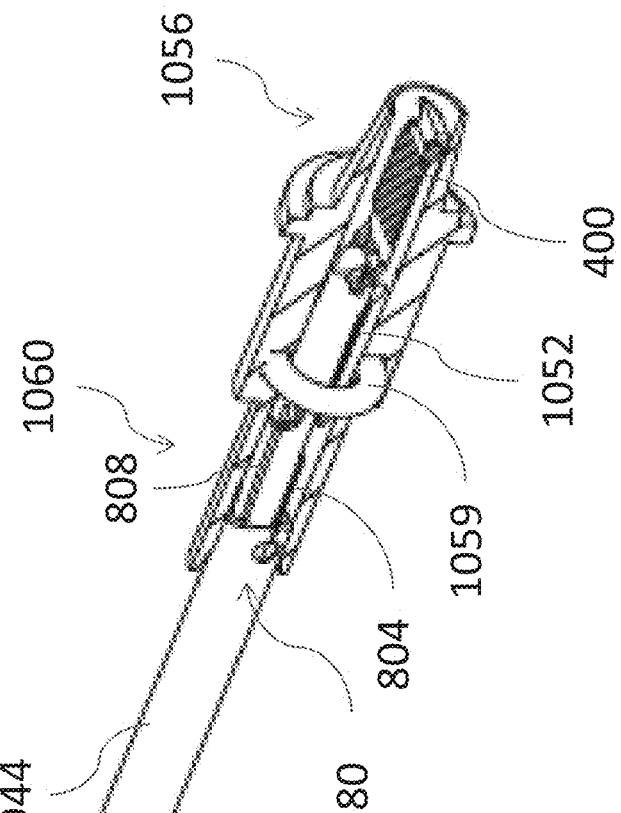

FIG. 57D shows the first member 400 and the second member 804 fully inserted into the loading capsule 794. FIG. 57D shows the distal end 980 inserted into the loading capsule 794. The loading method phase shown in FIG. 57D also can include moving the distal zone 1056 toward the hub 912 to prepare to connect the loading capsule 794 to the guide catheter 900 at the hub 912.

Figure 57E:
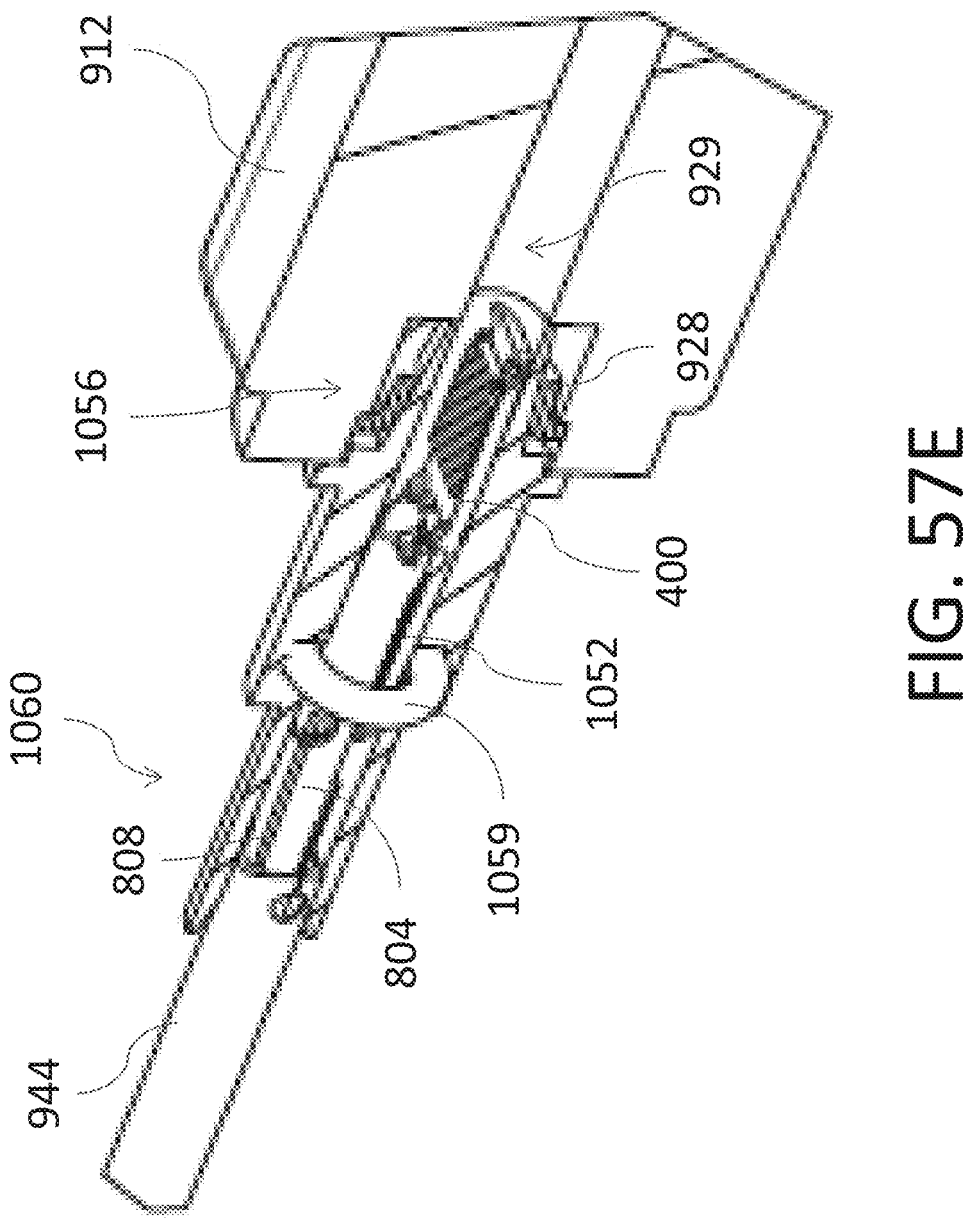
FIG. 57E is a view similar to FIG. 57D showing the loading capsule advanced into a guide catheter and opening a hemostatic valve therein.

FIG. 57E shows the distal zone 1056 inserted through the hemostatic valve 928 to provide sealed access to a lumen 929 disposed distal of the hemostatic valve 928. The lumen 929 can provide access to a lumen in the guide catheter 900. The mating of the surface of the hemostatic valve 928 and the tapered surface 1058 can assure that blood does not flow out of the guide catheter 900 at the junction with the loading capsule 794 and therefore leak out of the system during the procedure. The seal 1059 provides secondary sealing function such that any blood that passes through the hemostatic valve 928 does not flow into the prosthesis member manipulator 948.

Figure 57F:
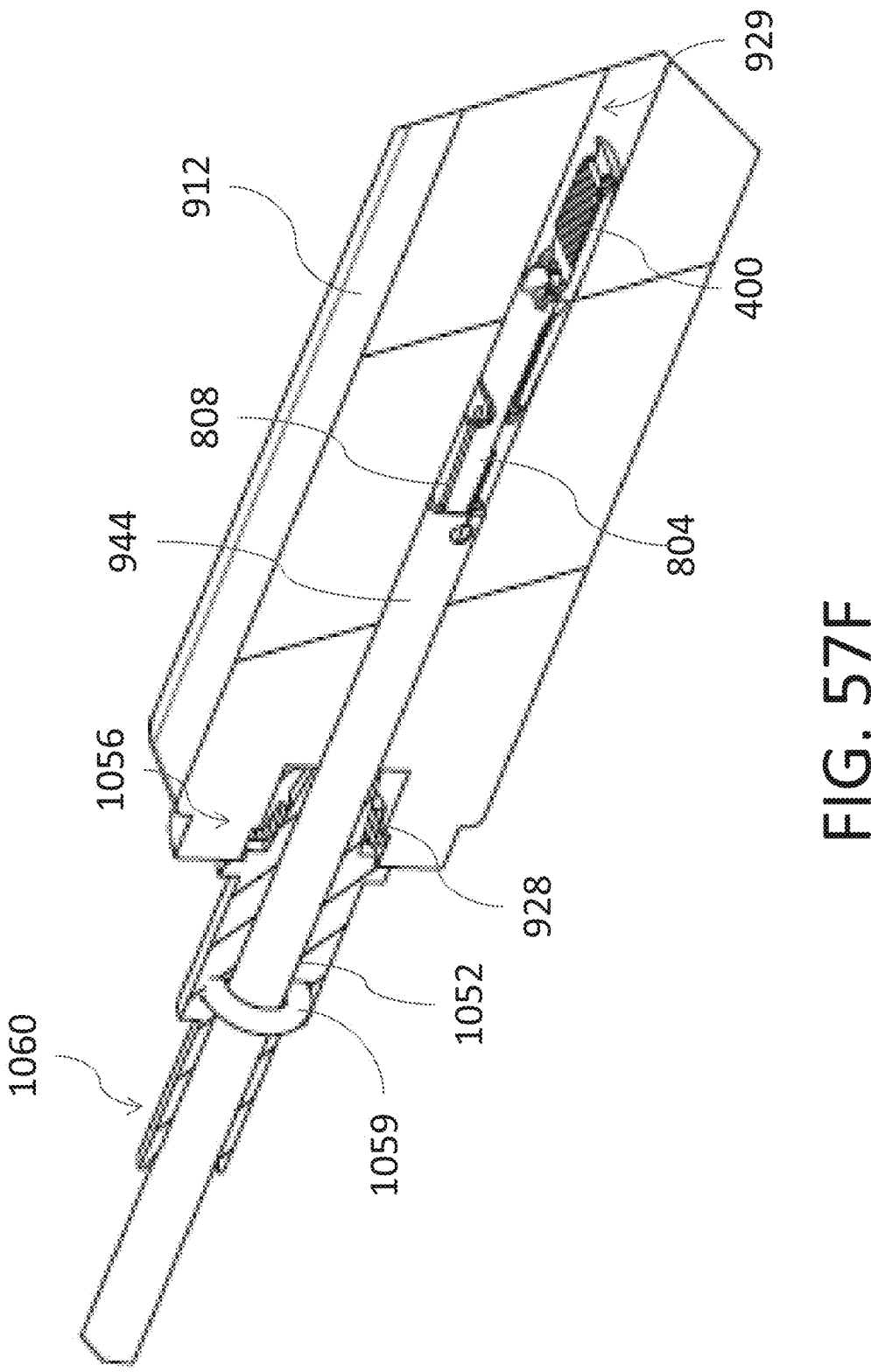
FIG. 57F shows control members for the prosthesis component and the loop-shaped tension member advanced into the guide catheter through the loading capsule illustrated in FIG. 57E.

FIG. 57F shows the first member 400 and the second member 804 being advanced by the second elongate member 944 into the hub 912 toward the guide catheter 900 through which the first member 400 can be advanced to the distal portion 920. After the first member 400 and the second member 804 are disposed adjacent to the distal end 922, 948 and 912 can be locked together at the hub and the process described in connection with FIGS. 53A-56 can be followed to secure the heart valve prosthesis 790 to the valve V as illustrated in FIG. 44.

FIGS. 58-60 show another embodiment of a delivery system 1080 that is similar to the delivery system 792 except as described differently below. The delivery system 1080 includes or is configured for advancement through the guide catheter 900. The delivery system 1080 includes a grip 1084 that is coupled with the second elongate member 944. The second elongate member 944 can include a smooth surface 1086 that provides an interface within an inside surface of the guide catheter 900. The grip 1084 enables the second elongate member 944 to be shifted relative to the guide catheter 900 such that the first member 400 can be advanced out of the guide catheter 900. The shifted position is shown in FIGS. 59 and 60. Other positions corresponding to FIGS. 53G-K can be reached by shifting the grip 1084 relative to the guide catheter 900 without resistance from detents or without requiring depressing any latches. The smooth surface 1086 allows that motion to be without any resistance or interference. For a skilled clinician or one working under visualization this configuration may be beneficial in providing immediate response without resistance. The delivery system 1080 includes a wire twister 1092 that can be locked by a twisting handle 1096. A knob 1097 located between the grip 1084 and the twisting handle 1096 in FIGS. 58 and 59 provides tension to the loop of the connector 808 through the handle 1096 at the proximal end of a control body coupled therewith, which allows the first member 400 to rotate. When the twisting handle 1096 is unlocked, tension is removed and the second member 804 can be retracted relative to the first member 400. When the twisting handle 1096 is unlocked, the wire connector 808 can be twisted simply by twisting the proximal end of the control body coupled it the handle 1096. The locking mechanism can be unlocked such that a torque applied to a twisting handle 1096 cause rotation of the first elongate member 940, discussed above, to cause the adjacent strands 862 to be twisted about each other as discussed above.

VIII. Additional Embodiments Including Ribbon Connector

Although the foregoing embodiments can provide advantageous delivery, leaflet capture and securing upon deployment FIGS. 61-65B shows various embodiments of a heart valve prosthesis that employs a ribbon connector, which can be configured as a flat wire that spans a portion of, e.g., twenty percent of, thirty percent of, forty percent of, fifty percent of, sixty percent of, seventy percent of, seventy-five percent of the width of proximal and/or distal bodies of a heart valve prosthesis, where width is measured transverse to the longitudinal axis thereof. A ribbon connector provides a number of advantages. For example, a ribbon connector can be rigid enough to rotationally orient one or more plate-like bodies of the prosthesis. The ribbon connector can be more rigid than other forms of tensions member to its greater width. Additional advantages of assembly and manufacture are also provided, such as providing a single body in the tension member in lieu of adjacent strands in a dual wire or looped wire embodiment while maintaining rotational position control.

Figure 61:
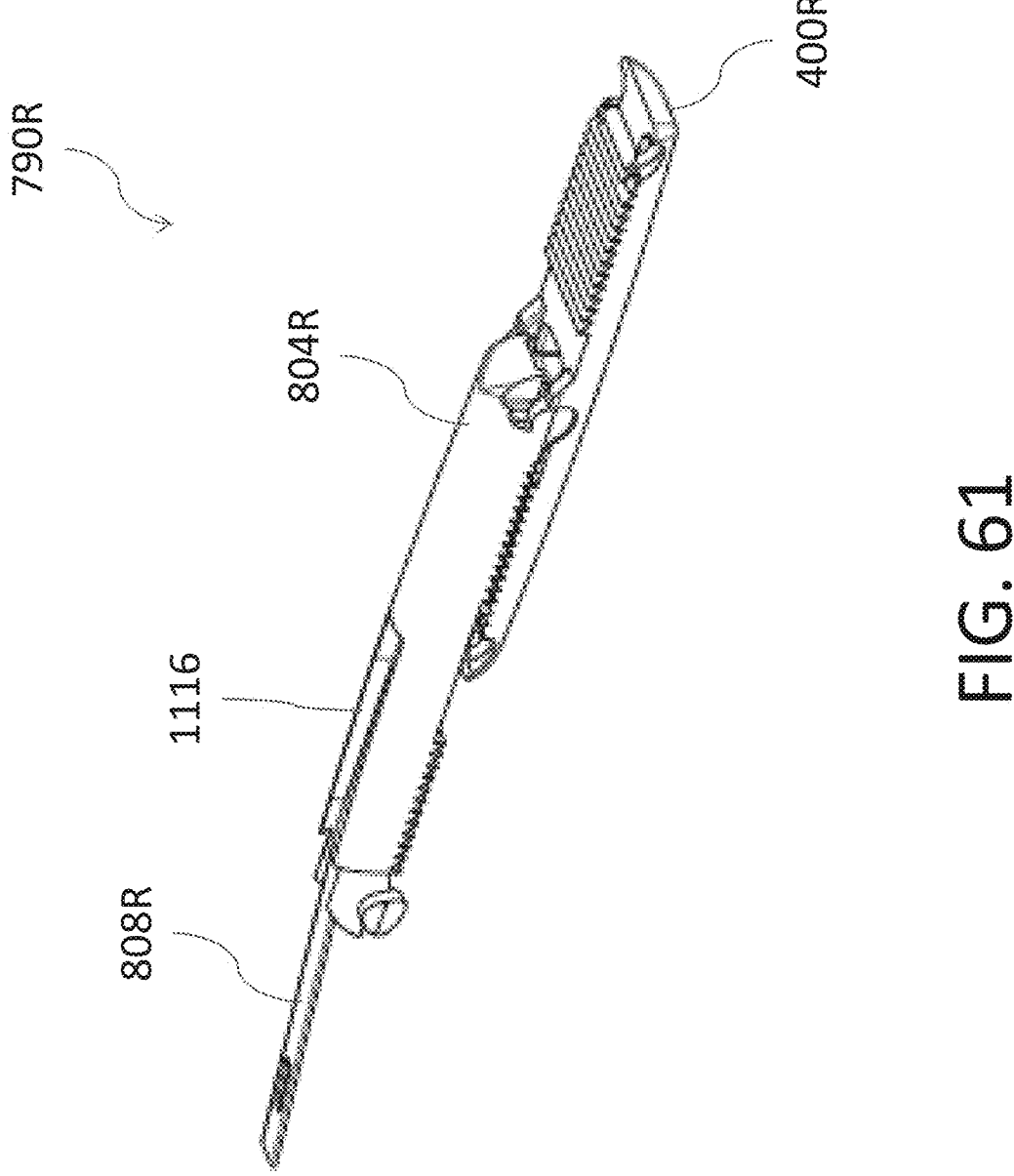
FIG. 61 is a perspective view of a heart valve prosthesis having a ribbon connector, the prosthesis in an assembled delivery configuration.
Figure 62:
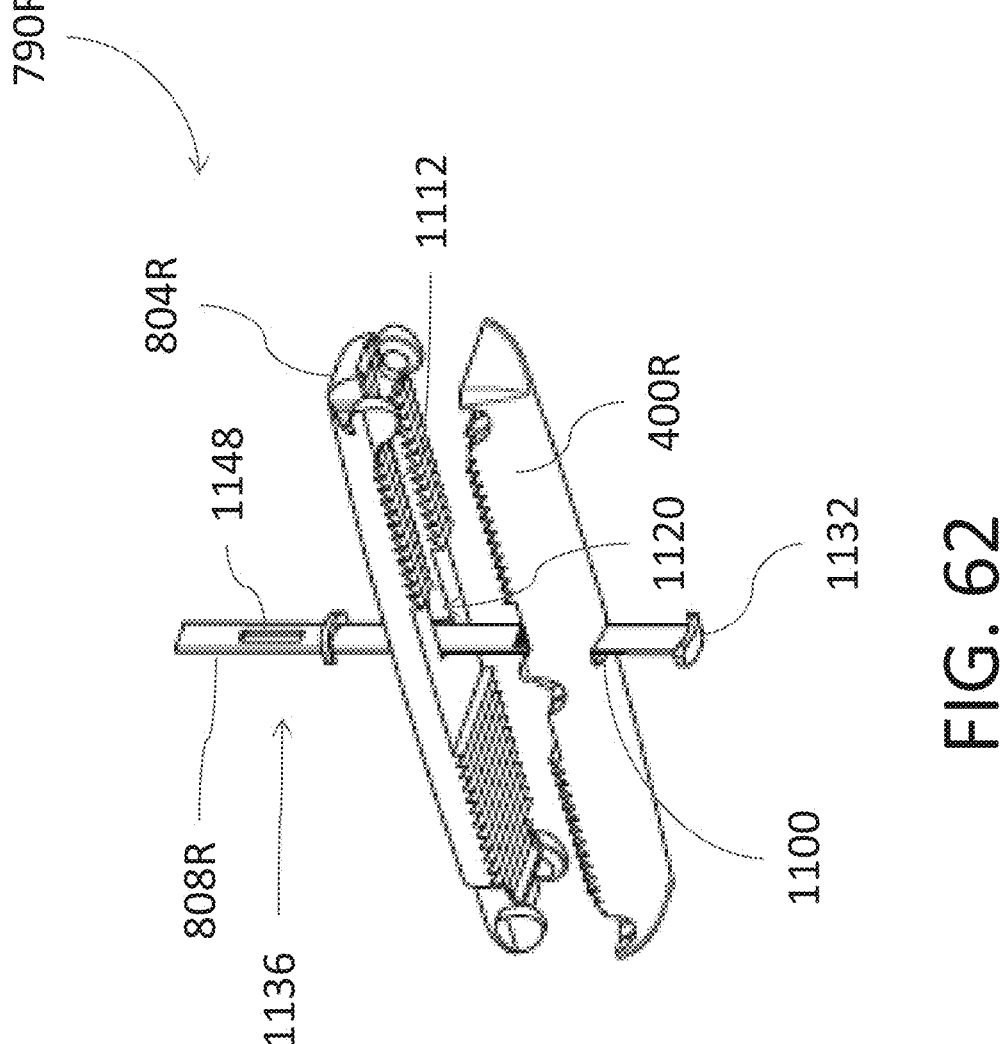
FIG. 62 is an exploded view of a distal side of the heart valve prosthesis of FIG. 61.
Figure 63:
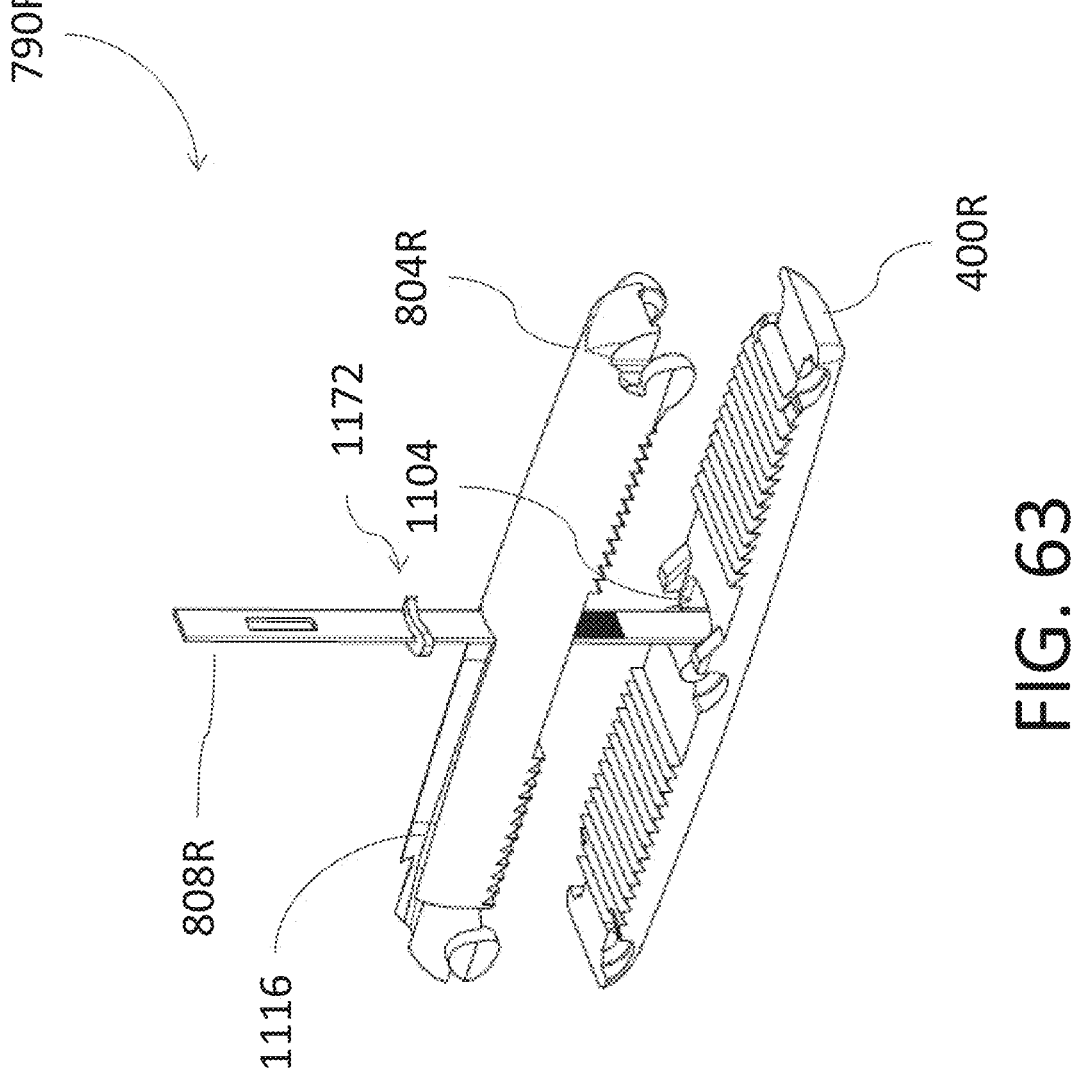
FIG. 63 is a proximal side view of the heart valve prosthesis of FIG. 61 in an intra-cardiac configuration between a delivery and a heart valve leaflet retention assembly configuration.
Figure 64:
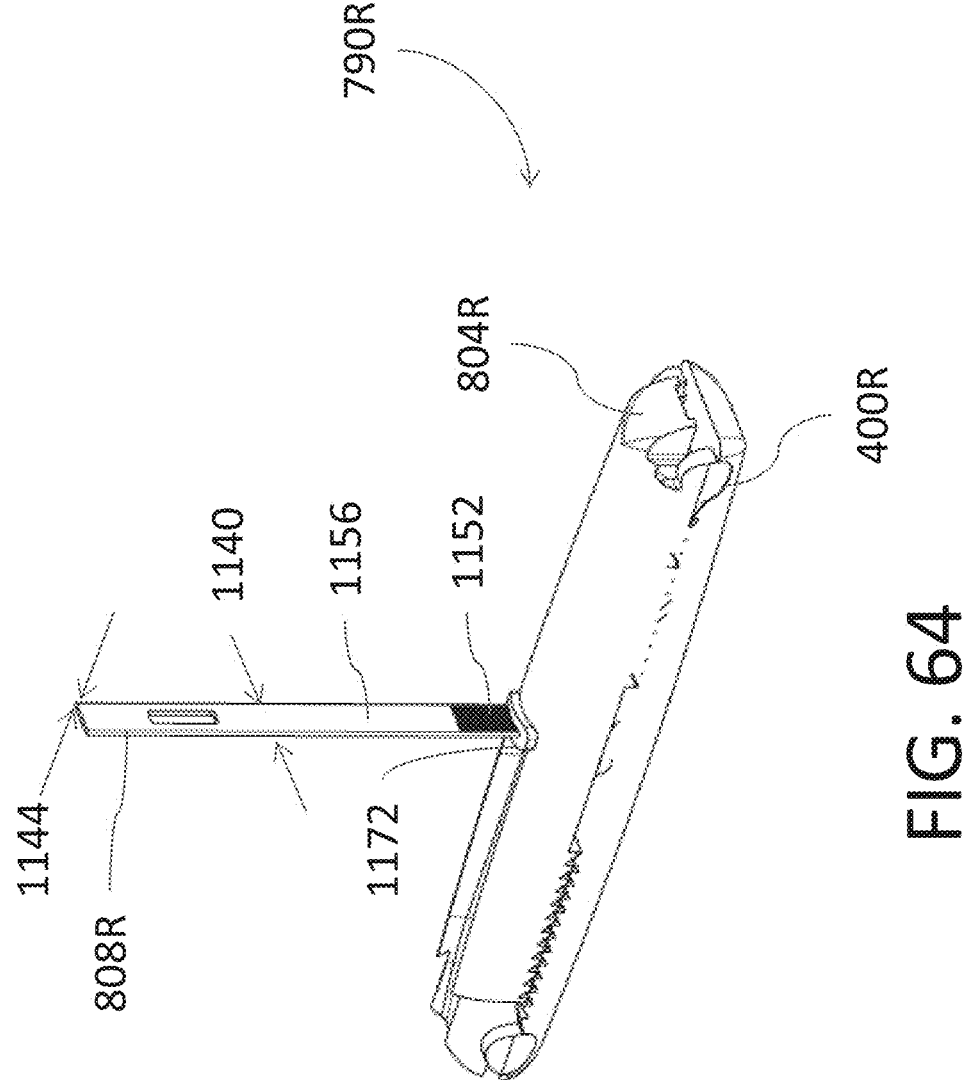
FIG. 64 is a proximal side view of the heart valve prosthesis of FIG. 61 with proximal and distal portions being held together with a connector retainer.

FIG. 61 shows an embodiment of a heart valve prosthesis 790R that includes a connector 808R configured as a ribbon as described further below. The connector 808R is disposed through a first member 400R and a second member 804R of the heart valve prosthesis 790R in a low profile configuration. The first member 400R is similar to the first member 400 described herein above except as described differently below. FIG. 62 shows that the first member 400R includes a ribbon anchor recess 1100. The ribbon anchor recess 1100 provides an opening into which an anchor portion of the connector 808R (discussed further below) can be received and retained in a valve leaflet assembly configuration. The first member 400R also includes an opening 1104 that extends from the ribbon anchor recess 1100 to a tissue engaging side of the first member 400R. The opening 1104 is sometimes referred to as a ribbon slot herein in that the opening 1104 allows the ribbon-shaped connector 808R to pass through the opening 1104 from the ribbon anchor recess 1100 (see FIG. 62) to the tissue engaging side of the first member 400R (see FIG. 63).

The second member 804R is similar to the second member 804 and the 404 discussed above, the descriptions thereof being incorporated here without being repeated. The second member 804R includes a ribbon groove 1112 disposed on a tissue engaging side of the second member 804R, as shown in FIG. 62. The second member 804R includes a ribbon groove 1116 disposed on a side opposite the tissue engaging side. The ribbon groove 1112 and the ribbon groove 1116 define a path over which the ribbon connector 808R is routed when the heart valve prosthesis 790R is in a delivery configuration (FIG. 61). For example in a delivery configuration the connector 808R is disposed in the ribbon anchor recess 1100 and passes through the opening 1104. The connector 808R extends along the ribbon groove 1112 between the first member 400R and the second member 804R. The connector 808R passes through an opening 1120 (ribbon slot) in the second member 804R from the tissue engaging side of the second member 804R to the side opposite the tissue engaging side of the second member 804R. The ribbon connector 808R extends from the opening 1120 to the ribbon groove 1116 on the side opposite the tissue engaging side of the second member 804R. The ribbon connector 808R extends from the opening 1120 to a peripheral edge of the second member 804R that is adapted to be coupled with a delivery system, similar to any of those discussed above, e.g., to the delivery system 792.

The connector 808R provides advantages as described above and in more detail below. The connector 808R includes a ribbon anchor 1132 disposed at a distal end thereof. From the ribbon anchor 1132 the connector 808R includes an elongate body 1136 that extends proximally to be disposed through the first member 400R and the second member 804R. The elongate body 1136 includes a width 1140 and a thickness 1144. The width 1140 is greater than the thickness 1144, e.g., four times greater, six times greater, eight times greater, ten times greater fifteen times greater, twenty, fifty times greater or one hundred times greater than the thickness 1144.

The connector 808R can include a control recess 1148 disposed along the elongate body 1136. The control recess 1148 can be configured to be coupled with a control body similar to the first elongate member 940 described above.

The control recess 1148 is elongate in one embodiment such that a control body can be coupled with a proximal end of the recess for maintaining tension thereon. A control body can be shifted along the control recess 1148 away from the proximal end to provide slack in the elongate body 1136 permitting pivoting of the first member 400R, similar to the methods described above. The first elongate member 940 can act on the ribbon connector 808R to break it in a controlled manner as described further below. The connector 808R can also include a ratchet zone 1152 and a smooth surface 1156 in some embodiments. The ratchet zone 1152 can include distal facing barb structures on one or both of the sides corresponding to the width 1140 of the connector 808R. The ratchet zone 1152 can configured similar to a one way ratchet or zip tie structure to enable a connector retainer 1172 to be advanced relative to the connector 808R to a position where tension is provided between along the connector 808R to cause the first member 400R and the second member 804R to provide compression at the interface therebetween, e.g., to heart valve leaflet disposed therebetween.

The connector retainer 1172 can include a rigid body that is disposed over the connector 808R, for example with the connector 808R extending through an opening 1176 disposed between proximal and distal sides thereof. The opening 1176 includes a ribbon slot through which the ribbon connector 808R can extend. In one embodiment, one or more barbs are disposed in the opening 1176 such that the barbs can act against the distal facing barbs in the ratchet zone 1152 of the connector 808R.

Methods of deploying the heart valve prosthesis 790R can proceed as follows. The heart valve prosthesis 790R can be delivered in an assembled delivery configuration similar to those described above. For instance the first member 400R can be shifted relative to the second member 804R in the delivery state compared to the implantation state. In the shifted position a peripheral portion of the second member 804R can be aligned to a central portion of the first member 400R. From this position the ribbon connector 808R can thread through the first member 400R and the second member 804R as described above, along the opening 1104, the ribbon groove 1112, through the opening 1120, and along the ribbon groove 1116. The connector retainer 1172 (if provided) can be disposed along the elongate body 1136 proximal of a peripheral edge of the second member 804R which is proximal of the proximal-most peripheral edge of the first member 400R in the assembled delivery configuration shown in FIG. 61. The motion and control of the components of the heart valve prosthesis 790R when in the configuration of FIG. 61 can be provided by a delivery system that can be similar to the delivery system 792.

Upon reaching the heart, the heart valve prosthesis 790R can be advanced across the valve to be treated, e.g., across the tricuspid valve. The delivery system can be manipulated such that the first member 400R pivots from the position of FIG. 61 to a transverse position, analogous to that shown in FIG. 53F. Thereafter, a tension on the connector 808R can be lessened such that the first member 400R can separate from the second member 804R. This can provide the relative positioning of the first member 400R and the second member 804R shown in FIG. 63. Providing proper positioning across the line of coaptation can be easily achieved by twisting the ribbon connector 808R which is able to transfer torque to the first member 400R. Thereafter, the second member 804R can be pushed up into engagement with the first member 400R and the connector retainer 1172 can be advanced along the elongate body 1136 of the connector 808R until the connector retainer 1172 is in the ratchet zone 1152. Further advancement of the connector retainer 1172 creates enhanced compression between the first member 400R and the second member 804R that can be maintained by the engagement of barbs in the connector retainer 1172 and in or around the opening 1176. Thereafter, the connector 808R can be fractured at a fracture point 1160 proximal of the location of the connector retainer 1172.

Figure 65A:
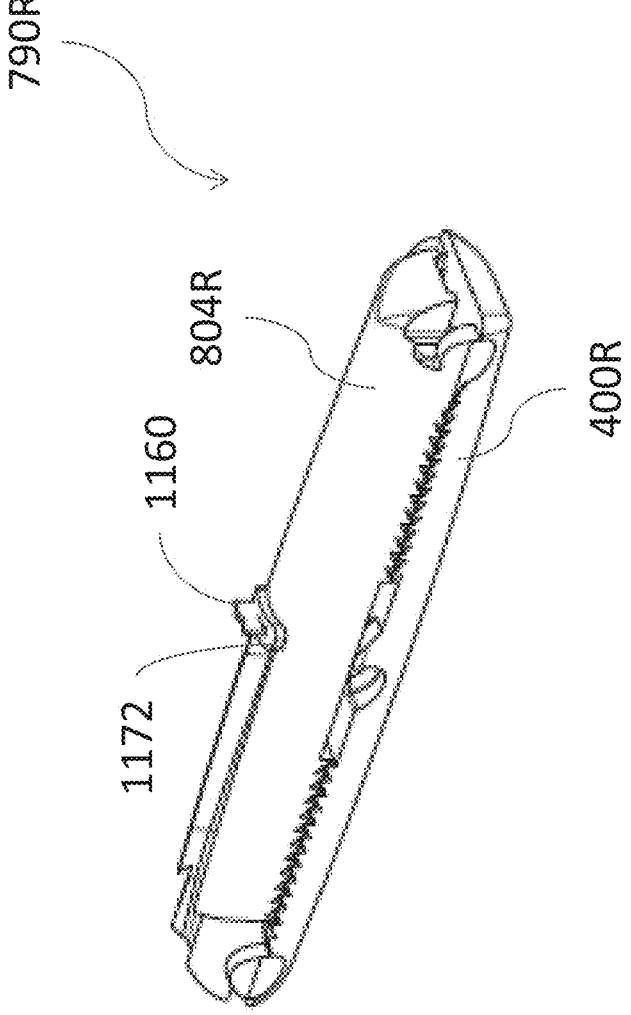
FIG. 65A is a proximal side view of the heart valve prosthesis of FIG. 61 with excess ribbon connector separated from the prosthesis.
Figure 65B:
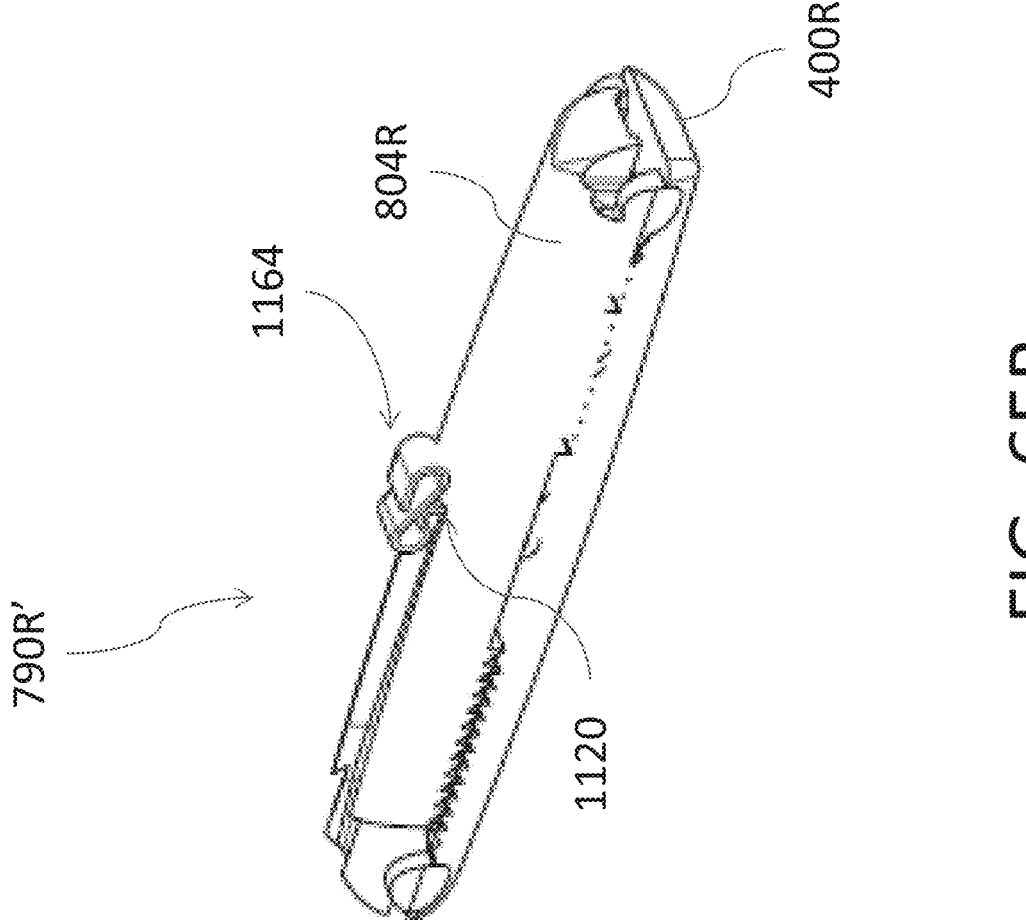
FIG. 65B is a heart valve prosthesis with proximal and distal portions being held together by a bend retainer including a bent or folded portion of a ribbon.

FIG. 65B shows another embodiment of a heart valve prosthesis 790R' that is similar to the heart valve prosthesis 790R except in that the connector retainer 1172 is not needed. In this approach, the second member 804R is secured to the first member 400R by folding the connector 808R away from the initial direction until the folds overlap at least a portion of a side of the second member 804R opposite a tissue contacting side thereof. The connector 808R is thus provided with a bend retainer 1164. The bend retainer 1164 is a retention structure that is primarily or completely formed of folds or bends in the ribbon connector 808R itself. The shape of the bend retainer 1164 can be defined during the procedure by the user manipulating one or more control bodies. The bend retainer 1164 can be configured to bend at pre-defined positions. For example, the elongate body 1136 can be pre-folded, scored, perforated or otherwise weakened in specific locations to induce bending upon specific compressive loads. A control body can be shifted to the distal end of the control recess 1148. Continued application of force on a control body transferred to the distal end of the control recess 1148 can cause a suitable number of bends, e.g., one, two, three, four, five or six more bends proximal of the second member 804R. The bends in the elongate body 1136 can be disposed on both sides of the opening 1120 in the second member 804R.

In various methods herein the guide catheter 900 can be left in place and other components of the delivery system 792 can be exchanged so that multiple prostheses can be deployed at a single heart valve. A second heart valve prosthesis 790, heart valve prosthesis 790R, heart valve prosthesis 790R' can be loaded into the same or a second loading capsule 794. A second or the same prosthesis member manipulator 948 can be coupled with the heart valve prosthesis 790, heart valve prosthesis 790R, heart valve prosthesis 790R' and advanced through the same or a second loading capsule 794. The guide catheter 900 can be left in place while second (and, if needed, subsequent) heart valve prostheses 790, heart valve prosthesis 790R, heart valve prosthesis 790R' are deployed.

Terminology

As used herein, the relative terms "proximal" and "distal" can be defined from the perspective of the implant. Thus, proximal refers to the direction of the rigid member or plate that is disposed in the right atrium and distal refers to the direction of the plate that is disposed in the right ventricle.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense)

so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Although certain embodiments and examples have been described herein, it should be emphasized that many variations and modifications may be made to the heart valve prostheses and delivery systems shown and described in the present disclosure, the elements of which are to be understood as being differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, it will be understood by those skilled in the art that the scope of the inventions extends beyond the specifically disclosed embodiments to any and all embodiments having equivalent elements, modifications, omissions, combinations or sub-combinations of the specific features and aspects of the embodiments (e.g., of aspects across various embodiments), adaptations and/or alterations, and uses of the inventions as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "inserting a delivery catheter into a right internal jugular vein" include "instructing insertion of a delivery catheter into a right internal jugular vein."

What is claimed is:

1. A method, comprising:
advancing a distal body and at least a portion of a proximal body on a delivery catheter into a first heart chamber of a heart by passing the distal body through a heart valve;
exposing the distal body and at least the portion of the proximal body outside a distal end of the delivery catheter while in the first heart chamber;
pivoting the distal body about the proximal body while maintaining contact between the proximal body and the distal body;
separating the proximal body from the distal body;
withdrawing the proximal body from the first heart chamber to a second heart chamber by passing the proximal body through the heart valve;
capturing a portion of a leaflet between the proximal body and the distal body; and
securing the proximal body to the distal body to keep the captured leaflets between the proximal body and the distal body.

2. The method of claim 1, wherein pivoting further comprises rotating the distal body so that a longitudinal axis of the distal body is aligned substantially perpendicular to a longitudinal axis of the proximal body.

3. The method of claim 2, further comprising, after rotating the distal body, aligning the proximal body so that a longitudinal axis of the proximal body is substantially parallel to the longitudinal axis of the distal body.

4. The method of claim 1, wherein securing further comprises cinching a tension member about the distal body and the proximal body.

5. The method of claim 4, wherein cinching the tension member comprises cinching a knot by advancing a first knot toward the proximal body with an elongate control body.

6. The method of claim 5, wherein cinching the knot further comprises:

withdrawing the elongate control body away from the proximal body to position a second knot between the elongate control body and the proximal body; and advancing the second knot toward the first knot.

7. The method of claim 1, wherein securing further comprises shifting an elongate member of a connector to advance the proximal body and/or the distal body.

8. The method of claim 7, further comprising cinching a knot about a proximal body of the connector.

9. The method of claim 1, further comprising unlatching a latch mechanism disposed between coaxial shells of the delivery catheter to cause relative movement within the delivery catheter to control one or more of a change in orientation or in relative position of the distal body to the proximal body or the proximal body to the distal body.

10. The method of claim 1, further comprising urging a proximal portion of a prosthesis manipulator distal relative to a distal portion of the prosthesis manipulator such that the proximal portion of the prosthesis manipulator is advanced form a first pre-defined position to a second pre-defined position.

11. A method comprising:

advancing a distal body and at least a portion of a proximal body on a delivery catheter into a first heart chamber of a heart by passing the distal body through a heart valve;

pivoting the distal body about the proximal body while maintaining contact between the proximal body and the distal body;

separating the proximal body from the distal body;

withdrawing the proximal body from the first heart chamber to a second heart chamber by passing the proximal body through the heart valve;

capturing a portion of a leaflet between the proximal body and the distal body; and securing the proximal body to the distal body to keep the captured leaflets between the proximal body and the distal body, wherein pivoting comprises sliding a first curved surface of the distal body over a second curved surface of the proximal body.

12. A method comprising:

advancing a distal body and at least a portion of a proximal body on a delivery catheter into a first heart chamber of a heart by passing the distal body through a heart valve;

pivoting the distal body about the proximal body while maintaining contact between the proximal body and the distal body;

separating the proximal body from the distal body;

withdrawing the proximal body from the first heart chamber to a second heart chamber by passing the proximal body through the heart valve;

capturing a portion of a leaflet between the proximal body and the distal body; and securing the proximal body to the distal body to keep the captured leaflets between the proximal body and the distal body, wherein pivoting further comprises receiving a protruding portion of the proximal body into a recessed portion of the distal body.

13. A method comprising:

advancing a distal body and at least a portion of a proximal body on a delivery catheter into a first heart chamber of a heart by passing the distal body through a heart valve;

pivoting the distal body about the proximal body while maintaining contact between the proximal body and the distal body;

separating the proximal body from the distal body;

withdrawing the proximal body from the first heart chamber to a second heart chamber by passing the proximal body through the heart valve;

capturing a portion of a leaflet between the proximal body and the distal body; and securing the proximal body to the distal body to keep the captured leaflets between the proximal body and the distal body, wherein securing further comprises cinching a tension member about the distal body and the proximal body, wherein cinching the tension member comprises twisting two adjacent strands of wire about each other until a proximal portion of the wire separates from a distal portion, the distal portion securing the proximal body to the distal body.

14. The method of claim 13, wherein the wire comprises a fracture zone such that the proximal portion of the wire separates from the distal portion at a pre-defined location.

15. A method comprising:

advancing a distal body and at least a portion of a proximal body on a delivery catheter into a first heart chamber of a heart by passing the distal body through a heart valve;

pivoting the distal body about the proximal body while maintaining contact between the proximal body and the distal body;

separating the proximal body from the distal body;

withdrawing the proximal body from the first heart chamber to a second heart chamber by passing the proximal body through the heart valve;

capturing a portion of a leaflet between the proximal body and the distal body; and securing the proximal body to the distal body to keep the captured leaflets between the proximal body and the distal body, wherein capturing comprises compressing a first portion of the leaflet between a lateral stabilization member of the proximal body and a concave recess of the distal body.

16. The method of claim 15, wherein the lateral stabilization member comprises a convex projection of the proximal body.

* * * * *